(12) United States Patent
Lebedev et al.

(10) Patent No.: US 11,568,990 B2
(45) Date of Patent: Jan. 31, 2023

(54) CHARACTERIZING AND IDENTIFYING BIOLOGICAL STRUCTURE

(71) Applicant: Sensome SAS, Massy (FR)

(72) Inventors: Gor Lebedev, Massy (FR); Pierluca Messina, Massy (FR)

(73) Assignee: Sensome SAS, Massy (FR)

( * ) Notice: Subject to any disclaimer, the term of this patent is extended or adjusted under 35 U.S.C. 154(b) by 250 days.

(21) Appl. No.: 16/462,870

(22) PCT Filed: Nov. 21, 2017

(86) PCT No.: PCT/EP2017/079960
§ 371 (c)(1),
(2) Date: May 21, 2019

(87) PCT Pub. No.: WO2018/091746
PCT Pub. Date: May 24, 2018

(65) Prior Publication Data
US 2021/0174957 A1 Jun. 10, 2021

Related U.S. Application Data

(60) Provisional application No. 62/424,693, filed on Nov. 21, 2016.

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/02007* (2013.01); *A61B 5/0538* (2013.01);
(Continued)

(58) Field of Classification Search
CPC ........ G16H 50/20; G16H 20/40; G16H 50/50; A61B 5/7267; A61B 2562/02;
(Continued)

(56) References Cited

U.S. PATENT DOCUMENTS

| 5,447,529 A | 9/1995 | Marchlinksi et al. |
| 5,800,350 A | 9/1998 | Coppleson et al. |
| (Continued) | | |

FOREIGN PATENT DOCUMENTS

| AU | 4755602 A | 12/2002 |
| CN | 1353619 A | 6/2002 |
| (Continued) | | |

OTHER PUBLICATIONS

Amemiya et al., Denkikagaku: Sokutei to Kaiseki no Tebiki Inpidansuhou (1). Electrochemistry, Electrochemistry society of japan. Apr. 5, 2006;74(4):351-357.
(Continued)

*Primary Examiner* — Carl H Layno
*Assistant Examiner* — Aya Ziad Bakkar
(74) *Attorney, Agent, or Firm* — Greenberg Traurig, LLP; Andrew J. Tibbetts

(57) ABSTRACT

Embodiments described relate to techniques for identifying and characterizing biological structures using machine learning techniques. These techniques may be employed to enable a device to identify the particular type of tissue and/or cells (e.g., platelets, smooth muscle cells, or endothelial cells) in, for example, a biological structure, which may be a tissue or a lesion of a duct (e.g., vasculature) in an animal (e.g., a human or non-human animal), among other structures. The machine learning techniques may use raw impedance spectroscopy measurement data in addition to values derived from that raw data. In addition, the machine learning techniques may be used to select frequencies at which to measure impedance and select features to extract from the measured impedance at the selected frequencies to arrive at a small set of frequencies that allow for reliable differentiation.

23 Claims, 34 Drawing Sheets

(51) Int. Cl.
  *G16H 50/50* (2018.01)
  *G16H 20/40* (2018.01)
  *A61B 5/02* (2006.01)
  *A61B 5/0538* (2021.01)

(52) U.S. Cl.
  CPC .......... *A61B 5/7225* (2013.01); *A61B 5/7267* (2013.01); *G16H 20/40* (2018.01); *A61B 2562/02* (2013.01); *G16H 50/50* (2018.01)

(58) Field of Classification Search
  CPC . A61B 5/7225; A61B 5/02007; A61B 6/5211; A61B 5/053; A61B 2017/00026; A61B 5/0531
  See application file for complete search history.

(56) References Cited

U.S. PATENT DOCUMENTS

| | | |
|---|---|---|
| 5,938,624 A | 8/1999 | Akerfeldt et al. |
| 6,063,028 A | 5/2000 | Luciano |
| 6,090,052 A | 7/2000 | Akerfeldt et al. |
| 6,106,486 A | 8/2000 | Tenerz et al. |
| 6,206,835 B1 | 3/2001 | Spillman, Jr. et al. |
| 6,437,551 B1 | 8/2002 | Krulevitch et al. |
| 6,461,301 B2 | 10/2002 | Smith |
| 6,679,269 B2 | 1/2004 | Swanson |
| 8,277,386 B2 | 10/2012 | Ahmed et al. |
| 8,491,567 B2 | 7/2013 | Magnin et al. |
| 8,777,898 B2 | 7/2014 | Suon et al. |
| 8,840,560 B2 | 9/2014 | Hossack et al. |
| 9,121,806 B1 | 9/2015 | Bhansali et al. |
| 9,301,699 B2 | 4/2016 | Hubinette et al. |
| 10,912,482 B2 | 2/2021 | Bozsak et al. |
| 2001/0051774 A1* | 12/2001 | Littrup ................. A61B 5/4312 600/547 |
| 2002/0043113 A1 | 4/2002 | Tulkki et al. |
| 2002/0077627 A1 | 6/2002 | Johnson et al. |
| 2002/0177782 A1 | 11/2002 | Penner |
| 2005/0065592 A1 | 3/2005 | Holzer |
| 2006/0047205 A1 | 3/2006 | Ludomirsky et al. |
| 2006/0254600 A1 | 11/2006 | Danek et al. |
| 2007/0255145 A1 | 11/2007 | Smith et al. |
| 2007/0255270 A1 | 11/2007 | Carney |
| 2008/0262489 A1 | 10/2008 | Steinke |
| 2010/0191141 A1* | 7/2010 | Aberg ................. A61B 5/7267 600/547 |
| 2011/0054583 A1 | 3/2011 | Litt et al. |
| 2011/0251469 A1 | 10/2011 | Varadan |
| 2012/0016206 A1 | 1/2012 | Ramarajan et al. |
| 2012/0036689 A1 | 2/2012 | Sjosten et al. |
| 2012/0061257 A1 | 3/2012 | Yu et al. |
| 2012/0172731 A1 | 7/2012 | Smith |
| 2012/0190989 A1 | 7/2012 | Kaiser et al. |
| 2012/0316454 A1 | 12/2012 | Carter |
| 2013/0274712 A1 | 10/2013 | Schecter |
| 2013/0282084 A1 | 10/2013 | Mathur et al. |
| 2014/0005558 A1 | 1/2014 | Gregorich |
| 2014/0058197 A1 | 2/2014 | Salahieh et al. |
| 2014/0058275 A1 | 2/2014 | Gregorich et al. |
| 2014/0066790 A1 | 3/2014 | Burkett et al. |
| 2014/0066791 A1 | 3/2014 | Burkett |
| 2014/0081244 A1 | 3/2014 | Voeller et al. |
| 2014/0180031 A1 | 6/2014 | Anderson |
| 2014/0276109 A1 | 9/2014 | Gregorich |
| 2014/0276223 A1 | 9/2014 | Gustafsson |
| 2014/0284422 A1 | 9/2014 | Sapir |
| 2014/0343382 A1 | 11/2014 | Kersey et al. |
| 2015/0032011 A1 | 1/2015 | McGowan et al. |
| 2015/0051499 A1 | 2/2015 | McGowan |
| 2015/0209526 A1 | 7/2015 | Matsubara et al. |
| 2015/0297807 A1 | 10/2015 | Leblanc et al. |
| 2015/0313478 A1 | 11/2015 | Veszelei et al. |
| 2016/0051323 A1 | 2/2016 | Stigall et al. |
| 2016/0058382 A1 | 3/2016 | Burkett et al. |
| 2016/0058977 A1 | 3/2016 | Burkett et al. |
| 2016/0073957 A1 | 3/2016 | Szunyog |
| 2016/0121085 A1 | 5/2016 | Burkett et al. |
| 2016/0287178 A1 | 10/2016 | Ranganathan et al. |
| 2016/0303354 A1 | 10/2016 | Burkett et al. |
| 2018/0303372 A1 | 10/2018 | Bozsak et al. |
| 2019/0388002 A1 | 12/2019 | Bozsak et al. |

FOREIGN PATENT DOCUMENTS

| | | |
|---|---|---|
| CN | 1400462 A | 3/2003 |
| CN | 1504578 A | 6/2004 |
| CN | 102016575 A | 4/2011 |
| CN | 102973267 A | 3/2013 |
| DE | 101 03 503 A1 | 8/2002 |
| EP | 0904739 A | 3/1999 |
| EP | 2271933 B1 | 12/2012 |
| JP | 2004-517677 A | 6/2004 |
| JP | 2004-520865 A | 7/2004 |
| JP | 2011-520118 A | 7/2011 |
| JP | 2012515588 A | 7/2012 |
| JP | 2015-533611 A | 11/2015 |
| WO | WO 99/42176 A1 | 8/1999 |
| WO | WO 01/37726 A1 | 5/2001 |
| WO | WO 02/32335 A1 | 4/2002 |
| WO | WO 03/057011 A2 | 7/2003 |
| WO | WO 2006/113747 A2 | 10/2006 |
| WO | WO 2009/096821 A1 | 8/2009 |
| WO | WO 2009/103156 A1 | 8/2009 |
| WO | WO 2009/136157 A2 | 11/2009 |
| WO | WO 2014/071223 A1 | 5/2014 |
| WO | WO 2016/011309 A2 | 1/2016 |
| WO | WO 2016/050972 A1 | 4/2016 |
| WO | WO 2016/181318 A1 | 11/2016 |

OTHER PUBLICATIONS

European Communication for European Application No. 16785160.9 dated Sep. 16, 2019.
U.S. Appl. No. 16/092,872, filed Oct. 11, 2018, Bozsak et al.
U.S. Appl. No. 15/769,968, filed Apr. 20, 2018, Bozsak et al.
FR 1459531, Oct. 3, 2014, French Communication.
FR 1459531, Jun. 30, 2015, French Communication.
FR 1560174, Oct. 23, 2015, Written Opinion on Patentability.
FR 1560174, Jun. 17, 2016, Preliminary Search Report.
PCT/EP2015/072859, Dec. 3, 2015, International Search Report and Written Opinion.
PCT/EP2015/072859, Apr. 13, 2017, International Preliminary Report on Patentability.
PCT/EP2016/075456, Dec. 9, 2016, International Search Report and Written Opinion.
PCT/EP2016/075456, May 3, 2018, International Preliminary Report on Patentability.
PCT/EP2017/058169, Jun. 21, 2017, International Search Report and Written Opinion.
PCT/EP2017/079960, Apr. 5, 2018, International Search Report and Written Opinion.
PCT/IB2017/001230, May 4, 2018, International Search Report and Written Opinion.
French Communication for French Application No. 1459531 dated Jun. 30, 2015.
French Communication for French Application No. 1459531 dated Oct. 3, 2014.
International Preliminary Report on Patentability for International Application No. PCT/EP2015/072859 dated Apr. 13, 2017.
International Preliminary Report on Patentability for International Application No. PCT/EP2016/075456 dated May 3, 2018.
International Search Report and Written Opinion for International Application No. PCT/EP2015/072859 dated Dec. 3, 2015.
International Search Report and Written Opinion for International Application No. PCT/EP2016/075456 dated Dec. 9, 2016.
International Search Report and Written Opinion for International Application No. PCT/EP2017/058169 dated Jun. 21, 2017.
International Search Report and Written Opinion for International Application No. PCT/IB2017/001230 dated May 4, 2018.

(56) References Cited

OTHER PUBLICATIONS

International Search Report and Written Opinion for International Application No. PCT/EP2017/079960 dated Apr. 5, 2018.
Preliminary Search Report for French Application No. 1560174 dated Jun. 17, 2016.
Written Opinion on Patentability for French Application No. 1560174 dated Oct. 23, 2015.
[No Author Listed], Electronique et informatique. Daniel Robert. http://www.electronique-et-informatique.fr/anglais/Digit/Digit_8T.html Sep. 22, 2006. Last accessed Aug. 7, 2018. 9 pages.
[No Author Listed], Ring oscillator. https://en.wikipedia.org/w/index.php?title=Ring oscillator&oldid=674008095 Aug. 1, 2015. Last accessed Aug. 7, 2018. 4 pages.
Arndt et al., Bioelectrical impedance assay to monitor changes in cell shape during apoptosis. Biosensors and Bioelectronics. 2004;19:583-94.
Bilge et al., Label-Free Recognition of Drug Resistance via Impedimetric Screening of Breast Cancer Cells. Plos One. 2013;8(3).
Brug et al., The Analysis of Electrode Impedances Complicated by the Presence of a Constant Phase Element. Journal of Electroanalytical Chemistry and Interfacial Electrochemistry. 1984;176:275-95.
Chauveau et al., Ex Vivo Discrimination between Normal and Pathological Tissues in Human Breast Surgical Biopsies Using Bioimpedance Spectroscopy. Annals of the New York Academy of Sciences. 1999;873:42-50.
Cho et al., Chip-based time-continuous monitoring of toxic effects on stem cell differentiation. Annals of Anatomy. 2009;191:145-52.
Cho et al., Electrical characterization of human mesenchymal stem cell growth on microelectrode. Microelectronic Engineering. Science Direct. 2008;85:1272-4.
Cho et al., Impedance monitoring of herpes simplex virus-induced cytopathic effect in Vero cells. Elsevier. Sensors and Actuators B. 2007;123:978-82.
Cole et al., Dispersion and Absorption in Dielectrics. Journal of Chemical Physics. 1941;9:341-51.
Franks et al., Impedance Characterization and Modeling of Electrodes for Biomedical Applications. Biomedical Engineering. IEEE Transactions on Biomedical Engineering. 2005;52(7):1295-1302.
Giaever et al., A morphological biosensor for mammalian cells. Nature. 1993;366:591-2.
Giaever et al., Micromotion of mammalian cells measured electrically. Proceedings of the National Academy of Sciences. 1991;88:7896-900.
Grimnes et al., Bioimpedance and Bioelectricity Basics. Academic. Elsevier. Second Edition. 2000. 484 pages.
Helen et al., Investigation of tissue bioimpedance using a macroneedle with a potential application in determination of needle-to-nerve proximity. Proceedings of the 8th International Conference on Sensing Technology. Sep. 2-4, 2014. 376-80.
Hilderbrandt et al., Detection of the osteogenic differentiation of mesenchymal stem cells in 2D and 3D cultures by electrochemical impedance spectroscopy. Journal of Biotechnology. 2010;148:83-90.
Hirschorn et al., Determination of effective capacitance and film thickness from constant-phase-element parameters. Electrochimica Acta. 2010;55:6218-27.
Linderholm et al., Two-dimensional impedance imaging of cell migration and epithelial stratification. Lab on a Chip. Paper. 2006;6:1155-62.
Luong et al., Monitoring Motility, Spreading, and Mortality of Adherent Insect Cells Using an Impedance Sensor. Analytical Chemistry. 2001;73:1844-8.
Nguyen et al., A cell impedance sensor chip for cancer cells detection with single cell resolution. 2013 IEEE Sensors. Nov. 3, 2013. 1-4.
Orazem et al., Dielectric Properties of Materials Showing Constant-Phase-Element (CPE) Impedance Response. Journal of the Electrochemcial Society. 2013;160(6):C215-C225.
Orazem et al., Electrochemical Impedance Spectroscopy. John Wiley & Sons, Inc. 2008. 533 pages.
Pauly et al., Electrical Properties of Mitochondrial Membranes. The Journal of Biophysical and Biochemical Cytology. 1960;7(4):589-601.
Qiao et al., Bioimpedance Analysis for the Characterization of Breast Cancer Cells in Suspension. Biomedical Engineering. IEEE Transactions. 2012;59:2321-90.
Rigaud et al., In vitro tissue characterization and modelling using electrical impedance measurements in the 100 Hz-10 MHz frequency range. Physiological Measurement. 1995;16:A15-A28.
Schade-Kampmann et al., On-chip non-invasive and label-free cell discrimination by impedance spectroscopy. Cell Prolif. 2008;41:830. 40.
Srinivasaraghavan et al., Microelectrode bioimpedance analysis distinguishes basal and claudin-low subtypes of triple negative breast cancer cells. Biomedical Microdevices. 2015;17(4):1-11.
Xiao et al., Assessment of Cytotoxicity Using Electric Cell-Substrate Impedance Sensing: Concentration and Time Response Function Approach. Analytical Chemistry. 2002;74:5748-53.
Xu et al., A review of impedance measurements of whole cells. Biosensors and Bioelectronics. Oct. 22, 2015. vol. 77. 824-836.
EP16785160.9, Sep. 16, 2019, European Communication.
Office Action dated Jul. 26, 2022 in corresponding Japanese Patent Application No. 2019-547781.
English translation of the Office Action dated Jul. 26, 2022 in corresponding Japanese Patent Application No. 2019-547781.

* cited by examiner

CHARACTERIZING AND IDENTIFYING BIOLOGICAL STRUCTURE

CROSS-REFERENCE TO RELATED APPLICATIONS

This Application is a national stage filing under 35 U.S.C. § 371 of international Patent Application Serial No. PCT/EP2017/079960, filed Nov. 21, 2017, entitled "CHARACTERIZING AND IDENTIFYING BIOLOGICAL STRUCTURE," which claims the benefit of U.S. Provisional Patent Application Ser. No. 62/424,693, filed Nov. 21, 2016, entitled "CHARACTERIZING AND IDENTIFYING BIOLOGICAL STRUCTURE," each of which is incorporated herein by reference in its entirety.

BACKGROUND

Blockages of blood vessels (including veins or arteries) may occur in various parts of an animal (e.g., a human or a non-human animal) and may have significant repercussions. In an ischemic stroke, for example, a blood clot fully or partially blocks blood flow in a cerebral artery. If the clot is not treated quickly, insufficient blood flow may cause irreparable damage to the brain.

Blockages may be caused by blood clots, which may be caused by coagulation of red and/or white blood cells and/or platelets within a blood vessel. The coagulation may be triggered by a variety of factors, including an injury, abnormal blood flow at the site of the blockage, a disease/condition predisposing an animal to coagulation, and/or other factors.

A common treatment of a clot is chemical dissolution of the clot, which is feasible within the first 4.5 hours following blockage of a blood vessel. Another common option is mechanical thrombectomy, in which an aspiration catheter or a stent-retriever is used to remove the blood clot from the blood vessel.

Stent-retrievers include a stent attached at the end of a wire. The stent is deployed into the vasculature and into the clot, expanded into the clot, and, after a typical waiting time of 0.5 to 10 minutes, extracted to pull the clot out of the blood vessel. Due to non-optimal grabbing of the clot by the stent-retriever, some parts of the clot may be left by or be lost from the retriever, such that several succession treatments (an average 3 times) may be necessary to treat the blockage and restore circulation in the vessel. Each repetition increases injury to the vessel wall and increases both the intervention duration and the duration of impeded blood flow due to the blockage, potentially leading to irreparable damage of the animal. The physio-mechanical process of clot grabbing is currently poorly understood, but the two most common explanations for non-optimal grabbing of a clot are (1) the stent-retriever never deploys into the blood clot and only friction induced by the stent-retriever pushing the blood clot against the wall is responsible for the retrieval of the clot, and (2) the stent deploys into the blood clot but an insufficient amount of time was provided for the stent to coalesce with the blood clot.

If an aspiration catheter is used to remove the blood clot, a clinician inserts the catheter into the vasculature and operates the catheter to aspirate the clot into the catheter. Depending on the diameter of the catheter, it may be placed in direct contact with the clot or placed in a proximal region of the vessel. Depending on the composition and viscosity of the clot, the aspiration method may differ. Some difficulties may arise with aspiration catheters. For example once the clot is aspirated into the catheter, it can block the flow inside the catheter. In such situations, a clinician may not be aware without extraction of the catheter whether the clot is blocking a tip of the catheter or is inside the catheter and blocking a tube. If the clot is blocking the tip of the catheter, there is a risk the clot may be inadvertently released during removal of the catheter, such that the clot may become an embolism that travels through the blood stream and blocks a vessel in another part of the animal.

SUMMARY

Embodiments described relate to techniques for identifying and characterizing biological structures using machine learning techniques. These techniques may be employed to enable a device to identify the particular type of tissue and/or cells (e.g., platelets, smooth muscle cells, or endothelial cells) in, for example, a biological structure, which may be a tissue or a lesion of a duct (e.g., vasculature) in an animal (e.g., a human or non-human animal), among other structures. The machine learning techniques may use raw impedance spectroscopy measurement data in addition to values derived from that raw data. In addition, the machine learning techniques may be used to select frequencies at which to measure impedance and select features to extract from the measured impedance at the selected frequencies to arrive at a small set of frequencies that allow for reliable differentiation.

In one embodiment, a method of training a system to identify at least one characteristic of a biological structure is provided. In some embodiments, the method comprises receiving training data including a plurality of sets of impedance measurements for the biological structure, identifying a first subset of the training data including a first subset of impedance measurements from each set of the plurality of sets of impedance measurements, identifying a first plurality of features from the identified first subset of the training data, the first plurality of features including at least one derived feature that is derived from the identified first subset of the training data, and training a model using at least one machine learning technique with the first plurality of identified features to create a first trained model.

Embodiments described relate to a medical device including an invasive probe that, when inserted into an animal (e.g., a human or non-human animal, including a human or non-human mammal), may aid in diagnosing and/or treating a lesion (e.g., a growth or deposit within a duct such as a vasculature that fully or partially blocks the duct). The invasive probe may have one or more sensors to sense characteristics of the lesion, including by detecting one or more characteristics of tissues and/or biological materials of the lesion. The medical device may be configured to analyze the characteristics of a lesion and, based on the analysis, provide treatment recommendations to a clinician. Such treatment recommendations may include a manner in which to treat a lesion, such as which treatment to use to treat a lesion and/or a manner in which to use a treatment device. The subject matter of the present invention involves, in some cases, interrelated products, alternative solutions to a particular problem, and/or a plurality of different uses of one or more systems and/or articles.

In one embodiment, there is provided a medical device for diagnosis and/or treatment of a lesion of an animal. The medical device comprises an invasive probe for insertion into the animal and removal from the animal following the diagnosis and/or treatment, the invasive probe comprising at least one sensor, at least one processor, and at least one storage medium having encoded thereon executable instructions that, when executed by at least one processor, cause the at least one processor to carry out a method. The method comprises identifying a composition of the lesion using the at least one sensor, wherein identifying the composition of the lesion comprises determining one or more biological materials present in the lesion and identifying at least one characteristic of the lesion based at least in part on the composition.

In certain embodiments, the medical device comprises an invasive probe arranged to be inserted into a duct of an animal during diagnosis and/or treatment of a lesion of the duct and removed from the duct following the diagnosis and/or treatment, the invasive probe being configured to make one or more measurements of the lesion of the duct, the invasive probe comprising at least one impedance sensor and at least one circuit to drive the at least one impedance sensor to make a plurality of measurements of impedance of the lesion, wherein each measurement of the plurality of measurements of impedance corresponds to a frequency of a plurality of frequencies and is a measurement of impedance of the lesion when an electrical signal of the corresponding frequency is applied to the lesion.

Certain aspects are related to inventive methods of operating a medical device for diagnosis and/or treatment of a lesion of an animal. The medical device comprises an invasive probe to be inserted into the animal and removed from the animal following diagnosis and/or treatment of the lesion. The method comprises generating, with the invasive probe of the medical device while the invasive probe is disposed within the animal, a digital signal indicating an impedance spectrum of a plurality of biological materials of the lesion measured by the invasive probe at a plurality of locations of the lesion, wherein generating the digital signal comprises operating the invasive probe to apply an electrical signal at a plurality of frequencies and operating a plurality of sensors of the invasive probe to measure impedance of the plurality of biological materials of the lesion. The method further comprises identifying the lesion based at least in part on an analysis of the digital signal, determining, using at least one processor of the medical device and based at least in part on an analysis of the digital signal and/or an identity of the lesion, one or more treatment recommendations for a manner in which to treat the lesion, and outputting the one or more treatment recommendations for presentation to a user via a user interface.

In a further embodiment, there is provided a method of operating a medical device for diagnosis and/or treatment of a lesion of an animal, the medical device comprising an invasive probe to be inserted into the animal and removed from the animal following the diagnosis and/or treatment of the lesion. The method comprises generating, with the invasive probe of the medical device while the invasive probe is disposed within the animal, data indicating one or more electrical properties of biological materials present in the lesion of the animal, wherein generating the data comprises operating at least one sensor of the invasive probe to measure the one or more electrical properties of the biological materials present in the lesion, and outputting information indicative of the one or more electrical properties, for presentation to a user via a user interface.

In some embodiments, an apparatus is described. In accordance with certain embodiments, the apparatus comprises at least one processor and at least one storage medium having encoded thereon executable instructions that, when executed by the at least one processor, cause the at least one processor to carry out a method comprising receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

At least one storage medium having encoded thereon executable instructions that, when executed by at least one processor, cause the at least one processor to carry out a method is described in accordance with certain embodiments. In some embodiments, the method comprises receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

Certain embodiments describe a method comprising operating at least one processor to carry out acts of: receiving, over time and from a plurality of medical devices, a plurality of reports on medical treatments performed on a plurality of lesions of ducts of animals, each report of the plurality of reports comprising one or more characteristics of a lesion treated in a corresponding medical treatments, one or more parameters of the corresponding medical treatment performed to treat the lesion, and an indication of outcome for the corresponding medical treatment; learning, over time and based on application of a machine learning process to the plurality of reports on medical treatments, one or more relationships between characteristics of lesions and parameters of successful and/or unsuccessful treatments of lesions, wherein learning the one or more relationships comprises determining one or more conditions to associate with each treatment option of a plurality of treatment options, wherein the one or more conditions are related to characteristics of lesions such that, when characteristics of a lesion satisfy the one or more conditions for a corresponding treatment option, the corresponding treatment option is to be recommended for treatment of the lesion; and configuring the plurality of medical devices to make recommendations to clinicians from among the plurality of treatment options based on an evaluation of characteristics of lesions with respect to the one or more conditions associated with each of the plurality of treatment options.

In a further embodiment, there is provided a method of diagnosing and/or treating a lesion of an animal, the method comprising inserting into the animal an invasive probe of a medical device, the invasive probe comprising at least one sensor to measure one or more characteristics of each of a plurality of biological materials of the lesion, identifying the lesion based at least in part on the one or more characteristics of each of the plurality of biological materials of the lesion, operating the medical device to generate one or more recommendations on treatment of the lesion based at least in part on the one or more characteristics of each of the plurality of biological materials and/or an identity of the lesion, treating the lesion in accordance with the one or more recommendations of the medical device on treatment of the lesion, and removing the invasive probe from the duct of the animal.

According to some embodiments, a medical device configured to diagnose and/or treat a lesion of a duct of an animal is described. In certain embodiments, the medical device comprises inserting an invasive probe of the medical device into the duct of the animal, the invasive probe comprising at least one sensor to configured to measure one or more characteristics of a tissue and/or biological material of the lesion; further configured to generate one or more recommendations on treatment of the lesion based at least in part on a measurement of the one or more characteristics by the at least one sensor of the invasive probe; and further configured to deliver a treatment to the lesion in accordance with the one or more recommendations on treatment of the lesion. In certain embodiments, the medical device is also configured to remove the lesion from the duct of the animal.

In one embodiment, there is provided a method of training a system to identify at least one characteristic of a biological structure. The method comprises receiving training data including a plurality of sets of impedance measurements for the biological structure, identifying a first subset of the training data including a first subset of impedance measurements from each set of the plurality of sets of impedance measurements, identifying a first plurality of features from the identified first subset of the training data, the first plurality of features including at least one derived feature that is derived from the identified first subset of the training data, and training a model using at least one machine learning technique with the first plurality of identified features to create a first trained model.

In another embodiment, there is provided a method of training a system to identify at least one characteristic of a biological structure. The method comprises operating at least one processor to carry out an act of selecting a subset of impedance measurements from each of a plurality of sets of impedance measurements for biological structures to produce a plurality of subsets of impedance measurements. Each set of impedance measurements comprises measurements of impedance of one of the biological structures in response to applications of signals of different frequencies. The method further comprises operating the at least one processor to carry out an act of generating a plurality of sets of features. Each set of features characterizes a subset of impedance measurements of the plurality of subsets. Each set of features includes at least one feature present in a subset of impedance measurements and at least one derived feature that is derived from a subset of impedance measurements. The method further comprises operating the at least one processor to carry out an act of training a model to recognize the at least one characteristic of a target biological structure based on input impedance measurements for the target biological structure. The training comprises applying at least one machine learning technique to the plurality of sets of features that characterize the plurality of subsets of impedance measurements to create a trained model.

In a further embodiment, there is provided a method of training a system to identify at least one characteristic of a biological structure. The method comprises operating at least one processor to carry out an act of training a first model using a plurality of sets of impedance measurements and, for each set of impedance measurements, an indication of a biological structure to which the set of impedance measurements corresponds. The plurality of sets of impedance measurements include impedance measurements for a plurality of types of biological structures. The training comprises training the first model, based at least in part on the impedance measurements, to differentiate impedance measurements for a first type of biological structure from impedance measurements for one or more other types of biological structures. The training comprises applying at least one machine learning technique. The method further comprises operating the at least one processor to carry out an act of training a second model, at least in part by applying at least one machine learning technique to impedance measurements for the first type of biological structure, to identify the at least one characteristic of the first type of biological material.

In another embodiment, there is provided a method of determining at least one characteristic of a biological structure. The method comprises operating at least one processor to carry out an act of evaluating impedance measurements for the biological structure using at least one trained model to determine the at least one characteristic. The at least one trained model is trained to distinguish between biological structures having different characteristics.

In a further embodiment, there is provided a method of determining a manner in which to treat a lesion of an animal. The method comprising operating at least one processor to carry out an act of evaluating impedance measurements for the lesion using at least one trained model to determine the manner in which to treat the lesion. Evaluating the impedance measurements comprises evaluating one or more features of the impedance measurements using the at least one trained model. The one or more features comprise at least one derived feature that is derived from the impedance measurements.

In another embodiment, there is provided a method of training a system to identify a manner in which to treat a biological structure. The method comprises receiving training data including a plurality of sets of impedance measurements for the biological structure, identifying a first subset of the training data including a first subset of impedance measurements from each set of the plurality of sets of impedance measurements, identifying a first plurality of features from the identified first subset of the training data, the first plurality of features including at least one derived feature that is derived from the identified first subset of the training data, and training a model using at least one machine learning technique with the first plurality of identified features to create a first trained model.

In a further embodiment, there is provided a method of training a system to identify a manner in which to treat a biological structure. The method comprises operating at least one processor to carry out an act of selecting a subset of impedance measurements from each of a plurality of sets of impedance measurements for biological structures to produce a plurality of subsets of impedance measurements. Each set of impedance measurements comprising measurements of impedance of one of the biological structures in response to applications of signals of different frequencies. The method further comprises operating the at least one processor to carry out an act of generating a plurality of sets of features. Each set of features characterizes a subset of impedance measurements of the plurality of subsets. Each set of features includes at least one feature present in a subset of impedance measurements and at least one derived feature that is derived from a subset of impedance measurements. The method further comprises operating the at least one processor to carry out an act of training a model to determine, from input impedance measurements for the target biological structure, a treatment to recommend for a target biological structure from among a plurality of treatment options. The training comprises applying at least one machine learning technique to the plurality of sets of features that characterize the plurality of subsets of impedance measurements to create a trained model.

In another embodiment, there is provided a method of training a system to identify a manner in which to treat a biological structure, the method comprising operating at least one processor to carry out an act of training a first model using a plurality of sets of impedance measurements and, for each set of impedance measurements, an indication of a biological structure to which the set of impedance measurements corresponds. The plurality of sets of impedance measurements include impedance measurements for a plurality of types of biological structures. The training comprises training the first model, based at least in part on the impedance measurements, to differentiate impedance measurements for a first type of biological structure from impedance measurements for one or more other types of biological structures. The training comprising applying at least one machine learning technique. The method further comprises operating the at least one processor to carry out an act of training a second model, at least in part by applying at least one machine learning technique to impedance measurements for the first type of biological structure, to determine a treatment to recommend for a target biological structure that is of the first type, from among a plurality of treatment options.

In a further embodiment, there is provided at least one storage medium having encoded thereon executable instructions that, when executed by at least one processor, cause the at least one processor to carry out any of the foregoing methods.

In another embodiment, there is provided an apparatus comprising at least one processor and at least one storage medium having encoded thereon executable instructions that, when executed by the at least one processor, cause the at least one processor to carry out any of the foregoing methods.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. The foregoing is thus a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 23 is an example confusion matrix resulting from the application of training data to a trained model created by the process shown in FIG. 22;

FIG. 24-24A are examples of confusion matrices resulting from the application of test data to a trained model created by the process shown in FIG. 22;

Figure 1:
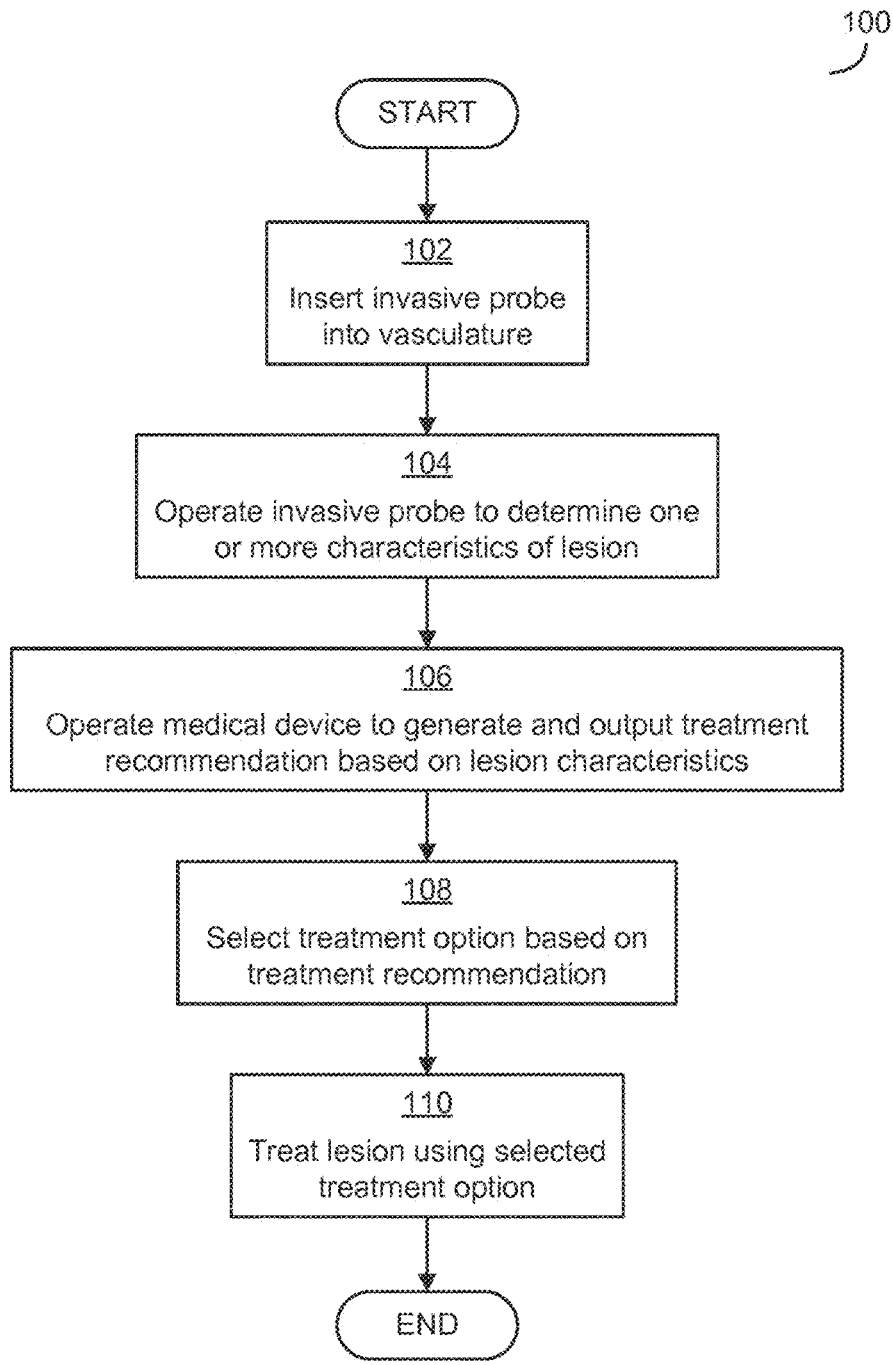
FIG. 1 is a flowchart of a manner in which a clinician may operate a medical device to diagnose and/or treat a lesion, in accordance with embodiments described herein.

The application file of U.S. Provisional application 62/424,693, to which the present application claims priority, contains at least one of the above drawings executed in color. Copies of the color drawing(s) will be provided by the U.S. Patent and Trademark Office upon request and payment of the necessary fee.

DETAILED DESCRIPTION

Some embodiments described herein relate to a medical device including an invasive probe that, when implanted or inserted into an animal (e.g., a human or non-human animal, including a human or non-human mammal), may aid in diagnosing and/or treating a lesion of the animal. The lesion may be an abnormality in the biological structure of the animal, such as a deviation from a normal structure and/or function of a part of an animal, such as an abnormality associated with injury, a medical condition, or a disease. The lesion may appear in different parts of the animal, for example it may be included within a duct of the animal. A lesion of a duct may, for example, act as a blockage that fully or partially blocks the duct. The duct may be, for example, a blood vessel of the animal or other duct and the lesion may be formed, in whole or in part, by a growth in the duct, an accumulation of material in the duct, and/or any other cause of a lesion. The invasive probe may have one or more sensors to sense characteristics of the lesion, which may include detecting a composition of the lesion.

In some embodiments, detecting a composition of a lesion may include identifying one or more biological materials of the lesion, including one or more cells and/or one or more tissues present in the lesion, and/or one or more plaque materials present in the lesion. The biological materials of the lesion that are identified may be all biological materials present in the lesion, or only some of the biological materials present in the lesion. Where only some of the biological materials are identified, the identified material(s) may be only those materials of a certain type of material, such as tissues/cells of the lesion (as compared to other materials, such as plaque materials) or a particular type of tissues/cells (e.g., red blood cells present in the lesion, and not other types of cells). In cases in which a composition is determined and in which only one or some type(s) of biological materials are identified, determining the composition may include determining the amount(s) of the identified material(s) in the lesion, such as determining the amount(s) of the identified material(s) relative to the total materials of the lesion, including by calculating a ratio of one or more of the identified material(s) to the total materials of the lesion.

In some such embodiments, the invasive probe may identify and/or categorize the lesion. Identifying or categorizing the lesion may include, in some embodiments, diagnosing the lesion. The medical device may be configured to analyze the lesion and, based on the analysis, provide treatment recommendations to a clinician. Such treatment recommendations may include a manner in which to treat the lesion, such as which treatment or combination of treatments to use to treat the lesion (e.g., if the lesion is to be removed, whether to use an aspiration catheter or a stent-retriever) and/or a manner in which to use a treatment device (e.g., how fast to extract a stent-retriever). In some such embodiments, the invasive probe may perform such identifying or categorizing, and/or generate such treatment recommendations, based at least in part on the composition of the lesion (e.g., the identity of one or more biological materials of the lesion) and/or one or more other characteristics of the lesion as a whole. For example, a system including the invasive probe and/or other associated devices described below may identify biological materials of a lesion and, based on the identified materials, identify the type of or otherwise categorize the lesion. Based on the identification of the lesion, the system may generate recommendations for treatment of the particular type of lesion. As another example, in other embodiments, the system may identify biological materials of a lesion and, based on the identified materials (alone, or relative to other material(s) of the lesion), generate recommendations for treatment of the lesion. As another example, in other embodiments, the system may, based on information characterizing the biological materials (e.g., impedance spectra) of the lesion, generate recommendations for treatment of the lesion.

Embodiments additionally or alternatively relate to techniques for identifying and characterizing biological structures using machine learning techniques. These techniques may be employed to enable a device to identify the particular type of tissue and/or cells (e.g., platelets, smooth muscle cells, or endothelial cells) in, for example, a biological structure, which may be a tissue or a lesion of a duct (e.g., vasculature) in an animal (e.g., a human or non-human animal), among other structures. The machine learning techniques may use raw impedance spectroscopy measurement data in addition to values derived from that raw data. In addition, the machine learning techniques may be used to select frequencies at which to measure impedance, to arrive at a small set of frequencies that allow for reliable differentiation.

In some embodiments, the invasive probe may include one or a number of sensors, which may include sensors to measure an impedance of the lesion. The sensors may measure impedance of the lesion when electrical signals having particular frequencies are applied to the lesion. The medical device may be configured to, based on the impedance values, determine a composition of the lesion and/or one or more characteristics of the lesion. For example, each sensor may, in some embodiments, be operated to detect an impedance spectrum of a biological material contacting the sensor, such that different sensors of the invasive probe may, at the same time, generate different impedance spectra for different biological materials of the lesion. The medical device may then generate the treatment recommendations based in part on the determined composition. As discussed above, determining the composition may include identifying amounts of one or more biological materials within the lesion, which may be less than all materials of the lesion. For example, in some embodiments, an amount of the lesion that is composed of red blood cells is determined.

Various examples described herein will discuss the medical device in context of vasculature lesions and manners of treating vasculature lesions. It should be appreciated, however, that embodiments are not so limited. Techniques described herein for sensing characteristics of lesions and generating treatment recommendations may be used with any suitable lesion, including with any suitable lesion of an anatomical duct of an animal or lesions that may appear in other locations within an anatomy of an animal. In the case that a lesion is a lesion of a duct, such ducts may include vasculature ducts and gastrointestinal ducts, for example. Those skilled in the art will appreciate that ducts in anatomy differ from anatomical cavities. For example, a duct may be significantly smaller in one dimension (e.g., a width) than in another dimension (e.g., a length).

Thus, in some embodiments, the invasive probe may be a component of a medical device for diagnosis and/or treatment of a lesion of vasculature. For example, the medical device may be a thrombectomy device and the invasive probe may be a component of the thrombectomy device. Accordingly, the invasive probe may be a component of a guide wire, an aspiration catheter, a micro-catheter, a stent-retriever, and/or another thrombectomy device. In some embodiments, a medical device may include two or more of a guide wire, an aspiration catheter, and a stent-retriever and the invasive device may be a component of one or more of these, including all of these.

The inventors have recognized and appreciated that typical conventional techniques for identifying a lesion, including identifying a type of lesion in a duct, based on electrical measurements of a lesion do not have sufficient accuracy or reliability to be effectively used in a medical setting. Some such conventional techniques involve generation of a large number of impedance spectra for whole lesions, for each of a variety of types of lesions, and generating an "average" impedance spectrum for each type of lesion. However, lesions vary greatly from person-to-person, or even within the same person, making it impractical to generate an accurate or representative "average" or "standard" impedance spectrum for a lesion as a whole. Other such conventional techniques attempt to improve reliability by imposing a rigorous measurement process, requiring a precise positioning of sensors contacting a lesion for each measurement during determination of a "standard" spectrum, and the same measurement position during subsequent use on a patient. Such precise positioning is nearly impossible to replicate and reproduce in practice, and still does not improve reliability to the point that these techniques can be used with a sufficient degree of accuracy to be helpful for use with patients. For example, during use with a patient, a measurement of an impedance spectrum of the lesion of the patient would need to be performed, measurement would need to be compared against multiple "standard" spectra for each type of lesion, and computationally-intensive statistical analyses would need to be performed to identify the type of lesion. However, for typical conventional technologies, even these complex analyses yield results with degrees of confidence of only slightly above 50%, at best.

Some embodiments described herein are directed to methods for identifying the type of a lesion, which do not involve the use of databases of "standard" impedance spectra for lesions as a whole, or statistical analyses to compare such whole-lesion impedance spectra. Some of these embodiments are configured to characterize lesions by identifying a composition of the lesion, such as the type and number of some or all of the biological materials that are present in the lesion. This may include identifying one or more tissues and/or cells of the lesion, and/or one or more plaque materials present in the lesion. In some such embodiments, the composition of the lesion may then be analyzed to identify characteristics of the lesion with high degrees of confidence. Such characteristics of the lesion may include a type of the lesion, and the embodiment may include diagnosing the lesion. In some embodiments, the composition of the lesion may be compared to one or more conditions that are associated with types of lesions, such as conditions identifying that a particular type of lesion is associated with a particular composition (e.g., a particular set of biological materials, or particular relative amounts of biological materials). Once a particular composition is determined to have matched a type of lesion by satisfying the condition(s) associated with the type, the lesion having that composition may be identified as being of that type. Identifying the lesion based on an identification of biological materials of the lesion may have high reliability (e.g., greater than 90%).

The inventors have further recognized and appreciated that conventional medical devices, including conventional thrombectomy devices, do not provide information on characteristics of lesions of vasculature including blood vessels, nor do the conventional medical devices provide information on status of treatment of a lesion. The inventors have additionally recognized and appreciated that this lack of information contributes to difficulties of treating lesions. For example, without information on a composition of a lesion, a clinician may have difficulty selecting between available treatment options, as each treatment option may work best for lesions of different compositions. Moreover, without information on a status of a treatment for a lesion, the clinician may not be aware of whether a treatment is being successfully or unsuccessfully performed. Because of this lack of information, multiple treatments may be necessary to correctly treat a lesion. Each such treatment increases risk of injury to a patient and, more importantly for some lesions, increases the duration of lesion. When a vessel is partially or fully blocked by a lesion, the decreased blood flow may cause injury to tissues of the animal.

Accordingly, in accordance with embodiments described herein, a medical device may determine characteristics of a lesion and monitor performance of a treatment, as well as generate recommendations on a manner in which to treat a lesion before and/or during the treatment. This additional information may aid a clinician in initially determining how to treat a lesion, as well as in performing the treatment to try to ensure that, or at least increase a chance that, a lesion is removed with only one treatment and that subsequent treatments are not needed for the same lesion. The medical device may provide information to the clinician in real-time, during a medical intervention, such as by providing real-time information to the clinician on interactions between the medical device and the lesion. Real-time may, in some embodiments, include providing information to the clinician within a time period of corresponding data being sensed by the medical device, where the time period may be less than 5 seconds, less than 10 seconds, less than 30 seconds, less than one minute, or less than 5 minutes, which may be dependent on requirements of an analysis to be performed on data to generate recommendations.

In some embodiments, reliability and effectiveness of techniques and devices may be improved through initialization and configuration, including by configuring a system using a particular approach to selection of data points to be collected, generated, and/or used for a biological structure to be used in characterizing materials of the structure or the structure itself, and/or in generating treatment recommendations. The determination of such data points to be collected may include a determination of frequencies at which to measure an impedance spectrum of biological materials. The determination may additionally or alternatively include determining, once impedance values for frequencies (e.g., a range of frequencies, or any set of selected frequencies) are collected, what features of those impedance values are to be used in subsequent analysis, including identification of which explicit data values within the set of impedance values are to be used or what values are to be derived from an analysis of the data values, for use in subsequent analysis. Some embodiments may include identifying such frequencies and/or features using a machine learning analysis.

Features with which embodiments may operate include descriptors or attributes of data or sets of data, including descriptors or attributes of sets of impedance measurements. A descriptor or attribute of a measurement or a set of measurements may characterize a data point in a data set or the set of data. A feature may have a value, such as a numeric value. When a feature is used to characterize different measurements or data sets of measurements, the feature may be the same descriptor or attribute for the different measurements/sets and thus characterize the measurements/sets in the same or a similar way, but may have different values that correspond to the data points of those different measurements/sets.

Features of the types described herein may include features that are present in a measurement of impedance or a set of measurements of impedance (e.g., an Electrical Impedance Spectroscopy measurements) and/or features derived from an impedance measurement or set. Features present in from measurements of impedance may include numeric values that are explicitly set out within a measurement or a measurement data set. Examples of such features include a magnitude or phase of an impedance measurement or, from among a set of impedance measurements, a minimum or maximum numeric value in the set (where a minimum/maximum may be absolute and/or relative). The minimum or maximum data value may require some analysis, such as a comparison of values, but the minimum/maximum value itself will be a value found within the data set. Derived features may describe a measurement or set, but include a value not found in the measurement/set. Instead, a value of a derived feature may be derived from the measurement/set, such as obtained through performing one or more computations on the measurement/set. Examples of derived features include an average value of the EIS measurements, a phase maximum frequency of the EIS measurements, an n-quantile of the EIS measurements, a first derivative of the EIS measurements, and a second derivative of the EIS measurements, among other.

In some embodiment, the initialization and configuration may include training a filter to distinguish between impedance measurements and/or features that relate to a biological structure of interest, such as a particular type of tissue or a particular type of lesion, and other biological structures. In some scenarios, when impedance measurements are collected for a particular type of lesion, tissue, or other biological structure, one or more of the impedance measurements that are collected may correspond to another biological structure. For example, in some cases a probe that is used to collect impedance measurements for a blood clot or other lesion of a blood vessel may not contact only the blood clot, but may also contact other tissues proximate to the blood clot, such as a vessel wall. These impedance measurements for other tissues or biological structures may hinder proper analysis of the blood clot. The inventors have recognized and appreciated the advantages of training a model, using one or more machine learning techniques, to distinguish between impedance measurements for a biological structure of interest and impedance measurements reflective of other biological structures or reflective of an error in data collection. When a system is to be trained to recognize characteristics of a lesion (or other biological structure of interest) in a part of a body of an animal, one or more other biological structures that may be found in that part of the body or otherwise would be proximate to the lesion may be identified. Impedance measurements may be collected for those other biological structures. Once collected, the impedance measurements may be used, alongside other impedance measurements for the lesion (or other biological structure of interest), to train a model to distinguish between impedance measurements that are for the lesion (or other biological structure of interest) or are for other structures. Once trained, the model may be used to filter input impedance measurements, to prevent or mitigate the chances of impedance measurements for another biological structure interfering with analysis of impedance measurements for the lesion.

It should be appreciated that not all lesions are formed within ducts, and that some embodiments may operate with lesions disposed in areas of the body other than ducts. For example, some cancerous cells may be formed on other parts of an animal (e.g., a human) body. Some embodiments described herein relate to diagnosis and/or treatment of lesions, such as cancerous cells, that are not typically found within ducts. It should be appreciated, however, that some cancerous cells may be found within ducts, and other embodiment described herein relate to diagnosis and/or treatment of such cancerous cells.

It should also be appreciated that while some examples described below relate to lesions, embodiments are not limited to operating with lesions and may operate with any biological structure of interest, having any suitable composition of biological materials.

General Discussion of Techniques

Figure 2:
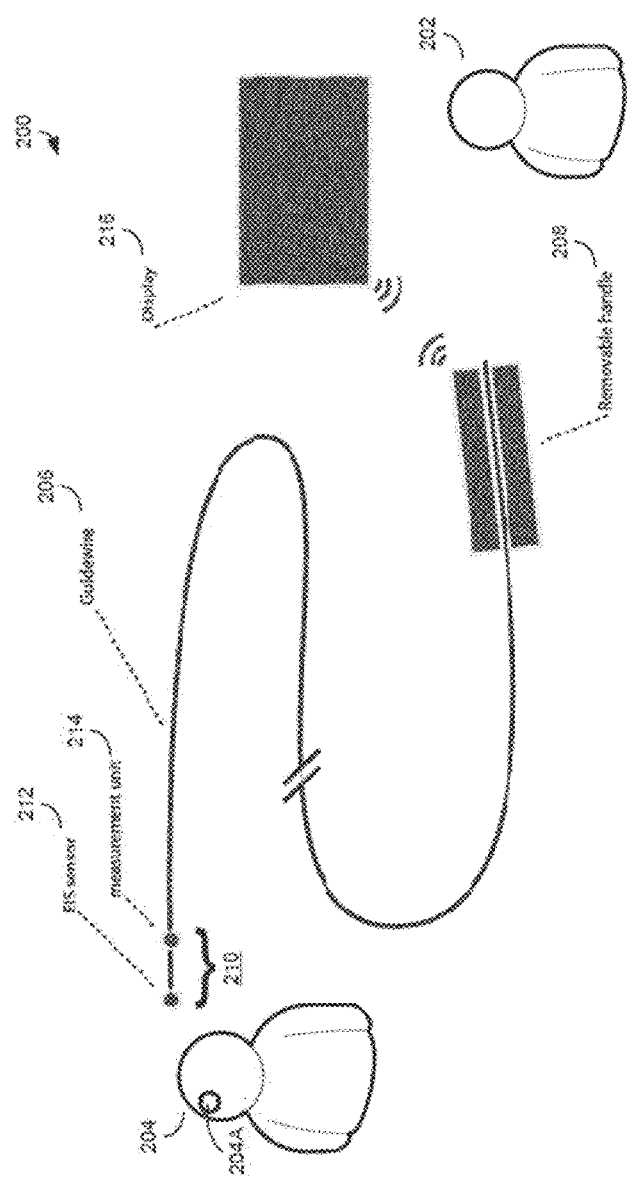
FIG. 2 is an illustration of an example of a medical device in accordance with some embodiments.
Figure 3:
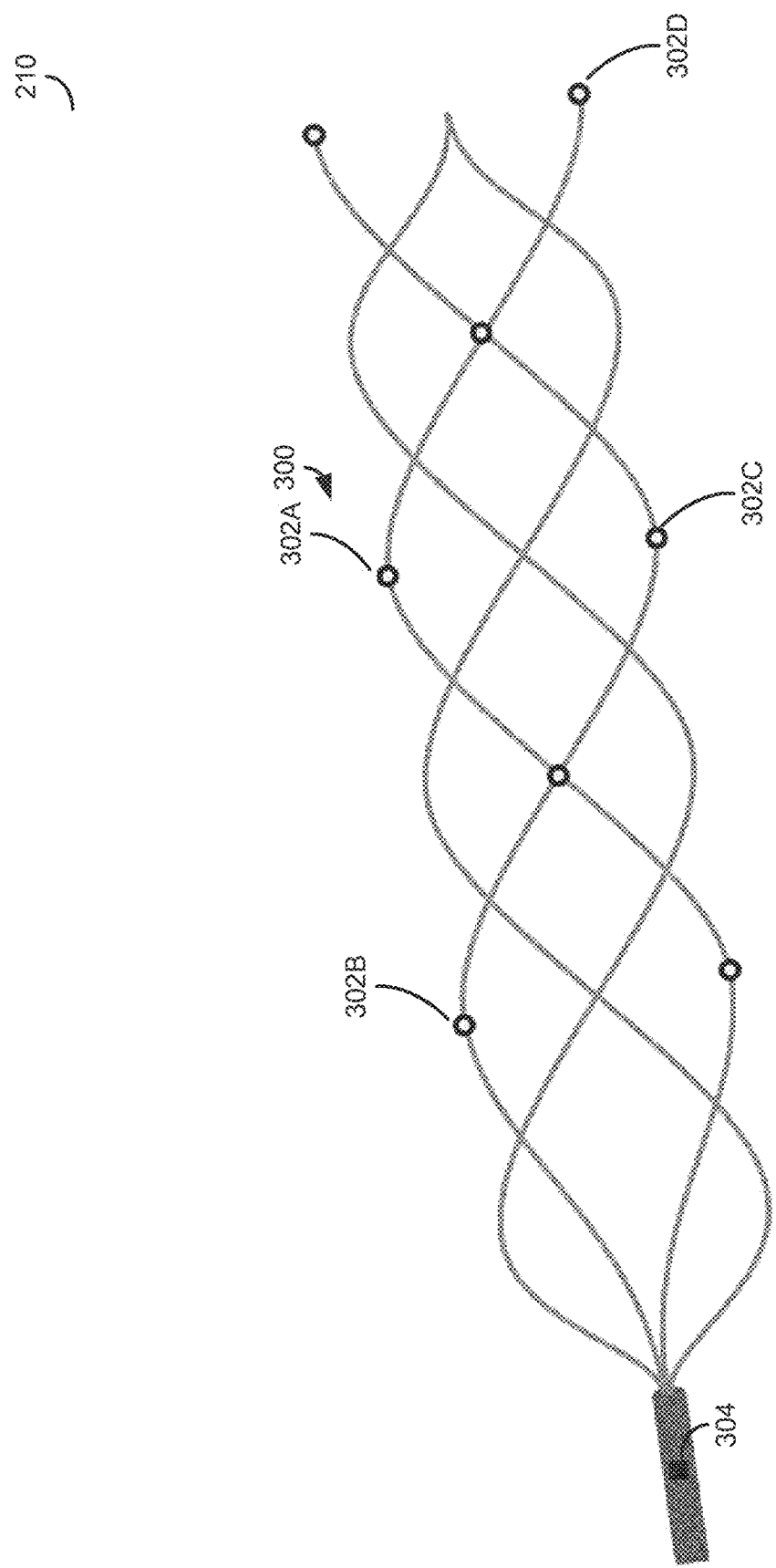
FIG. 3 is an illustration of an example of an invasive probe in accordance with some embodiments.

To provide context for a discussion of exemplary components of a medical device operating in accordance with some embodiments described herein, FIG. 1 is a flowchart of a process that may be followed by a clinician to operate such a medical device. FIGS. 2-3 illustrate examples of a medical device, while other figures below detail other components of a device and ways in which such a device may be operated.

The process 100 may be used to diagnose and/or treat a lesion in subject that is an animal. The animal may be, for example, a human or a non-human animal, including a human or non-human mammal. The lesion may be a lesion within a duct, such as within a blood vessel like a vein or artery of the animal. A duct lesion may be fully or partially blocking the duct. Embodiments described herein may operate with lesions of different characteristics, such as:

in vasculature, a blood clot (including red blood cells, white blood cells, fibrins, thrombi, emboli, and/or platelets) that formed at the site of the lesion or formed elsewhere in the body and became stuck at the site of the lesion;

a growth from the duct wall toward a center of the duct, such as a growth of scar tissue following an injury to endothelial cells at the site of the lesion or other growth;

tissue (e.g., smooth muscle cells, elastic fibers, external elastic membrane, internal elastic member, loose connective tissues, and/or endothelial cells) otherwise extending from a wall of the duct toward a center of the duct that is not anatomically "normal" or "healthy" for that duct at that site;

an accumulation of plaque materials at the site of the lesion, including an accumulation of cholesterol, calcium, fatty substances, cellular waste products, fibrin, and/or other materials that may be found within fluids flowing through a duct of an animal (e.g., substances found within blood of an animal, in the case of a vasculature lesion);

cancerous cells found in ducts such as metastases and/or lymphomas; and/or any other tissues and/or biological materials that may cause a lesion of a duct of an animal.

Lesions of different characteristics may be formed outside ducts. These lesions include cancerous cells such as carcinomas, myelomas, leukemia, lymphoma, melanomas, neoplasms, mixed type and/or sarcomas.

In some embodiments, the histology of a lesion (e.g., which of the biological materials listed above the lesion possesses) may be determined through identifying, based on a plurality of impedance spectra for the lesion, a composition of a lesion, where the composition may indicate biological materials present in the lesion. Such an identification of biological tissues may include identifying tissues and/or cells that are present in the lesion, and/or plaque materials present in the lesion, and/or the relative amounts of such tissues, cells, or plaque materials in the lesion. In some embodiments, identifying the biological materials present in the lesion may include identifying a state of each biological material, such as, for tissues/cells, whether the tissues/cells are healthy or unhealthy. An unhealthy state of a cell may include, for example, whether the cell is inflamed, diseased, cancerous, or otherwise in an abnormal state.

It should be appreciated that embodiments are not limited to operating with lesions of any particular form or composition, or at any particular locations within an anatomy of a subject. As mentioned above, for ease of description, various examples will be provided below in which the duct is vasculature of an animal.

Prior to the start of process 100 of FIG. 1, the subject may exhibit symptoms of a vasculature lesion. An initial determination may be made by a clinician of whether there is a lesion and a potential location of the lesion, such as using imaging techniques like angiography. Based on the symptoms and the initial determination of a location of a lesion, a clinician may choose to insert an invasive device into vasculature of the subject to further diagnose and/or treat the lesion. The clinician may be, for example, a doctor (e.g., a physician or surgeon) or may be another medical professional such as a nurse or medical technician operating the medical device (potentially under a doctor's oversight). In some embodiments, the clinician may be located in the same room as the subject, including next to the subject, while in other embodiments the clinician may be located remote from the subject (e.g., in a different room of the same building as the patient, or geographically remote from the patient) and operating a user interface that controls the medical device via one or more wired and/or wireless networks, including the Internet or other wide area network (WAN).

The process 100 begins in block 102, in which a clinician inserts an invasive probe into vasculature of the subject. The invasive probe inserted by the clinician in block 102 may be located at a distal end of a guide wire for the medical device, and may be shaped, sized, and arranged for insertion into vasculature. In addition, in block 102, the clinician may feed the invasive probe through the subject's vasculature until the invasive probe is located proximate to the lesion. To do so, the clinician may monitor a position of the invasive probe within a subject using imaging techniques, such as using angiography techniques. The insertion and feeding of the invasive probe in block 102 may be performed using suitable techniques for insertion of devices into vasculature, including using known techniques, as embodiments are not limited in this manner.

In block 104, the clinician operates the invasive probe to determine one or more characteristics of the lesion. A characteristic may include a phenotype and/or genotype of a biological structure like a lesion, including a property that distinguishes between biological structures or distinguishes between phenotypes of biological structures. A characteristic may be a property that impacts treatment of the lesion (or other biological structure), as lesions having the property may be treated from lesions not having the property, or lesions having different values for the property may be treated differently. Such properties may be histological, relating to an anatomy of the lesion, and/or anatomical, relating to how the lesion is positioned in or interacts with the body of the animal. A characteristic may therefore describe a lesion. Illustrative characteristics include a location of the lesion, a size of the lesion (e.g., length), a composition of the lesion, or other characteristics discussed in detail below. To determine the characteristics, one or more sensors of the invasive probe may make one or more measurements of tissues and/or other biological materials of the lesion, and/or of tissues/materials otherwise at the site of the lesion such as healthy tissues disposed near the lesion.

In some embodiments, determining one or more characteristics of the lesion may comprise identifying the composition of the lesion, for example by identifying the amount of different type of cells or tissues that are present in the lesion. As one example, it may be identified that a probed lesion is composed of 50% red blood cells, 30% fibrin and 20% platelets.

Examples of sensors and measurements are described in detail below. To operate the invasive probe in block 104, the clinician may contact the lesion with the one or more sensors of the invasive probe, and/or operate a user interface of the medical device to trigger the invasive probe to use the sensor(s) to detect the characteristics of the lesion.

In block 106, the clinician operates the medical device to generate and output treatment recommendations for the lesion based on the determined characteristic(s) of the lesion. As discussed in detail below, the treatment recommendation(s) generated by the medical device based on the characteristic(s) of the lesion may include recommendations on a manner in which to treat a lesion, such as which treatment device to use to treat a lesion (e.g., if material of the lesion is to be removed from the subject, whether to use an aspiration catheter or a stent-retriever) and/or a manner in which to use a treatment device (e.g., how fast to extract a stent-retriever). As also discussed in detail below, the medical device may generate the treatment recommendations based on a variety of analyses, such as by comparing the characteristic(s) of the lesion to conditions associated with each of multiple different treatment options and outputting a recommendation of a treatment option when characteristic(s) of the lesion satisfy corresponding conditions for the treatment option. The output by the medical device may be via any suitable form of user interaction, including a visual, audible, and/or haptic feedback to the clinician via the user interface. In some embodiments, the medical device may in block 106 automatically, without further user intervention, analyze characteristic(s) of the lesion determined in block 104 and generate/output the treatment recommendations. In other embodiments, the clinician may operate the user interface of the medical device to request the analysis and generation/output of the treatment recommendations.

In block 108, the clinician considers the treatment recommendations of the medical device and selects a treatment option and, in block 110, treats the lesion using the selected treatment option.

In some embodiments, the selected treatment option may include insertion of additional invasive medical components into vasculature of the subject. If the invasive probe inserted in block 102 was a component of a guide wire, for example, an additional treatment device may be inserted along the guide wire. As a specific example of such a case, if the medical device recommends full or partial removal of the lesion using a stent-retriever, a stent-retriever may be inserted into the vasculature. As another example, if the medical device recommends removal instead with an aspiration catheter, the clinician may insert an aspiration catheter into the vasculature. As a further example, if the medical device recommends implantation of a stent, a stent implanter may be inserted into the vasculature.

In other embodiments, the treatment may not require insertion of another device. For example, the invasive probe inserted in block 102 may not be a component of a guide wire, but may instead be a component of treatment device such as a stent-retriever. In such a case, the treatment of block 110 may be performed using the treatment device that was inserted in block 102. For example, if the invasive probe inserted in block 102 is a component of a stent retriever, the treatment recommendation of block 106 may be specific to a manner of operating a stent-retriever, such as an amount to expand the stent, an amount of time to wait for a clot to coalesce with the stent, and/or a force or speed with which to withdraw the stent and clot. In such an embodiment, in block 110, the clinician may treat the lesion by operating the stent-retriever as recommended by the medical device in block 106.

In some embodiments, a treatment recommendation may be generated that includes not treating the lesion, but rather treating a subject in a manner that leaves the lesion intact. For example, some types of vascular lesions may be difficult to effectively treat, preventing recanalization of the vessel that is occluded by the lesion. For example, lesions reflective of intracranial artherosclerotic disease (ICAD lesions) may be difficult to remove given treatments currently available. In some embodiments, then, until an effective ICAD treatment is available, if an ICAD lesion is detected, the medical device may generate a treatment recommendation that is to not treat the lesion. An ICAD lesion may be identified by its composition and, in particular, location of biological materials within the lesion. For example, if the medical device determines, through techniques described herein, that a vascular lesion includes a clot on the luminal side of the invasive probe and atherosclerotic plaque materials (e.g., lipidic or calcified components, smooth muscle cells, absence of endothelium) on the abluminal side of the probe, the medical device may determine that the lesion is an ICAD lesion.

Once the lesion is treated in block 110, the process 100 ends. Additional actions that may be taken in some embodiments following treatment of a lesion are described below.

Examples of Medical Devices

As discussed above, FIG. 1 provided a general discussion of a manner in which a medical device may be operated in accordance with some embodiments described herein to diagnose and/or treat a lesion in vasculature of an animal. FIGS. 2-3 provide examples of some embodiments of a medical device that includes an invasive probe that may be inserted into vasculature as part of such diagnosis and/or treatment.

FIG. 2 illustrates a medical device 200 that may be operated by a clinician 202 to diagnose and/or treat a medical condition of a subject 204. The medical condition of the animal 204 (e.g., a human) may be a lesion 204A of vasculature, illustrated in the example of FIG. 2 as a lesion within a cranial blood vessel of a human, which may cause an ischemic stroke. As discussed above, the lesion 204A may be a blood clot, accumulation of plaque materials, excessive growth of smooth muscle tissue, and/or other lesion of a blood vessel.

The medical device 200 as illustrated in FIG. 2 includes a guidewire 206, a handle 208, and an invasive probe 210. The invasive probe 210 and at least some of the guidewire 206 may be inserted into vasculature of the subject 204 until the invasive probe 210 is located proximate to the lesion 204A. The invasive probe 210 may therefore be shaped and otherwise arranged for insertion into the vasculature (or other duct). In some embodiments, the invasive probe 210 will be attached to a guidewire that is approximately 300 micrometers, or a microcatheter that is approximately 3-10 french in diameter, or another device having a diameter suitable for insertion into a duct of an animal. Such a device may be approximately 1 or 2 meters long in some such embodiments, with the invasive probe 210 located at one end of the guidewire/device, for example within last 5 centimeters of the device.

The invasive probe 210 that is inserted into the subject 204 may include one or more sensors 212 and a measurement unit 214. In some embodiments, the sensor(s) 212 may measure one or more electrical characteristics of the lesion 204A, including by measuring one or more electrical characteristics of tissue and/or biological material of the lesion 204A. The measurement unit 214 may receive data generated by the sensor(s) 212 and may, in some embodiments, generate one or more electrical signals to be applied to the lesion 204A as part of measuring the one or more electrical characteristics.

Examples of sensors 212 are described in detail below. As one specific example, the sensor(s) 212 may be impedance sensors and the measurement unit 214 may drive the sensor(s) 212 to perform Electrical Impedance Spectroscopy (EIS) of the lesion 204A. For example, the measurement unit 214 may include one or more oscillators to produce electrical signals of one or more frequencies, which may be specific frequencies that are selected (and that the oscillators of the measurement unit 214 are configured to produce) for discriminating between different tissues and/or different biological materials, to aid in identifying composition of a lesion 204A, as discussed in detail below. In embodiments that are arranged to test tissues/materials using multiple frequencies, the measurement unit 214 may include multiple oscillators, one oscillator being specific to each frequency to be tested and being arranged to generate a signal of that frequency.

In some embodiments in which the measurement unit 214 generates electrical signals to be applied to the lesion 204A, it may be advantageous for the measurement unit 214 to be included within the invasive probe 210 and inserted into the vasculature of the subject 204. This may place the measurement unit 214 in close proximity to the sensors 212 and lesions 204A, and limit noise in electrical signals applied to the lesion 204A. If the measurement unit 214 were located in the handle 208, for example, electrical signals generated by the measurement unit 214 would travel the length of the guidewire 206 before being output by the invasive probe 210 to be applied to the lesion 204A. If the signals were to travel the length of the guidewire 206, electrical noise may affect signal quality. By positioning the measurement unit 214 within the invasive probe 210, noise in the signals may be limited. When the measurement unit 214 is positioned within the invasive probe 210, it may be positioned within a lumen of the invasive probe 210, on a surface (interior or exterior) of the invasive probe 210, or embedded in a film affixed to a surface (interior or exterior) of the invasive probe 210.

The measurement unit 214 may, in some embodiments, be arranged as an Application Specific Integrated Circuit (ASIC). In some such embodiments, the ASIC may be manufactured using packaging processes that reduce silicon substrate layers. For example, during manufacturing, an integrated circuit may be manufactured with "active" silicon layers that include functional components on top of silicon substrate layers that do not include active components. The substrate layer may be the bottommost layer in the stack of layers, and in some cases may be the thickest layer. Conventionally, the substrate layers are left intact following manufacturing, to lend structural stability to the integrated circuit. In some embodiments, the measurement circuit 214 may be manufactured using a process that includes removing silicon substrate layer following manufacture of the active layer and before packaging. The manufacturing process may include removing the substrate from the bottom surface of the wafer, which may be a side opposite from the side on which the active components were manufactured. In some embodiments, all of the silicon substrate may be removed. In other embodiments, substantially all of the silicon substrate may be removed, where "substantially" removed includes leaving only enough silicon substrate to ensure proper electrical functioning of the active layer components, without leaving silicon substrate solely for structural support. After removal of the silicon substrate, the integrated circuit may be encased in a packaging material.

In some embodiments, placing the measurement unit 214 in close proximity to the sensors 212 and lesions 204A may limit the distance traveled by the electrical signals thus reducing signal attenuation. The reduction in signal attenuation may be particularly significant at higher frequencies, since electrical wires tend to exhibit low-pass frequency response. By reducing the distance traveled by the signals, the cut-off frequency of the electrical path between the signal source and the lesions may be increased, thereby increasing the range of frequencies that can be used in a diagnosis or a treatment. As a result, the ability to differentiate types of tissues or cells can be significantly enhanced. Placing the measurement unit 214 in close proximity to the sensors 212 and lesions 204A may increase the cut-off frequency up to 1 MHz in some embodiments, up to 10 MHz in other embodiments, or up to 25 MHz in yet other embodiments. For comparison, when measurement unit 214 is located in the handle 208, the cut-off frequency may be limited to less than 500 KHz.

It should be appreciated that embodiments are not limited to the sensor(s) 212 being EIS sensors or being driven to perform EIS operations. In some embodiments, the sensor(s) 212 may be or include one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors. These sensors may include known, commercially-available sensors.

In some embodiments, the measurement unit 214 included in the invasive device 210 may be configured to drive the sensors 212 and/or process results from the sensors to generate data to be sent back along the guidewire 206 to the handle 208. This may be the case, for example, in embodiments in which treatment recommendations are to be generated by the medical device 200. Data indicative of characteristic(s) of a lesion 204A may be transmitted along the length of the guidewire 206. To limit effects of noise during such a transmission, in some embodiments the measurement unit 214 may include an analog-to-digital converter (ADC) or other component to generate digital data for transmission via a communication channel (e.g., one or more wires) running through the guidewire 206.

In accordance with embodiments described herein, the clinician 202 may treat the lesion 204A in accordance with one or more treatment recommendations generated by the medical device 200. While not illustrated in FIG. 2, the medical device 200 may include a controller to generate and output such treatment recommendations for treatment of the lesion 204A. The controller may, in some embodiments, be implemented as a lesion analysis facility, implemented as executable code that is to be executed by at least one processor of the medical device 200. The lesion analysis facility may analyze characteristic(s) of the lesion 204A determined by the medical device 200 (e.g., by invasive probe 210) in connection with configured information regarding one or more treatment recommendations. As one specific example, discussed in detail below, the lesion analysis facility may compare the characteristic(s) of the lesion 204A to conditions associated with various treatment recommendations and output a treatment recommendation when the characteristic(s) satisfy the condition(s) for that treatment recommendation.

In some embodiments, the processor to execute the lesion analysis facility and the storage medium (e.g., memory) storing the lesion analysis facility and the configured information for the treatment recommendations may be disposed within the handle 208. The lesion analysis facility executing on the processor(s) in the handle 208 may therefore receive from the measurement unit 214, via the communication channel of the guidewire 206, data indicative of one or more characteristics of the lesion 204A.

In other embodiments, however, the processor to execute the lesion analysis facility and the storage medium (e.g., memory) storing the lesion analysis facility and the configured information for the treatment recommendations may be disposed separate from the guidewire 206 and handle 208, such as by being disposed in a separate computing device.

The computing device may be located proximate to the guidewire 206 and handle 208, such as by being located within the same room. The computing device may alternatively be located remote from the guidewire 206 and handle 208, such as by being located in a different room of the same building or geographically remote from the guidewire 206 and handle 208. In embodiments in which the processor/medium are separate from the guidewire 206 and handle 208, the computing device may receive the data indicative of the one or more characteristics of the lesion 204A via one or more wired and/or wireless communication networks, including a direct wire from the handle 208 to the computing device, a Wireless Personal Area Network (WPAN) between the handle 208 and the computing device, a Wireless Local Area Network (WLAN) between the handle 208 and the computing device, a Wireless Wide Area Network (WWAN) between the handle 208 and the computing device, and/or the Internet. Accordingly, in some embodiments the handle 208 may include one or more network adapters to communicate via one or more networks.

When treatment recommendations are generated by the medical device 200, the treatment recommendations may be output by the medical device 200, for presentation to the clinician 202 and/or any other user. The output may be via one or more networks to another device and/or to one or more displays, such as display 216, or other form of user interface. In the example of FIG. 2, the lesion analysis facility may execute on a processor disposed within the handle 208 and generate treatment recommendations, and the recommendations may be output via a wireless network adapter of the handle 208 to the display 216 for presentation to the clinician 202. Other forms of user interface may be used, as embodiments are not limited in this respect. Any suitable visual, audible, or haptic feedback may be used. For example, if a treatment recommendation is to recommend between removal of a lesion using either an aspiration catheter or a stent-retriever, the handle 208 may include a light emitting diode (LED) or other visual element for each option, and present the treatment recommendation by illuminating the appropriate LED. As another example, if a treatment recommendation relates to a manner of operating a stent-retriever and is, in particular, a recommendation of when to begin extraction following a waiting time, a signal to begin extraction may be output using a haptic signal provided via a vibration unit incorporated into the handle 208. Those skilled in the art will appreciate that, as with the computing device discussed above, elements of the user interface may be disposed within the handle 208 or separate from (or even remote from) the handle 208.

Power may be provided to the invasive probe 210 via a power cable extending along a length of the guidewire 206. The power cable may connect to a power supply in the handle 208, which may be a battery, an energy harvester, a connection to grid power supply, or other energy source, as embodiments are not limited in this respect.

In some embodiments, the handle 208 may include one or more sensors, not illustrated in FIG. 2. The sensor(s) incorporated in the handle 208 may monitor operation of the medical device 200, to inform a manner in which a treatment was performed by the clinician 202. For example, an accelerometer or other movement sensor may be arranged in the handle 208, to detect movement of the handle 208 that governs movement of the guidewire 206 and invasive probe 210. For example, by monitoring the accelerometer, a determination may be made of whether the clinician 202 performed multiple treatments to remove a lesion (e.g., multiple passes with an aspiration catheter or stent-retriever) or was able to extract the lesion with only a single pass.

In some embodiments, the handle 208 may be removable from the guidewire 206 and may be reusable between operations. Accordingly, while an invasive probe 210 and/or guidewire 206 may be arranged not to be reusable and may instead be arranged to be disposable for hygienic reasons, the handle 208 may be arranged to be removably attached to the guidewire 206 and reused with other guidewires 206 and invasive probes 210. For example, the guidewire 206 and the handle 208 may have complementary interfaces to allow the handle 208 to connect with the guidewire 206 and interface with components of the guidewire 206 (e.g., a communication channel, a power cable) and the invasive probe 210.

The clinician 202 may operate the medical device 200 via a user interface of the medical device, which includes a display 216 and may be at least partially disposed within the handle 208. For example, the handle 208 may enable the clinician 202 to move the guidewire 206, and the invasive probe 210, forward and back within the vasculature and/or trigger operations of the invasive probe 210.

Operations of the invasive probe 210 may depend on components of the invasive probe 210. For example, the invasive probe 210 may include the sensor(s) 212 to sense one or more characteristics of the lesion 204A. The invasive probe 210 may additionally include the measurement unit 214 to operate the sensors to detect the one or more characteristics, such as by operating the one or more sensors to apply an electrical signal to the lesion 204A and make one or more measurements of the lesion 204A during and/or following application of the electrical signal. In some embodiments, the invasive probe 210 may include one or more components to treat a lesion 204A, including by implanting a stent and/or by removing the lesion 204A. Lesion removal components may include those related to any suitable techniques for removal of lesions, as embodiments are not limited in this respect. In some embodiments, for example, an invasive probe 210 may include stent-retriever components (e.g., a balloon) to perform a lesion retrieval using a stent, and/or aspiration catheter components to aspirate a lesion into a catheter. The invasive probe 210 may additionally include other sensors not shown in FIG. 2, including, for example, optical coherence tomography (OCT) sensors.

The user interface of the medical device, which may be incorporated in whole or in part in the handle 208, may therefore enable the clinician 202 to perform a number of different operations with the invasive probe 210. For example, a user interface of the handle 208 may enable the clinician 202 to trigger sensors 212 and measurement unit 214 to apply an electrical signal and/or make a measurement of the lesion 204A, and/or to perform one or more treatment operations to treat the lesion 204A.

While an example has been described in which medical device 200 may include treatment components to perform one or more operations to treat a lesion 204A, it should be appreciated that embodiments are not so limited. In some embodiments, medical device 200 may be a guide wire for additional treatment devices that are inserted along the guide wire to be positioned proximate to the lesion 204A and to treat the lesion 204A. For example, after insertion of the invasive probe 210 and guidewire 206, the clinician 202 may insert another device along the length of the guidewire 206, or may remove the guidewire 206 and invasive probe 210 and then insert a new device. The newly-inserted device may be, for example, a stent implanter, an aspiration catheter, a stent-retriever, or other device to treat the lesion 204A. In some embodiments in which an additional device is inserted, the handle 208 may be compatible with the additional device, such that the additional device and the handle 208 may have compatible interfaces and a user interface of the handle 208 may be used to operate the additional device.

In addition, while an example has been provided in which a clinician 202 manually operates the medical device 200 in accordance with treatment recommendations, embodiments are not so limited. In alternative embodiments, the medical device 200 may treat a lesion automatically, based on input from sensors 212. For example, as should be appreciated from the brief discussion above and the detailed discussion below, the medical device 200 may generate treatment recommendations on a manner in which to treat the lesion 204A. In some embodiments, the medical device 200, in accordance with the treatment recommendations and without user intervention (though, in some embodiments, under supervision of a clinician 202) insert and/or operate an aspiration catheter, stent-retriever, stent implanter or other device to treat the lesion 204A in accordance with the treatment recommendations.

It should be appreciated that embodiments are not limited to operating with medical devices that are invasive or include an invasive component that is inserted within the body of an animal. For example, non-invasive probes may have measurement units and/or sensors (such as EIS sensors) that operate as described herein, including operating using frequencies or features selected as described herein or using models trained as described herein. Such non-invasive devices may be, for example, used for diagnosis and/or treatment of skin lesions.

It should also be appreciated that techniques described herein are not limited to use with insertable devices such as a guidewire or other tool that may be inserted and then removed, but may also be used with implantable devices. For example, measurement units and sensors of the types described herein may be used with stents, such as where the sensors are positioned directly on the stent. In this way, monitoring of the tissues in the region where the stent is positioned may be performed once and after the stent is in place. The sensors may sense one or more characteristics (e.g., composition) of the tissues in the region where the stent is placed. The sensed characteristics may be used to infer characteristics of one or more biological structures contacted by the stent, to make determinations regarding the one or more biological structures. For example, the system may be used to determine whether a tissue that the stent is contacting is healthy or whether scar tissue or other non-healthy tissue is forming, or whether an occlusion has formed.

FIG. 3 illustrates an example of an invasive probe 210 with which some embodiments may operate. The invasive probe 210 of the example of FIG. 3 includes a mesh 300 that is arranged similarly to a stent. The invasive probe 210 may be operable as a stent-retriever in some embodiments. In other embodiments, the invasive probe 210 may not be operable as a stent-retriever but may include the mesh 300 or another structure to provide multiple points of contact between sensors and a lesion so as to detect characteristics of a lesion with greater accuracy than may be possible using only a single sensor.

Though, it should be appreciated that in some embodiments (not the embodiment of FIG. 3), an invasive probe 210 may include only one sensor, which may be located, for example, at a distal end of the invasive probe 210. Such a sensor may be implemented as two electrodes, one of which may apply an electrical signal to a lesion and one of which may receive the applied signal. Based on a comparison of the applied signal to the received signal, one or more determinations may be made, as discussed in detail below.

The inventors have recognized and appreciated, however, that including additional sensors in the invasive probe 210 may enable more detailed information to be determined. For example, including additional sensors in the invasive probe 210 may enable information on a composition of a lesion to be made with more precision as compared to only a single sensor. Such additional sensors may enable, for example, an impedance spectrum to be determined for each of multiple locations along the invasive probe, such that, in some cases, different impedance spectra may be determined, at different locations, for the same lesion. This may include, for example, determining an impedance spectrum using each sensor. Each impedance spectrum in this case would be the impedance spectrum of a biological material, of the lesion, that a sensor (with its two electrodes) contacts. Some lesions may include multiple different biological materials (e.g., different tissues or cells, or different plaque materials). In a case that each sensor of the invasive probe contacts a different biological material, each sensor may determine a different impedance spectrum, for each different biological material. Though, it may be the case that, for some lesions, two or more sensors of the invasive probe may contact the same biological material and, in such a case, may generate the same or substantially the same impedance spectra. Accordingly, in some embodiments, the invasive probe may operate each sensor to generate an impedance spectrum for a biological material of the lesion. Generating an impedance spectrum for each of multiple biological materials of the lesion (i.e., multiple impedance spectra for each lesion) contrasts with determining a single impedance spectrum for the lesion as a whole. Techniques for determining composition of a lesion using multiple sensors, including through performing EIS, are discussed below.

Accordingly, FIG. 3 illustrates an example of an invasive probe 210 having multiple sensors arranged along an exterior and/or interior surface of the probe 210. The sensors 302 (including sensors 302A, 302B, 302C, 302D, generically or collectively referred to herein as sensor(s) 302) may be arranged along the structure 300. In some embodiments, each sensor may be or include one or more electrodes to apply an electrical signal and/or detect an applied electrical signal.

In some embodiments, while not illustrated in FIG. 3, the invasive probe 210 may include a balloon to, when inflated, expand the structure 300 outward, to better contact a lesion. During use, for example, the structure 300 may be wholly or partially inserted into a lesion, such as until sensors located at a distal end of the structure 300 detect that they have passed to a far side of the lesion, after which the structure 300 may be expanded using the balloon until sensors 302 detect contact at multiple points. The inflation of the structure 300 may be controlled by a controller of the invasive probe 210 (e.g., measurement unit 304) or may be controlled by a lesion analysis facility disposed elsewhere in the medical device and/or by a clinician via a user interface of a medical device.

In some embodiments, a measurement unit 304 may operate the sensors 302 to perform one or more measurements, including by generating one or more electrical signals to apply to a lesion and analyzing data generated by sensors 302. The analysis of the data generated by the sensors 302 may include performing an analog-to-digital conversion of the data to be transmitted along a guidewire to an outside of a patient, such as to a lesion analysis facility or user interface as discussed above.

While examples have been provided in which the sensors 302 are electrical sensors, it should be appreciated that embodiments are not so limited. For example, the sensors 302 may be or include one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors.

Examples of Sensors and Sensing Techniques

As discussed above, in some embodiments a measurement unit of an invasive probe may operate sensors of the invasive probe to perform an Electrical Impedance Spectroscopy (EIS). FIGS. 4-11 describe examples of ways in which such sensors and measurement units may be arranged, and describe examples of techniques for operation of such sensors and measurement units. It should be appreciated, however, that embodiments are not limited to operating in accordance with the examples for EIS described in this section.

The techniques described in this section with regard to FIGS. 4-11 allow for a discrimination of tissues and/or biological materials of a lesion of a duct of an animal, including of a mammal such as a human. "Discrimination" should be understood here to mean the possibility, given by this method, of distinguishing between lesions of different compositions, for example by determining one or more types of cells (e.g., red blood cells and/or white blood cells, or different types or states of endothelial cells) of the lesion and/or one or more types of other biological material (e.g., plaque materials such as cholesterol) of the lesion. More generally, the discrimination made possible by techniques described in this section includes determining at least one item of information relating to a tested lesion. Examples of information that may be determined through these techniques are given later.

Figure 4:
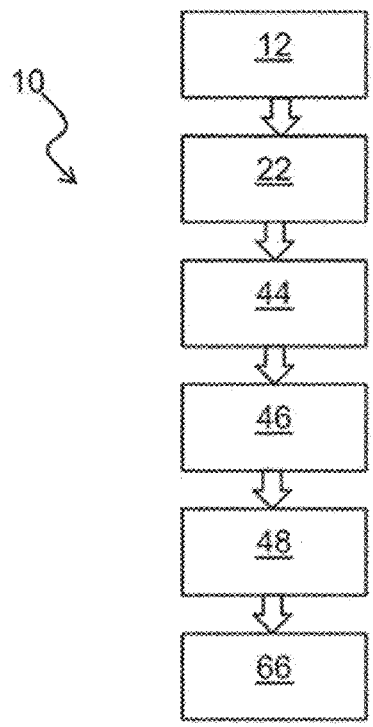
FIGS. 4-5 are flowcharts of processes that may be implemented in some embodiments to determine a composition of a lesion.

The cell discrimination method 10, as illustrated schematically in FIG. 4, comprises a first step 12 of determining a frequency spectrum of the impedance of a lesion that is tested.

Spectrum should be understood here to mean a set of pairs of values of the impedance of the lesion, the latter being able to be complex, and of a corresponding frequency. This spectrum may thus be discrete and comprise only a finite number of pairs. These pairs may notably be separated by several Hz, even by several tens of Hz, even by several hundreds of Hz. However, in other embodiments, the spectrum determined in this step is continuous, pseudo-continuous or discretized, over a frequency band. Pseudo-continuous should be understood to mean that the spectrum is determined for successive frequencies separated by 100 Hz or less, preferably by 10 Hz or less, preferably even by 1 Hz or less. The frequency band over which the impedance of the tissue is determined extends, for example, from 10 kHz, preferably 100 kHz. In effect, at low frequencies, the membrane of the tissue/material of the lesion acts as an electrical insulator, so that the impedance is very high and, above all, varies little. Moreover, the frequency band over which the impedance of the tissue/material of the lesion is determined extends, for example, up to 100 MHz, preferably 1 MHz. In effect, at high frequencies, the wall of the tissue/material that make up the lesion become transparent from an electrical point of view. The measured impedance is therefore no longer representative of the biological material. This spectrum may be a frequency spectrum of the real part and/or of the imaginary part and/or of the modulus and/or of the phase of the complex impedance of the lesion.

Figure 5:
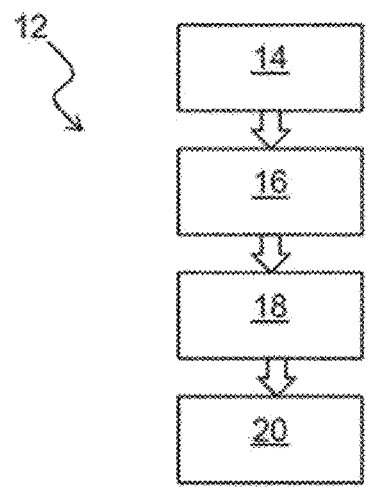

This first step 12 of determination of a frequency spectrum of the impedance of the lesion may notably be performed as described hereinbelow, in connection with FIG. 5.

First of all, during a step 14, two, preferably three, even more preferably four electrodes are placed in contact with the lesion to be tested, the electrodes being linked to an alternating current generator. The measurement with four electrodes is preferred because it makes it possible to implement two electrodes to pass the current into the lesion to be tested and to measure the potential difference between the other two electrodes. This makes it possible to improve the accuracy of the measurement. Then, during a step 16, an alternating current is applied between the electrodes contacting the lesion. Then, by varying the frequency of the current applied during a step 18, the corresponding voltage is measured, at the terminals of the electrodes for different frequencies. Finally, during a step 20, the ratio between the voltage measured and the current applied is calculated, for each of the frequencies for which the measurement has been performed. This ratio gives the impedance of the lesion tested, as a function of the measurement frequency. The calculated ratios make it possible to define a frequency spectrum of the impedance of the lesion.

Figure 6:
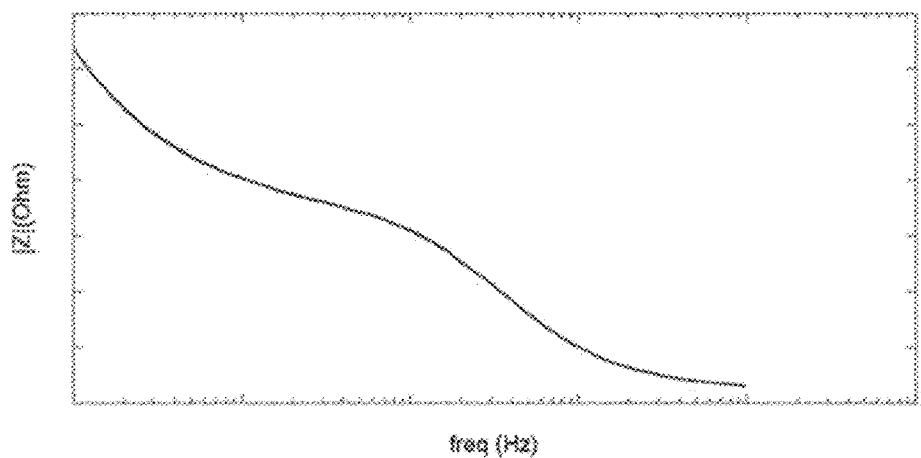
FIG. 6 is a representation of an exemplary frequency spectrum of the modulus of the impedance of a lesion.

When the spectrum is continuous or pseudo-continuous, it may be represented as illustrated in FIG. 6, in the form of a curve giving, in this particular case, the modulus of the impedance of the lesion as a function of the frequency, the latter being plotted according to a logarithm scale. It should be noted here that a logarithmic scale is used on the x axis.

In a step 22 of the discrimination method 10 of FIG. 4, different models of the impedance of the lesion, that is to say different electrical circuits that may model the lesion, are then chosen. Here, models are chosen that include a constant phase element, and not a capacitance. In effect, it has been found that a constant phase element models more realistically the behaviour of the lesion than a capacitance.

A constant phase element (or CPE) has an impedance $Z_{CPE}$ of the form:

$$Z_{CPE} = \frac{1}{(j\omega)^\alpha Q_0} \qquad [1]$$

or:

$$Z_{CPE} = \frac{1}{(j\omega Q_0)^\alpha}, \qquad [2]$$

in which:

j is the square root of $-1 (j^2=-1)$;

$\omega$ is the specific pulsing of the current ($\omega=2\pi f$, in which f is the frequency of the current);

$Q_0$ is a real parameter of the constant phase element; and $\alpha$ is another real parameter of the constant phase element, lying between 0 and 1, such that the phase $\varphi_{CPE}$ of the constant phase element is equal to $-\alpha\pi/2$.

Hereinafter in the description, a constant phase element whose impedance is given by the equation [1] above is chosen by way of example.

The models of the impedance of the lesion may notably be chosen from those described hereinbelow, with respect to FIGS. 7-10. Obviously, the simpler the model, the simpler the calculations. However, a complex model may better correlate to the spectrum of the impedance obtained by the measurement and therefore give more accurate results.

Figure 7:
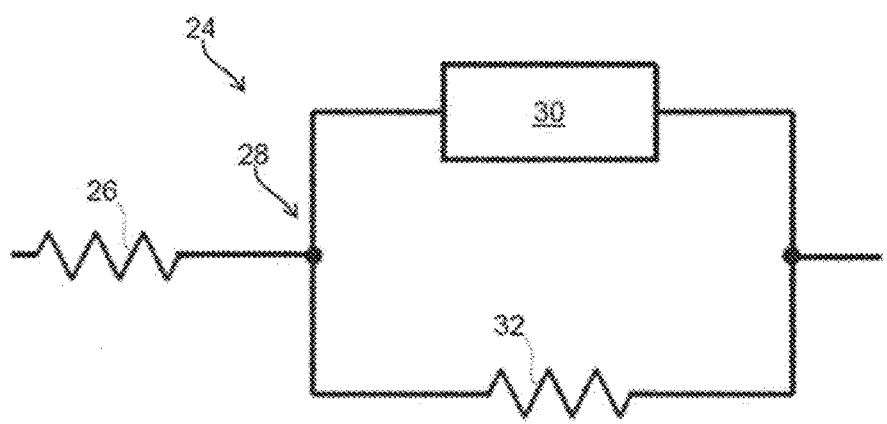
FIGS. 7-10 illustrate exemplary models of the impedance of a lesion, that may be implemented in the method of FIG. 4, including a constant phase element.

According to a first model 24 illustrated in FIG. 7, the impedance of the lesion is modelled by a first resistance 26 mounted in series with a parallel connection 28 of a constant phase element 30 and of a second resistance 32.

In this case, the total resistance $Z_{tot}$ of the lesion is of the form:

$$Z_{tot} = R_1 + \frac{R_2}{1 + (j\omega)^\alpha Q_0 R_2}, \quad [3]$$

in which:
$Z_{tot}$ is the total impedance of the first model 24 representing the lesion;
R1 and R2 are the resistance values of the first 26 and second 32 resistances.

Such a model describes particularly well a lesion covering measurement electrodes, like a set of individual parallel mountings, each individual mounting being made up of an individual resistance in series with a parallel mounting of an individual resistance and of an individual capacitance. Such a mounting makes it possible to model a distribution of the time constant over all of the surface of the measurement electrodes, according to different circuits in parallel whose parameters may be different, each of these circuits in parallel representing different tissue/material of a lesion. Thus, the fact that the tissues/materials of the lesion may exhibit different electrical properties, notably a different resistance and/or capacitance, is modelled.

Figure 8A:
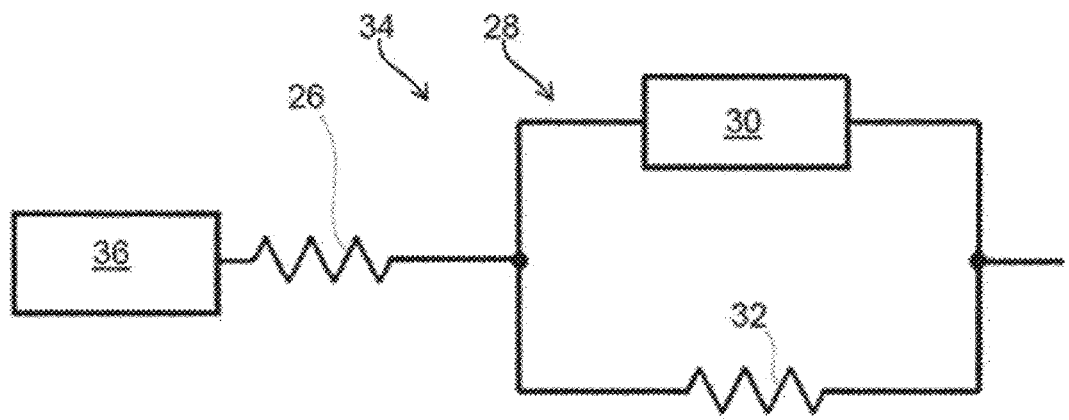

A second model 34, illustrated in FIG. 8A, complements the model 24 of FIG. 7, by the series mounting of a second constant phase element 36. The impedance $Z_{CPE,2}$ of this second constant phase element 36 may also be chosen to be of the form:

$$Z_{CPE,2} = \frac{1}{(j\omega)^\beta Q_1}, \quad [4]$$

in which:
β is a real parameter lying between 0 and 1, such that the constant phase of this second constant phase element is equal to $-\beta\pi/2$; and
$Q_1$ is a real parameter of the constant phase element.

The total impedance $Z_{tot}$ of the lesion according to this second model 34 is therefore given by the following equation:

$$Z_{tot} = \frac{1}{(j\omega)^\beta Q_1} + R_1 + \frac{R_2}{(j\omega Q_0)^\alpha R_2}. \quad [5]$$

Figure 8B:
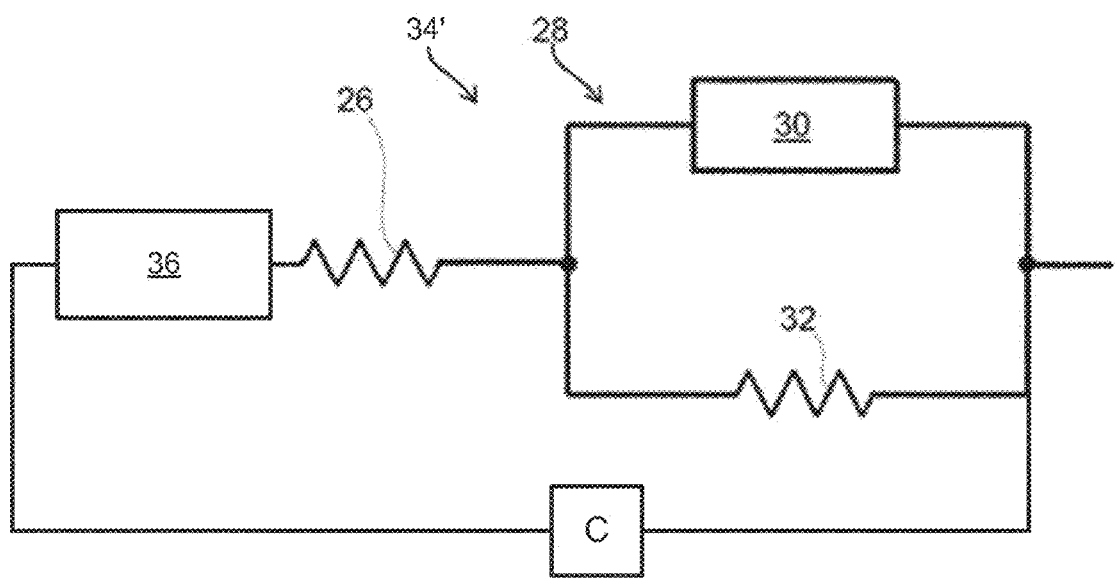

A variant 34' of the second model 34 is shown in FIG. 8B, and differs from the model of FIG. 8A by the addition of a capacitance C in parallel with the circuit of FIG. 8A, for a better fit of the impedance curve at high frequencies.

Figure 9:
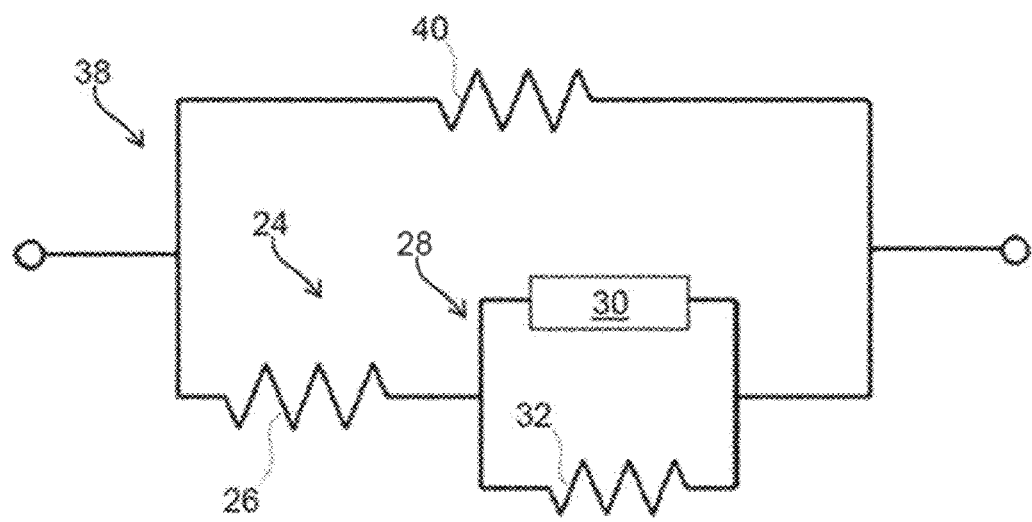

A third model 38, illustrated in FIG. 9, corresponds to the model of FIG. 7, mounted in parallel with a third resistance 40, of resistance $R_3$. In this case, the total impedance $Z_{tot}$ of the lesion is given by the equation:

$$\frac{1}{Z_{tot}} = \frac{1}{R_3} + \frac{1}{R_1 + \frac{R_2}{1 + (j\omega Q_0)^\alpha R_2}}. \quad [6]$$

Figure 10:
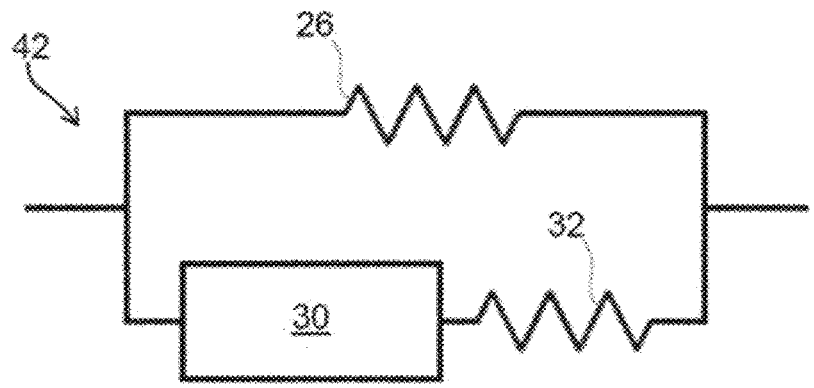

Finally, a fourth exemplary model 42 is illustrated in FIG. 10. This model 42 comprises, as illustrated, a first resistance 26, mounted in parallel with a series mounting of a constant phase element 30 and of a second resistance 32.

The total impedance $Z_{tot}$ of the lesion is given, for this model 42, by the equation:

$$\frac{1}{Z_{tot}} = \frac{1}{R_1} + \frac{R_2}{1 + (j\omega Q_0)^\alpha R_2} \quad [7]$$

The discrimination method then continues with a step 44, during which, for each model chosen in step 22, the impedance of the constant phase element 30 which optimizes the correlation between the model of the impedance of the lesion and the spectrum determined in step 12 is determined.

This step of optimization of the correlation between the model of the impedance of the lesion and the spectrum determined in the step 12 may be implemented by any optimization method known by those skilled in the art. By way of example, the least squares method may be implemented, which allows for a practical and relatively simple implementation of this step 44.

In practice, the other parameters of the different models, other than those of the impedance of the constant phase element, are also determined during this step 44. These elements may also be useful for obtaining information on the lesion tested and/or on the tissues/materials of which it is composed.

An intermediate step 46 of the discrimination method 10 may then be provided. This step 46 consists in determining the model which seems to best correlate with the measured spectrum of the impedance of the lesion. This best model may for example be that which minimizes the standard deviation with the measured spectrum. Hereinafter in the description, the case in which the model 24 is retained as that correlating best to the measured spectrum of the impedance of the lesion is assumed.

During a step 48, an effective capacitance (or apparent capacitance) of the lesion is deduced from the parameters of the impedance of the constant phase element and from the corresponding model.

Theoretically, this effective capacitance is representative of a set of individual capacitances of elements of the cell structure. The effective capacitance is representative of distributed local capacitances of elements of the cell structure. These elements of the cell structure may notably be all or some of the nuclei of the cells of the cellular structure and also other parts of the cells such as the golgi apparatus, vesicles, mitochondrion, lysosome and other elements which may play a role in membrane interaction. The effective capacitance may also be influenced by the geometry of cells and the space between cells. The effective capacitance is a model which allows for a representation of the electrical membrane behaviour of a part or of all of a lesion. This model makes it possible to relevantly discriminate the tissues/materials of a lesion.

More practically, this effective capacitance is determined by identifying the impedance of the lesion with a model comprising individual parallel mountings, each individual mounting comprising at least one individual resistance and one individual capacitance. Each mounting may notably comprise, preferably consist of, a first individual resistance in series with a parallel mounting of an individual capacitance with a second individual resistance. These individual mountings aim to model the behaviour of each tissue/material of the lesion. The effective capacitance is then the capacitance resulting, in the lesion, from the presence of all the individual capacitances.

In the case of the model 24 (or 34 or 34'), the determination of the effective capacitance may notably be performed as follows. The impedance of the model 24 with a constant phase element is compared with the impedance of an equivalent or identical model, in which the constant phase element is replaced by an effective capacitance. The calculation, strictly speaking, of the effective capacitance may then be performed by comparing the real part and/or the imaginary part and/or the phase and/or the modulus of the impedance of the model chosen for the lesion with a constant phase element with the identical model in which the constant phase element is replaced by an effective capacitance.

In the case of the model 24 (or 34 or 34'), for example, by introducing a time constant $$\tau_0 = C_{\mathit{eff}} \frac{R_1 R_2}{R_1 + R_2}$$

into the equation of the admittance of the model 24, directly deduced from the equation [3], the equation [8] below is obtained:

$$Y_{tot} = \frac{1}{R_1}\left[1 - \frac{R_2}{R_1+R_2}\left(1 + \frac{R_1 R_2}{R_1+R_2}Q_0(j\omega)^\alpha\right)^{-1}\right] = \quad [8]$$

$$\frac{1}{R_1}\left[1 - \frac{R_2}{R_1+R_2}(1+(j\omega\tau_0)^\alpha)^{-1}\right],$$

from which a formula for the effective capacitance may be deduced, in the form:

$$C_{\mathit{eff}} = Q_0^{1/\alpha} \times \left(\frac{1}{R_1} + \frac{1}{R_2}\right)^{(\alpha-1)/\alpha} \quad [9]$$

In the case where another model of impedance of the lesion with a constant phase element is chosen, it is possible to determine a corresponding equation of the effective capacitance. To do this, it is sufficient to calculate the impedances $R_1$, $R_2$, $Z_{CPE}$ and $Z_{CPE,2}$, if appropriate, of the model 24 or 34 or 34', as a function of the parameters of the chosen model, for the model 24 or 34 or 34' to be electrically equivalent to the model of the impedance of the lesion. The effective capacitance may then be calculated by replacing $R_1$, $R_2$, $Z_0$ and $\alpha$ with the corresponding values, expressed as a function of the parameters of the chosen model.

The cell discrimination method 10 then continues with a step 66 of deduction of an item of information on the tissues/materials of the lesion, from the effective capacitance determined previously.

This deduction may notably be made by comparing the value of the effective capacitance determined in the step 48 with pre-established values. The pre-established values may notably be obtained during tests performed on tissues of known compositions, in known media, and with known test conditions. The pre-established values may be grouped together in a database of effective capacitance values, grouping together the effective capacitances measured for different types of cells and/or different conditions of different cells and/or in different test conditions. The effective capacitance value may be compared to a database of effective capacitances of cell type and condition susceptible to be found in the present measurement. For the comparison, the effective capacitance $C_{\mathit{eff}}$ may be used together with other parameters. The comparison may not be an exact match and includes the determination whether the effective capacitance value falls or not within a pre-determined range.

It is thus possible to discriminate the tissues/materials of the lesion, that is to say to determine at least one of the following items of information:

the type of tissues and/or other biological materials in the lesion;

the composition of the lesion, notably if the latter is composed of different types of biological materials or of tissues/cells/other biological materials in different states;

when the lesion is composed of tissues, the types of cells included in the tissue and/or the number of layers of cells present in the tissue;

when the lesion is composed of other biological materials, such as plaque materials, the types of materials included in the lesion; and/or the state of cells included in tissues of the lesion, notably if the cells are in a healthy state, in an inflamed state, in a degenerated state, notably if there are one or more cancerous cells, in an infected state.

Figure 18:
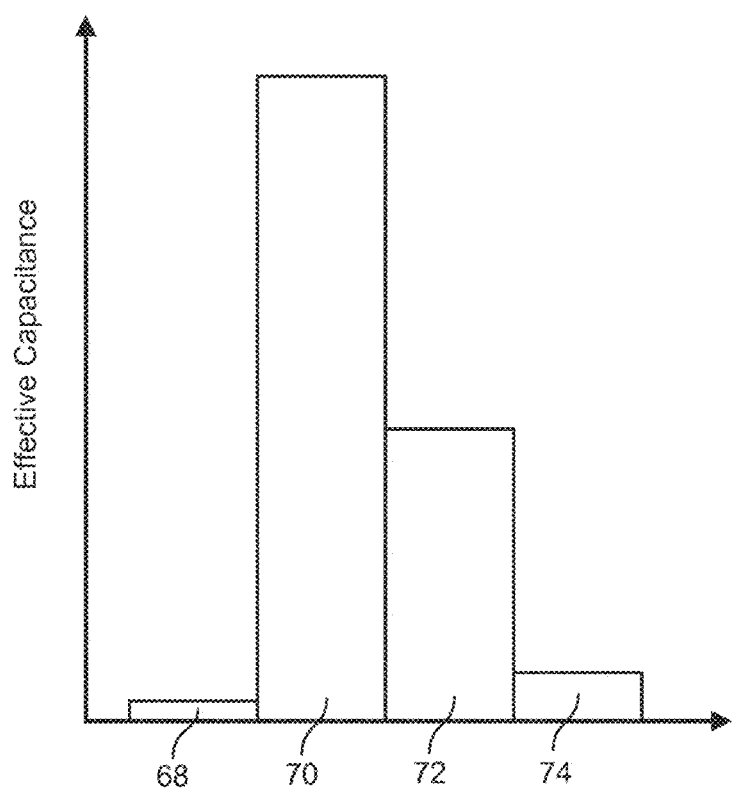
FIG. 18 shows an example, in diagram form, of effective capacitances of cellular structures determined by the method of FIG. 4.

As an example, FIG. 18 represents, in diagram form, the effective capacitances 68, 70, 72, 74 determined in the context of a test conducted according to the method described previously.

In the context of a test, cells were cultivated until the confluence of the cells was obtained. In the case of the exemplary test which was conducted, two days of culture were required in an incubator at 37° C. and 5% CO2, to obtain, by confluence, the tissues to be tested. The determination of the spectrum of the impedance of the different tissues to be tested was performed using an impedance spectroscopy system. The spectrum was determined between 1 kHz and 10 MHz, by applying an alternating voltage estimated to be fairly low so as not to electrically excite the cells being studied, but sufficient to have correct measurements. In the example of the test conducted, an amplitude of 20 mV of the alternating voltage was retained.

The effective capacitance 68 is that of the test medium, static, alone. This test medium is a cell culture medium. The effective capacitance 70 is that of bovine aortic endothelial cells (BAEC). The effective capacitance 72 is that of bovine aortic smooth muscle cells (BAOSMC). Finally, the effective capacitance 74 is that of blood platelets (or thrombocytes). As this diagram shows, the effective capacitances of the different types of cells exhibit values clearly different from one another, which makes it possible to effectively distinguish between the different types of cells with accuracy, without risk of confusion.

Thus, one advantage of the discrimination method described is that it allows for the discrimination of tissues/materials in a lesion contacting the electrodes, from a simple measurement of a frequency spectrum of an impedance of the lesion to be tested. The results obtained are accurate. There is no need to proceed with a normalization of the measured impedance, nor to proceed with a reference measurement in the absence of any sample to be tested. The method may thus be implemented without the need for prior sampling of cells or of a cellular structure to be tested, and may be implemented in vivo in some embodiments.

It should be noted, in the case where an effective capacitance is determined, that this single value is often sufficient to discriminate the tissues/materials of the lesion. The parameters of the chosen model of the impedance of the lesion to be tested may also be compared to pre-established values to specify the result of the comparison of the effective capacitance. For example, when cells of a tissue are inflamed, the junction between the cells is more loose. The resistance at low frequency—that is to say the resistance 32 of the model 24 for example—is then lower, compared to healthy cells. A comparison of the value of this resistance with a value pre-established for healthy, non-inflamed cells may then make it possible to determine the inflamed state of these cells.

It should also be noted that the other parameters of the model may be considered to discriminate the tissues/materials of a lesion. However, these other parameters may also make it possible to determine additional items of information on the lesion tested. Thus, for example, $R_2$ or the sum $R_1+R_2$ of the resistances 26, 32 of the model 24 may be considered to determine the thickness of a cellular structure, when a lesion includes tissues. To do this, the values $R_2$, and possibly $R_1$, are determined, notably concomitantly with the determination of the impedance of the constant phase element, so as to optimize the correlation of the model 24 with the measured impedance spectrum. The value $R_2$ or the sum $R_1+R_2$ may then be compared to corresponding values, predetermined in known conditions, for example in vitro. These predetermined values may notably be stored in a data store.

As stated previously, the method may easily be implemented in the context of devices that may be inserted into an animal subject, such as inserted into vasculature of a human subject.

Figure 11:
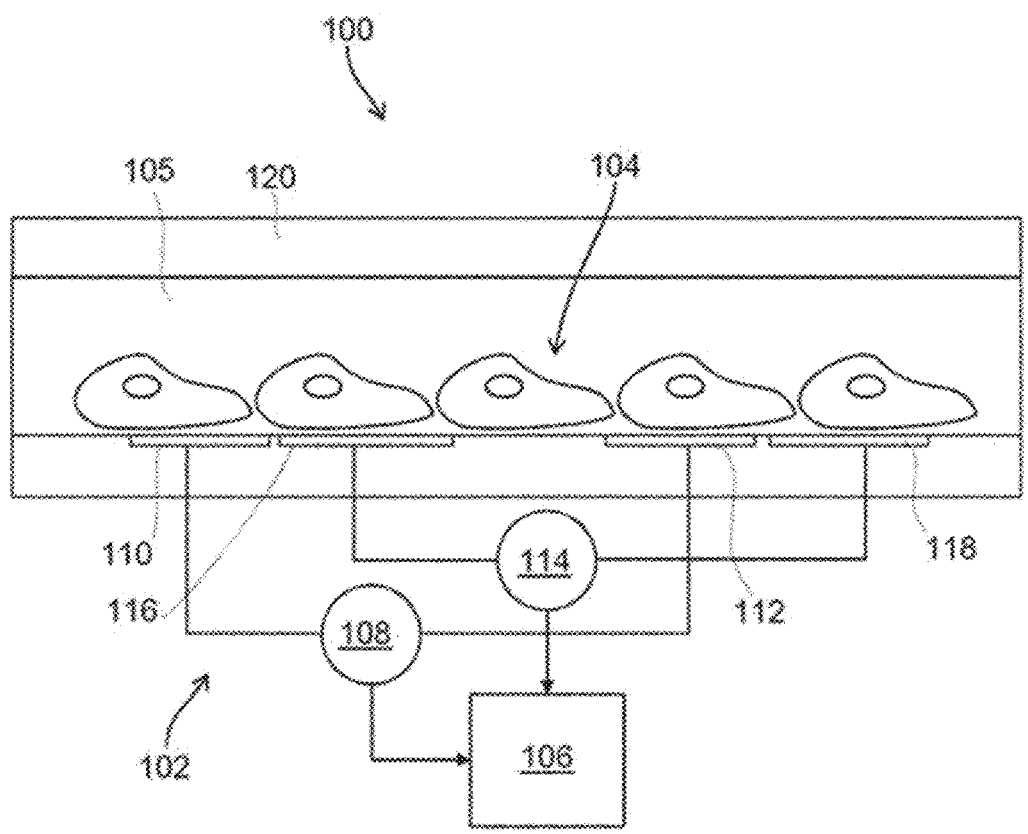
FIG. 11 illustrates an exemplary system for implementing the method of FIG. 4.

By way of example, FIG. 11 illustrates an example 100 of a system for implementing the method as described previously.

The system 100 essentially comprises means 102 for measuring the impedance of a lesion 104, here a single-layer tissue of confluent cells, dipped in a medium 105, for example blood, and an electronic control unit 106, linked to the measurement means 102, to implement the method and discriminate the tissue of the lesion 104 as a function of the measured impedance.

The measurement means 102 here comprise an electrical generator 108 of alternating current, linked to two electrodes 110, 112 in contact with the lesion 104. The measurement means 102 also comprise a device 114 for determining the intensity passing through the lesion 104, linked to said lesion 104 by two electrodes 116, 118 in contact with the lesion 104. The electronic control unit 106 is linked to the electrical generator 108 and to the intensity measurement device 114, in order to be able to determine the impedance of the lesion 104, for example from the measurement of the voltage and of the intensity at the terminals of the electrodes 110, 112, 116, 118.

The electrodes 110, 112, 116, 118 consist of an electrically conductive material, such as gold for example.

Here, advantageously, the measurement means 102 further comprise a medical device 120 that may be inserted in an animal subject, here an invasive probe 120. In this case, the electrodes 110, 112, 116, 118, the alternating voltage generator and the intensity measurement device may be fixed onto this medical device. The medical device is for example as described in the application FR3026631 A1 MEDICAL DEVICE PROVIDED WITH SENSORS HAVING VARIABLE IMPEDANCE filed on 2014 Oct. 3, the entire contents of which, and in particular the discussion of implantable medical devices including measurement devices, are incorporated herein by reference.

In this case, the alternating electrical generator 108 may include an armature, such as the body of the medical device or an antenna electrically insulated from the body of the medical device, adapted to emit an electrical current under the effect of an electromagnetic field emitted by an interrogation unit external to the stent 120. The electrodes may then form a sensor with variable impedance, the impedance of which varies as a function of the cellular structure which covers them. Finally, the electronic control unit may receive an item of information relating to the impedance between the electrodes, notably by emission of a magnetic field by an antenna fixed onto the body of the implantable medical device 120.

The stent 120 may thus make it possible to check the correct progress of the healing of the endothelium, after the stent 120 has been fitted. In effect, such a stent 120, in cooperation with the electronic control unit, makes it possible to determine, by implementing the method of FIG. 4, whether the cellular structure which is formed on the surface of the endothelium essentially comprises healthy endothelial cells, inflamed endothelial cells, smooth muscle cells and/or platelets.

The invention is not limited to the examples described hereinabove and numerous variants are possible, while within the scope of the definition given by the attached claims.

Thus, for example, it is possible to choose a single model of the impedance of the lesion in the step 22. In this case, it is not necessary to carry out the optimization for a number of models. The method is therefore simpler and faster to implement in this case. It is notably possible to proceed in this way when a model is considered as more relevant.

Moreover, in some examples described, the discrimination of the tissues/materials is based essentially on the calculated effective capacitance and on its comparison with pre-established values. As a variant, however, it is possible to proceed with the discrimination of the tissues/materials from parameters of the chosen model of the impedance of the lesion. However, it seems that the comparison of just the value of the effective capacitance is both simple and allows for a reliable discrimination of the tissues/materials.

Figure 19:
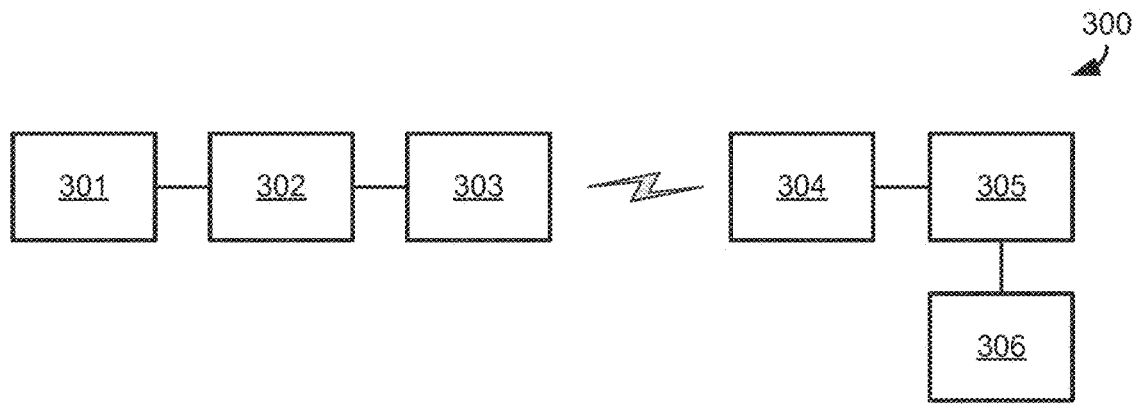
FIGS. 19 and 20 show examples of systems made in accordance with aspects of the present disclosure.

FIG. 19 shows an example of a system 300 made in accordance with aspects of the present disclosure. This system comprises a measurement module 301 with may be part of an implanted device, for example a stent, or of a device for in vitro cultivation of cells.

The measurement module comprises at least two electrodes and may be as described above with reference to FIG. 11.

The system 300 also comprises an internal processing unit 302 that is configured for example to generate an impedance spectrum from data from the measurement module.

The system 300 may comprise an emitter 303 to wirelessly transmit data (the data from the measurement module 301 and/or the impedance spectrum determined by the internal processing unit 302) to a receiver 304, which may be external to the body in case the measurements take place in vivo. The transmission may take place under any wireless protocol such as RFID, NFC, Bluetooth, WiFi, either radio or Infrared, inter alia. In some embodiments, the transmission may include transmission via one or more wired and/or wireless local and/or wide-area networks, including the Internet.

The system 300 may comprise an external processing unit 305 to compute the impedance spectrum (in the case of receiving from the emitter 303 the data from the measurement module 301) and/or the various parameters and effective capacitance $C_{eff}$ based on the received data and display means 306 such as a LCD screen to display information relating to the type and/or condition of cells determined based upon comparison of a value representative of $C_{eff}$ with reference data. To determine the various parameters and effective capacitance, the external processing unit 305 may be configured with information regarding one or more equivalent circuit models for an impedance, and determine the parameters of at least one of the model(s), such as in the manner discussed above. The external processing unit 305 may also be configured to select one of the models, following determination of the parameters of the model(s), as a model from which to determine the effective capacitance, as discussed above. The external processing unit may make the selection based on a degree of fit between the equivalent circuit model and the impedance spectrum. The system may provide, based on the at least one type and/or condition of cells thus identified, information representative of an evolution of a healing process, for example, information regarding a current status of an area in which (e.g., tissue to which) a procedure was performed (including positioning of an implant such as a stent) and/or provide information regarding a change over time in the status of the area that may be reflective of a response to the procedure in the area, such as a healing or scarring response.

The external processing unit may be a special-purpose device that includes specialized hardware such as an ASIC, EEPROM, or other component specially configured to perform the operations of the external processing unit described above. In other embodiments, the external processing unit may be a general-purpose device such as a laptop or desktop personal computer, a server, a smart/mobile phone, a personal digital assistant, a tablet computer, or other computing device including mobile computing devices. In the case that the external processing unit is implemented with a general-purpose device, the general-purpose device may include one or more processors and a non-transitory computer-readable storage medium (e.g., an instruction register, an on-chip cache, a memory, a hard drive, a removable medium such as an optical medium) having encoded thereon instructions for execution by the processor(s), where the instructions cause the processor to carry out the operations described above as performed by the external processing unit. The internal processing unit may, in some embodiments, be any appropriate IC chip or other hardware component with processing capabilities. The external and internal processing units may be located proximate to one another (e.g., within a same room, or within 5 feet) or may be located remote (e.g., in different parts of a building or complex of buildings) or geographically remote (e.g., miles apart) from one another, such as in the case that the external processing unit is implemented in a server and data is transmitted via one or more networks or the Internet.

Figure 20:
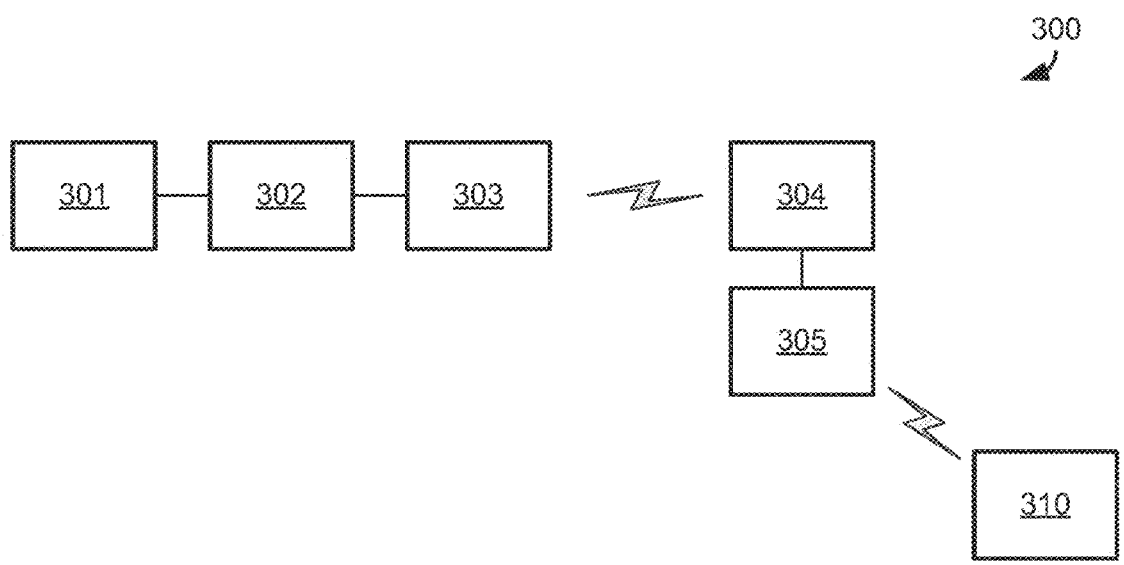

In a variant, as shown in FIG. 20, part of the processing is carried out in a distant server 310 to which data is transmitted via the internet for example.

EXAMPLES

Figure 25A:
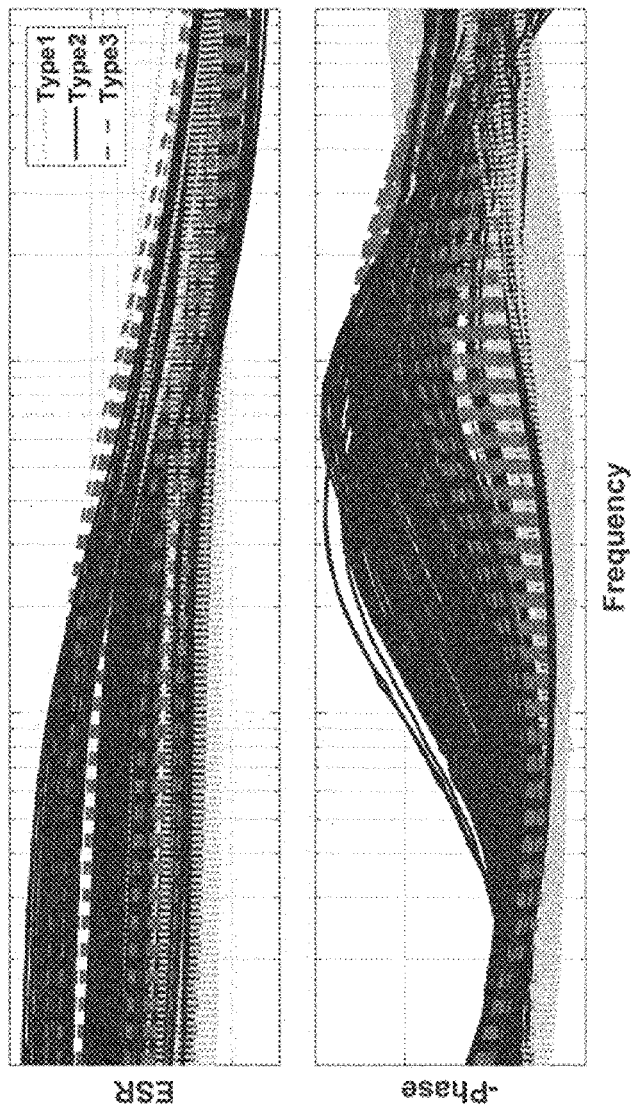
FIG. 25A-25B are graphs showing amplitude and phase spectra for experimental data.

FIG. 25A shows a collection of amplitude and phase of an impedance spectra measured for cellular structures comprising respectively three cell types, i.e. platelets, smooth muscle cells and endothelial cells.

COMPARATIVE EXAMPLES

First, an equivalent circuit model without CPE is used, consisting of a double layer capacitance Cd1 in series with a solution resistance in series with a R0Cmix (R0 resistance in parallel with Cmix capacitance).

Then, the Cmix parameter describing the impact of the cells layers on the complex impedance is computed.

Figure 26A:
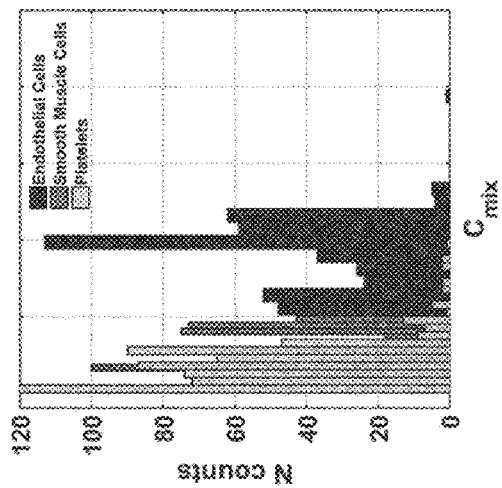
FIGS. 26A-27F are histograms showing various parameter distributions.
Figure 26B:
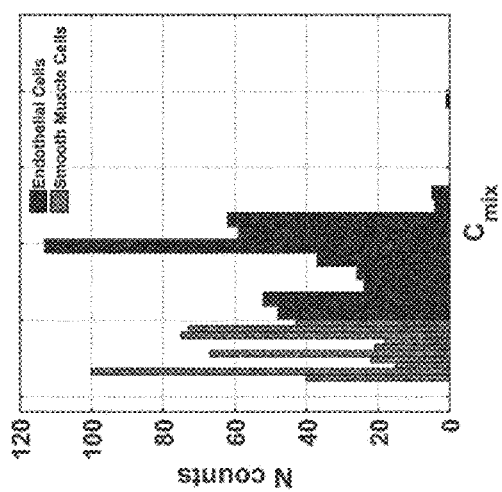
Figure 27A:
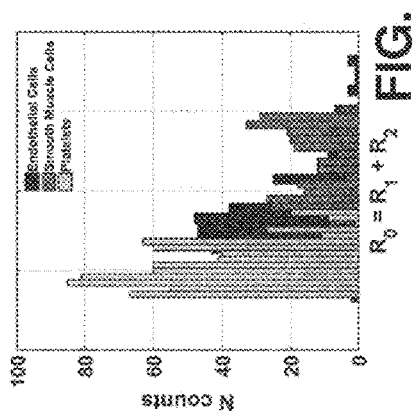
Figure 27B:
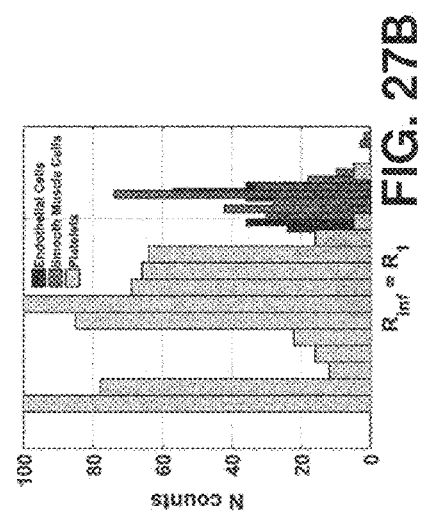
Figure 27C:
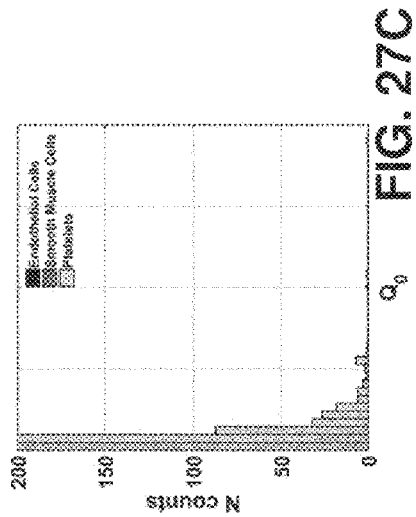
Figure 27D:
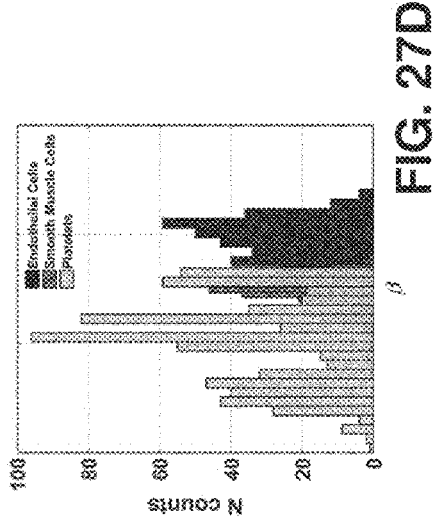
Figure 27E:
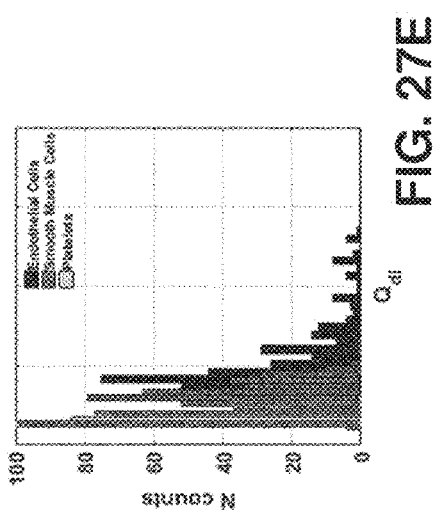
Figure 27F:
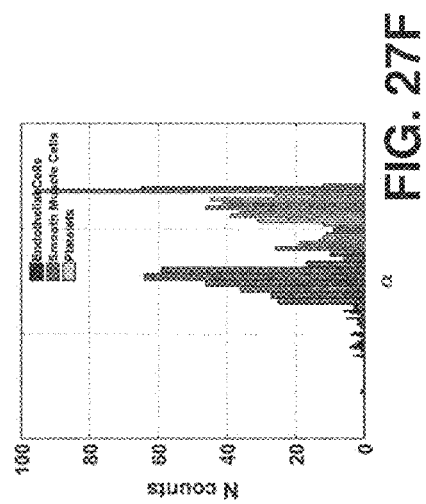

The result of the distribution of Cmix for two cell types is shown in FIG. 26A. It is possible to distinguish between the two cell types. However, if adding a third cell type the three cell types cannot be distinguished any longer, as shown in FIG. 26B.

If one uses a more sophisticated approach and implement CPE elements into the equivalent circuit model, and uses for example the model 34 shown in FIG. 8A, there are six parameters describing the system, i.e. R0, Rinf, Q0, $\beta$, Qd1 and $\alpha$.

These parameters can be computed so that the impedance of the equivalent circuit model best fit the experimental impedance spectra curves in FIG. 25A.

Then, one can display for each parameter the distribution of this parameter for the three cell types, as shown in FIGS. 27A to 27F.

One can see that for each parameter the three cell types cannot be distinguished clearly, and no linear combination of these parameters can provide the cell discrimination that is looked for.

Examples According to the Invention

Figure 28:
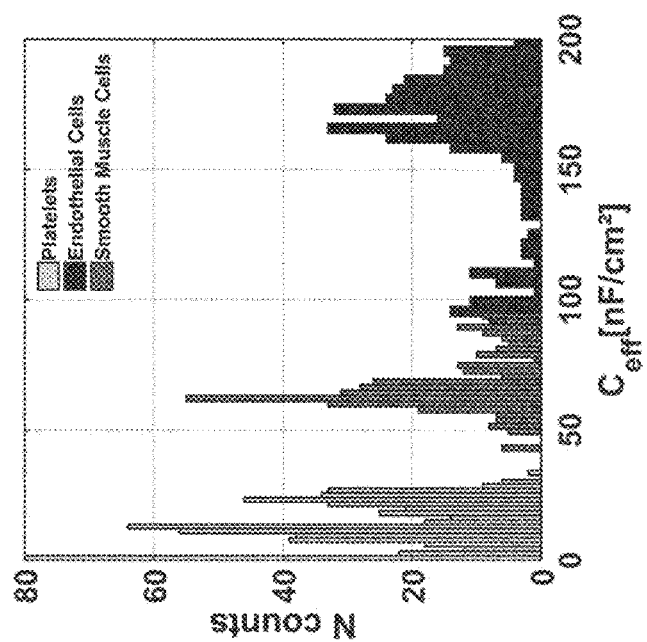
FIGS. 28-30 are histograms showing distributions of values representative of effective capacitance for different cell types.

FIG. 28 shows the distribution of a value representative of the effective capacitance Ceff for the three cell types, determined based on the formula [8] above.

One can see that it is possible to clearly distinguish between all three cell types. The precision is over 90%. The differentiation between cells is significantly improved compared to FIGS. 27A-27F.

Figure 29:
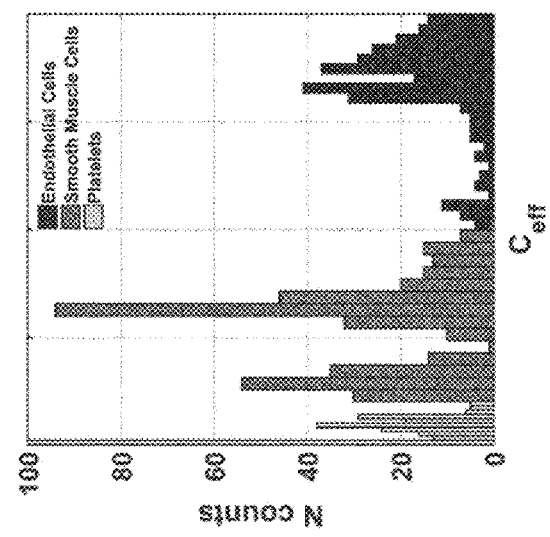

If the equivalent circuit is the one 34' of FIG. 8B, one obtains the $C_{eff}$ distribution of FIG. 29.

Figure 30:
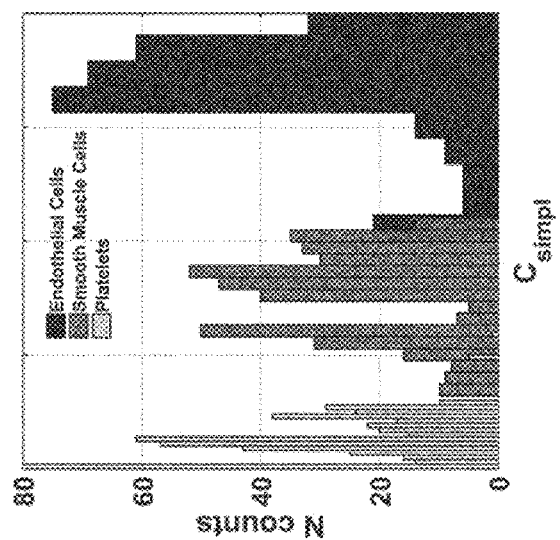

If one considers R0-Rinf is large in respect to Rinf, the equation [8] can be simplified as Ceff=$(1-\alpha)/\alpha$ The resulting distribution of Ceff is shown in FIG. 30. One can see that the three cell types can still be distinguished with a precision of about 85%.

The distributions shown in FIGS. 28-30 may serve as reference data for cell type determination.

For example, an impedance spectrum may be measured in similar conditions as the impedance spectra of FIG. 25A, and based on this spectrum the values of parameters R0, Rinf, Q0, $\beta$, Qd1 and $\alpha$ are determined. This determination may be based on least square fitting of the impedance curves of amplitude and phase with the equivalent circuit model 34 of FIG. 8.

Then, once the parameter values R0, Rinf, Q0 and $\alpha$ are known, the effective capacitance Ceff can be computed and the value compared with the distribution of FIG. 28 to determine to what cell type it corresponds. For example, a low value of Ceff in nF/cm2 will indicate that the cells are of first type; a value between about 50 and about 100 that the cells are of type 3, and a value of over about 100 that the cells are of type 2.

Example Biological Structure Analysis Techniques

As discussed above, the effective capacitance of a biological structure, including cells, tissues, and/or lesions (including lesions comprising cells and/or other materials), may be determined based on captured impedance measurements and employed to identify the composition of the biological structure (e.g., the cells and/or tissue in the lesion). The inventors have appreciated, however, that using the effective capacitance to identify the composition of a lesion or otherwise characterize a lesion may not be the most effective option under all conditions.

Figure 21A:
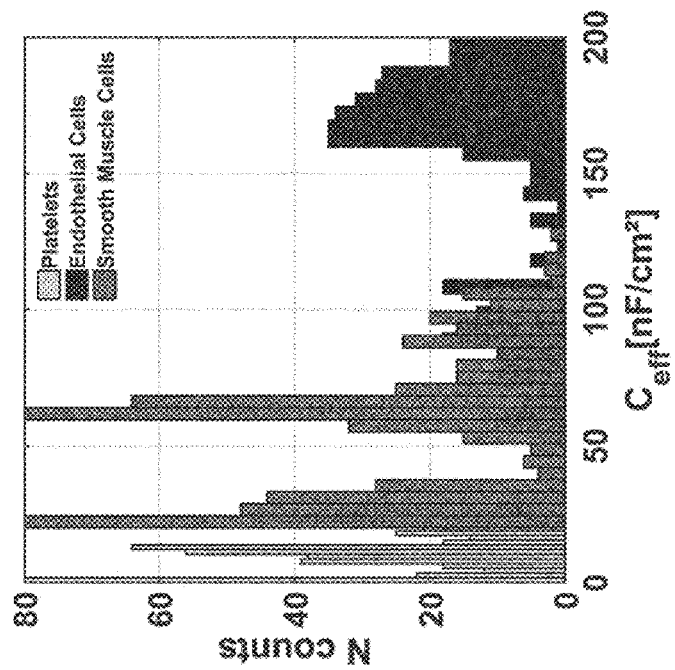
FIG. 21A is a histogram showing the determined effective capacitance of multiple types of cells under controlled conditions.

For example, using the effective capacitance to discriminate between different cell types in a lesion may be very effective (e.g., achieve 95% accuracy) where the measurements of each cell type are captured under controlled conditions (e.g., same temperature conditions, same flow conditions, etc.). The distribution of effective capacitances determined for platelets, smooth muscle cells, and endothelial cells under controlled conditions is illustrated by the histogram in FIG. 21A. As shown, the effective capacitance of platelets, smooth muscle cells, and endothelial cells has little overlap. In particular, the effective capacitance of platelets is generally below approximately 40 nanofarads per square centimeter, the effective capacitance of smooth muscle cells is generally between 40 and 90 nanofarads per square centimeter, and the effective capacitance of endothelial cells is generally above 90 nanofarads per square centimeter. Because there is little overlap, effective capacitance may be used to reliably differentiate between these different biological structures.

Figure 21B:
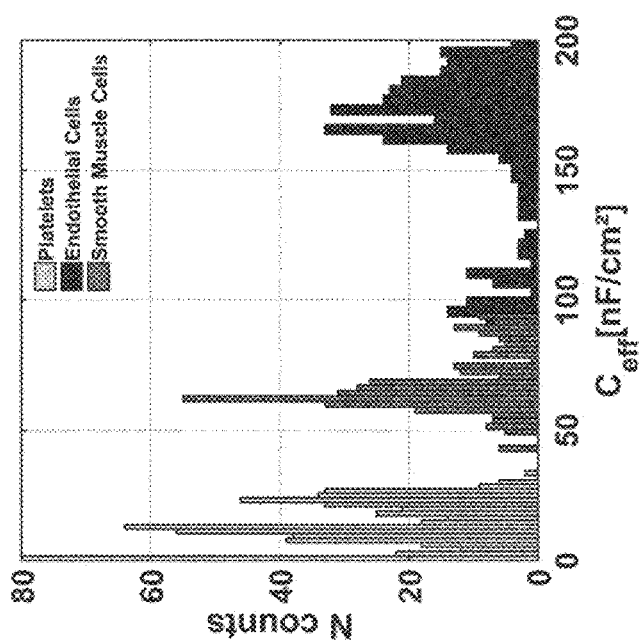
FIG. 21B is a histogram showing the determined effective capacitance of multiple types of cells under uncontrolled conditions.

Effective capacitance, however, may be less reliable when discriminating between different biological structures under less controlled or uncontrolled conditions. This may include varying temperature conditions, varying flow conditions, or other changes. Such variations may be present during in vivo measurements. The distribution of effective capacitances determined for platelets, smooth muscle cells, and endothelial cells under uncontrolled conditions is illustrated in the histogram in FIG. 21B. As shown, the effective capacitance of platelets substantially overlaps with the effective capacitance of smooth muscle cells. Further, the effective capacitance of the smooth muscle cells substantially overlaps with the effective capacitance of endothelial cells. The overlap between the effective capacitance of different cell types reduces the performance of cell discrimination techniques that use the effective capacitance of a cell.

The inventors have developed techniques to identify characteristics (e.g., a type and/or state) of a biological structure, such as the type and/or composition of a tissue and/or the type and/or composition of cell(s), with higher reliability. Such techniques may leverage machine learning. For example, machine learning may be employed to interpret and classify EIS measurements to identify the composition of a biological structure, such as a tissue, collection of cells, a lesion of an animal, or other structure or collection of biological materials. Using machine learning techniques to identify characteristics of a biological structure offers numerous advantageous relative to prior approaches. The machine learning techniques disclosed herein may provide more accurate results than were possible through use of effective capacitance determined under some uncontrolled conditions. For example, some trained models developed using the machine learning techniques described herein may identify the composition of some biological structures with 99% accuracy. Further, using a trained model to identify characteristics of a biological structure may be less computationally intensive than other analysis techniques. For example, using a trained model to identify the composition of biological structure may only require a device to perform a series of multiplication and summation operations, involving weighting values or other values generated during the training of the model. In contrast, identifying the composition of a biological structure based on the effective capacitance of the lesion may require a device to perform a computationally intensive process to derive the effective capacitance from the impedance measurements that includes fitting a model to the impedance measurements.

In some embodiments, machine learning techniques may be employed to identify the relative abundance or concentration of different types of cells or tissues that are present in a lesion (e.g., a clot). In this way, clots of the same type but having different relative amounts or concentrations of a particular type of cell or material, such as different relative amounts or concentration of red blood cells, may be differentiated from one another. Accordingly, in some embodiments, a model may be trained to identify amounts of a particular biological material (e.g., a particular type of cell, such as a red blood cell) in a biological structure. The amount of the material that is identified may be an absolute amount, such as a certain volume or mass of the material, or other value indicative of an amount of the material. In other embodiments, the amount of the material that is identified may be a relative value, such as an amount relative to amounts of one or more other materials, including an amount relative to an overall amount of other materials in a biological structure. For example, a ratio may be determined that identifies an amount of a biological material (e.g., red blood cells) in a lesion relative to a whole of the lesion. The ratio may be a ratio by volume, by mass, or according to any other suitable value reflective of an amount of the type of biological material in the lesion.

In some embodiments, machine learning techniques described herein may be used to quantify the relative amounts or concentrations of the different types of cells or tissues that constitute or are otherwise part of a lesion or other tissue. For example, in one embodiment it may be determined, using machine learning techniques, that a clot includes 50% red blood cells, 30% fibrin and 20% platelets. As another example, an embodiment may determine a relative amount of material for only one type of material, such as that a lesion is 50% composed of red blood cells, without specifically identifying the materials of the other 50% of the lesion.

The inventors have further appreciated that the direct application of machine learning techniques to tissue and/or cell classification may yield unsatisfactory results, and appreciated the value of specific ways of leveraging machine learning. For example, directly training models using machine learning techniques with EIS measurements alone may yield a trained model that classifies tissue or other biological structures with an accuracy that may be undesirably low in some environments (e.g., an accuracy below 80%). The inventors have appreciated that this undesirably-low accuracy may arise when using only raw EIS measurements to train models, and may stem from the amplitude and phase points in the EIS measurements being correlated while typical machine learning techniques assume that the received features are independent (e.g., not correlated).

The inventors have appreciated that using derived features in addition to the raw EIS measurements to train a model using machine learning techniques may improve the performance of the resulting model. Derived features include values that are generated from an analysis of (including computations performed on) raw EIS measurements. Such derived features may include values indicating a change in EIS measurement between frequencies, such as between adjacent frequencies of a set of frequency points to be collected. The derived features may additionally or alternatively be derived from performance of one or more statistical computations on raw EIS measurements. Example derived features that may be employed include: a phase maximum frequency of the EIS measurements, an n-quantile of the EIS measurements, a first derivative of the EIS measurements, and a second derivative of the EIS measurements.

Training a model using a set of features that includes derived features in addition to features present in the EIS measurements (e.g., data values that are included in a set of EIS measurements, and may be used as features, as opposed to values derived from the EIS measurements) may yield trained models that can, for example, identify a particular type of tissue in a lesion with up to 99% accuracy.

The inventors have also recognized that use of machine learning with EIS measurement data may be hampered by the resource constraints of some medical devices that may produce the EIS measurements. For example, in some embodiments, an implantable and/or insertable medical device (including devices as described elsewhere herein) may need to identify one or more characteristics of a biological structure with a limited number of EIS samples (e.g., 10 samples) due to various design constraints. Such a medical device may include an invasive probe (e.g., invasive probe 210) that can only remain in a duct of an animal for a limited amount of time without causing injury, limiting the time over which measurements may be made and thus limiting the number of samples that can be collected. Such a medical device may additionally or alternatively have a limited processing capability that is only capable of processing a limited number of EIS measurements, or have a limited bandwidth for communicating measurements, or a limited storage for maintaining the measurements, or suffer from other resource constraints. These constraints on the amount of data that can be collected, and that can be provided to a trained model or be used to train a model, may undermine the effectiveness of machine learning techniques.

Recognizing this difficulty, the inventors have appreciated the value of a process to train a machine learning model that can accurately identify characteristics of a biological structure given only a limited number of samples (e.g., 10 EIS samples). An example of such a model training process is shown by process 2200 in FIG. 22. The model training process 2200 may use training data including multiple sets (e.g., 5 sets, 10 sets, 15 sets, 20 sets, 50 sets, 100 sets, 500 sets, 1000 sets, or more than 1000 sets) of EIS measurements that each include a number of samples (e.g., 5, 10, 20, 50, 100, 500, 1000 or more than 1000 measurements per set) where each sample is associated sample of impedance at a particular frequency of an applied electrical signal. Each of the sets of EIS measurements may be characteristic of a particular biological sample under a particular set of conditions, and in some embodiments different training sets may correspond to different biological structures. The training process 2200 may seek to identify the particular frequencies in the multiple sets of EIS measurements that provide the best indication of the particular characteristic of the biological sample to be identified, and/or that provide data that best differentiates different biological structures. Accordingly, the training process 2200 may be used to select a subset of the training data corresponding to a particular set of frequencies (e.g., a set of 10 frequencies), construct a model using the subset of the training data, and analyze the performance of the trained model to determine whether the performance is sufficient. If the trained model's performance is insufficient, a new subset of the training data corresponding to a different set of frequencies may be selected and the process may be repeated. After a suitable combination of frequencies has been identified and corresponding trained model created, a medical device may identify one or more characteristics by capturing EIS measurements associated with the combination of frequencies (e.g., the set of 10 frequencies) and applying the captured EIS measurements to the trained model or interpreting the EIS measurements using coefficients (e.g., weighting values) or rules derived from the trained model that may be used to differentiate biological structures.

Figure 22:
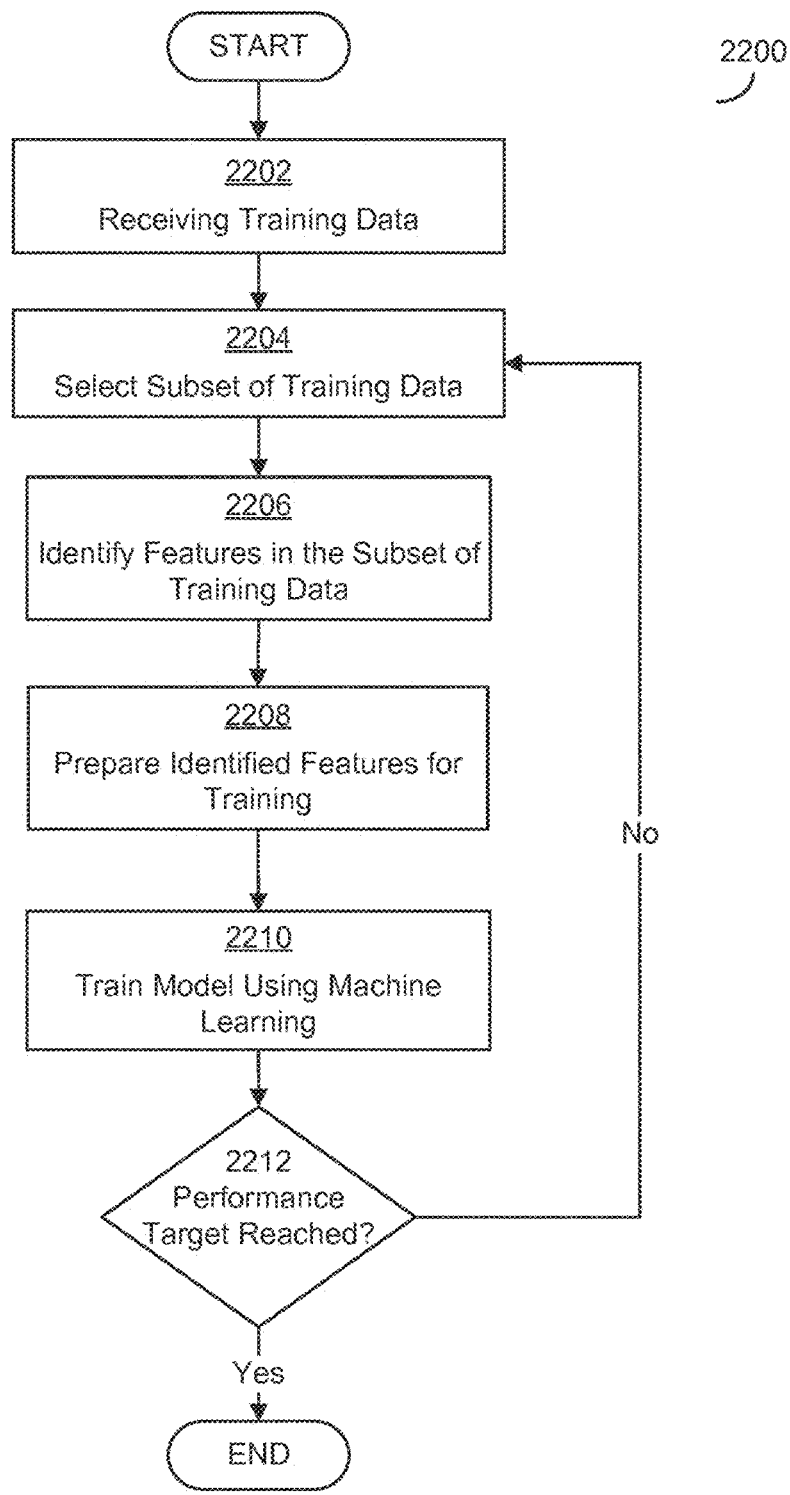
FIG. 22 is a flowchart of an illustrative process for training a model using machine learning techniques to analyze a biological material.

As discussed above, FIG. 22 shows an example training process 2200 that may train a model to identify one or more characteristics of a tissue and/or cell based on a small number of samples (e.g., 10 EIS samples). The model generation process 2200 may be performed by a medical device and/or performed by a computer system in communication with the medical device that provides the resulting trained model and/or coefficients or rules derived from the trained model to the medical device. As shown in FIG. 22, the training process 2200 includes a block 2202 of receiving training data, a block 2204 of selecting a subset of the training data, a block 2206 of identifying features in the subset of the training data, a block 2208 of preparing the identified features for training, a block 2210 of training a model using machine learning, and a block 2212 of determine whether a performance target was reached.

In block 2202, the system may receive training data. The particular composition of training data may depend upon the desired characteristics to be identified. For example, the model may be trained to differentiate between different types of tissues and/or cells in a lesion. In this example, the training data may include multiple sets (e.g., 20 sets) of EIS samples (e.g., 100 samples per set). Each of the sets of EIS samples may be associated with a particular type of tissue and/or cell to be identified (e.g., platelets, smooth muscle cells, and endothelial cells) under certain conditions. The EIS samples within each set may be indicative of an impedance magnitude and/or phase of a biological structure at a particular applied frequency.

In block 2204, the system may select a subset of the training data to use to train the model during one iteration of training. The subset of the training data may include multiple sets of EIS measurements and more particularly include, for each set, a subset of EIS measurements as compared to the originally-input sets. The subsets may include, for example, EIS measurements for only certain frequencies of applied signals.

The identified subset of the training data may be subsequently employed to train the model in blocks 2206-2210. If the performance of the resulting trained model fails to meet the appropriate performance targets, the system may return to block 2204 to determine a new subset of the training data that is different from the previously determined subset of the training data. For example, a first subset of the training data may include the EIS measurements from each of the sets of samples that correspond to the frequencies $f_1$, $f_2$, and $f_3$. In this example, the system may subsequently determine that the model trained using this subset of the training data performed poorly. Accordingly, the system may return to block 2204 and select a second subset of the training data that may include the EIS measurements from each of the sets of samples that correspond to the frequencies $f_1$, $f_3$, and $f_5$.

It should be appreciated that, at least in some circumstances, the measurement data may be at least partially distorted by the presence of noise. Accordingly, to statistically mitigate the effect of noise on the data, the biological material may be sampled numerous times using the sensors. For example, the biological material may be sampled such that at least three spectra are obtained in less than three seconds, at least five spectra are obtained in less than three seconds, or at least ten spectra are obtained in less than three seconds. Using multiple spectra may increase the degree of confidence of the model.

It should also be appreciated that the system may use any of a variety of techniques to identify the subset of the training data. In some embodiments, the system may select the subset of the training data by randomly. For example, the system may randomly determine a set of frequencies and select the measurements from the training data that correspond to the random set of frequencies. In other embodiments, the system may intelligently select the subset of the training data using a genetic algorithm. The genetic algorithm may, for example, take into account the performance of trained models using previous subsets of the training data, in prior iterations, and may be applied when the system determines in block 2212 that the performance target was not reached.

In block 2206, the system may identify the particular features in the subset of the training data to use in training the model. The system may identify, for example, the EIS measurements in the subset of the training data as features. The system may also determine one or more derived features that are derived from the EIS measurements. For example, the system may determine a first and/or second derivative of the EIS measurements in the subset of the training data. The first and/or second derivative may be calculated for each set of measurements, within the subset, and may be calculated as derivatives based on the EIS measurements within a particular set. For example, if a measurement set includes 10 samples, the system may calculate a first derivative for each pair of values as a change in the amplitude or phase (or both, as distinct values) between frequencies that are adjacent in the measurement set. In this case, a second derivative may be calculated as a change (in amplitude or phase, depending in the nature of the first derivative) between adjacent values of the sets of first derivatives. In another example, the system may determine a phase maximum frequency and/or an n-quantile of the EIS measurements in the subset of the training data. N-quantiles may be the values that partition the area under a curve into n equal (or nearly equal) subsets. For example, the curve defining a magnitude of the impedance over a frequency range may be divided into n equal (or nearly equal) sections and the particular frequencies that mark the division between the sections may be employed as a derived feature.

In block 2208, the system may prepare the identified features for use in training the model. Preparing the data may include various functions such as removing noise, removing redundant information, and/or data formatting. For example, the system may normalize the identified features and/or identify principle components of the identified features using principle component analysis (PCA).

In block 2210, the system may train a model with the identified features using at least one machine learning technique. Any of a variety of machine learning techniques may be employed including, for example, a support vector machines (SVM) technique, an artificial neural network (ANN) technique, a k-nearest neighbors (kNN) technique, and a decision tree learning technique.

In block 2212, the system may determine whether the trained model generated in block 2210 meets one or more performance targets. For example, the system may test the machine learning model using training and/or test data to assess the performance of the machine learning model. Assessing the performance may include comparing an output generated for a given set of inputs to an expected output for those inputs, such as comparing a diagnosis of a lesion based on a set of EIS measurements for the lesion to a known type of the lesion. Such a comparison may be performed one or more times in an iteration of training, based on a model generated in that iteration, to generate a value indicative of an accuracy of the trained model. The performance target may include, for example, a minimum accuracy level. If the trained model fails to meet or exceed the performance target, the system may return to block 2204 and select a new subset of the training data. As mentioned above, in some embodiments, if the performance target is not met, in returning to block 2204 to select a new subset and determine specific measurements to make, the system may make use of a genetic algorithm to learn over time the frequency selections to make in block 2204. For example, the system may start with multiple possible combinations of specific measurements and evaluate the performance of each combination of specific measurements. In this example, the worst performing combinations of specific measurements may be removed from consideration and the best ranking combinations of specific measurements may be mixed together to form new combinations of specific measurements. This process of testing the performance of combinations of specific measurements, remove the worst performing combination of specific measurements, and mixing the top performing combinations of specification may be repeated until an appropriate combination of specific measurements is identified. In other embodiments, however, a random selection process may be used in block 2204.

Otherwise, if the performance target is met or exceeded, the system determines that the model has been successfully trained and the process 2200 ends.

Following the process 2200, a specific set of frequencies to use for EIS measurements that provide for adequate differentiation between biological structures has been identified, and a model has been trained to differentiate biological structures using those frequencies. The frequencies and the model may be stored following the process 2200. In addition, a medical device (including implantable and/or insertable devices as described elsewhere herein) may be configured to measure impedance of a biological structure at those frequencies, and a system (either the medical device itself, or in combination with another computing device such as discussed above in connection with FIG. 2) may be configured to identify a biological structure, identify a composition of a biological structure, or otherwise characterize a biological structure using the trained model and/or coefficients or rules derived from the trained model that may be used to analyze EIS measurements to perform the identification or characterization.

Those skilled in the art will appreciate that in some techniques for training a model, the model learns various weighting values or other values (which may also be termed coefficients) to use in computations that produce particular outputs from inputs. In such case, a set of these weighting values can be said to represent the model, together with information on the computations to be performed on inputs using the weighting values. Accordingly, in some embodiments, as a result of the process of FIG. 22 (or other processes described herein that result in trained models), a set of weighting values is generated that can be used to configure devices for subsequent use by the devices. For example, a model trained as a result of the process 2200 of FIG. 22 may result in a model that allows for identifying and/or categorizing lesions (or other biological structures of interest) based on input features determined from EIS measurements for the lesion. That model may be represented as a set of weighting values that allow for identifying, from the features, one or more characteristics of the lesion. By configuring a device to perform computations using those weighting values, the device can generate the characteristics based on the input features, such as by generating a mathematical value from the EIS measurements and the weighting values and determining that the mathematical value matches a particular characteristic or set of characteristics. Performing such computations may be computationally less intensive than other forms of analysis that may be performed on input features to generate characteristics, and thus may require less time or less processing resources than alternatives.

It should be appreciated that various alterations may be made to the process 2200 without departing from the scope of the disclosure. In the process 2200 as discussed above, in block 2206 the same set of features were selected in each iteration based on the selected subset of training data. In some cases, this set of features may be inadequate to reach the performance target regardless of which subset of training data is selected, or there may be a set of features that may provide for more accurate analysis. In some embodiments, the process 2200 may optimize or otherwise improve the particular features used to train the model in addition to optimizing or improving the particular portion of the training data used to train the model. For example, after the system determines that the trained model failed to meet the performance target in act 2212, or if the system determines that the trained model has reached a performance plateau that does not meet or exceed the performance target (or has reached a performance plateau, even if the performance meets or exceeds the target), the system may change the particular features employed to train the model in block 2210 in addition to (or in place of) changing the subset of the training data. The selection of the features may be driven by a similar genetic algorithm as was discussed above in connection with selecting measurement values. Thereby, the system may iterate through multiple different combinations of features until a combination of features that yields desired performance is identified.

Figures 23, 24:
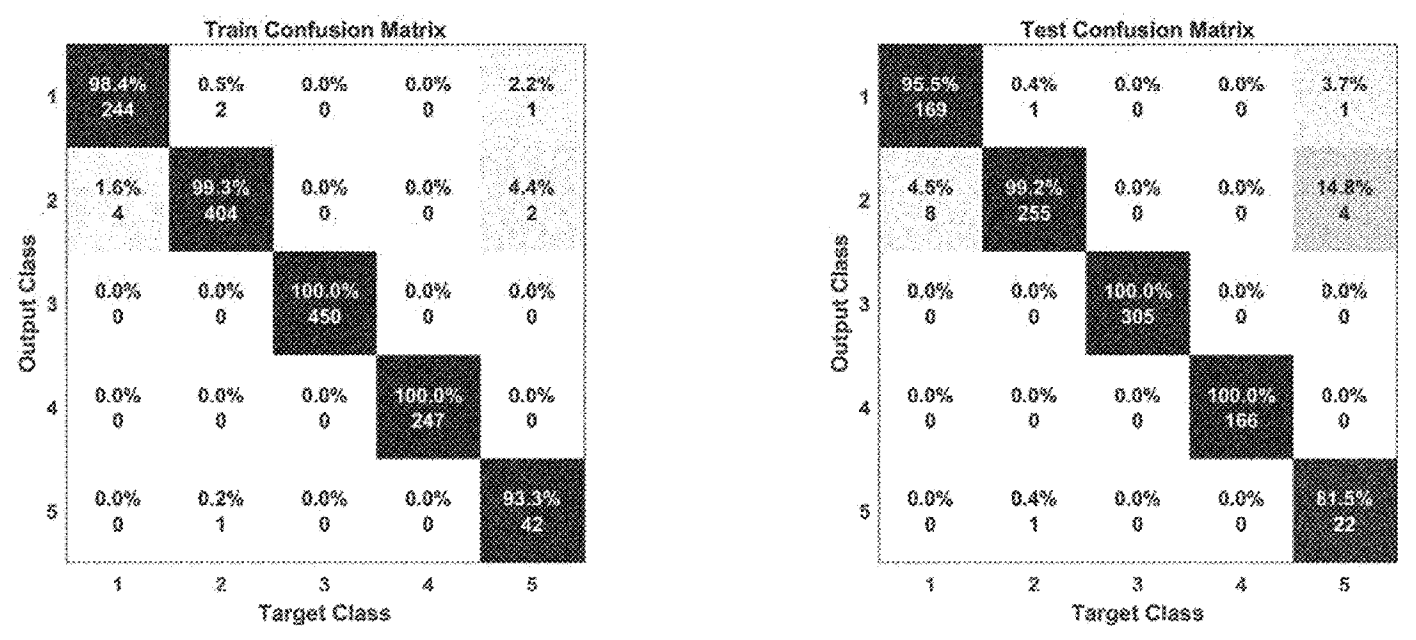

Example results obtained from using process 2200 to generate a trained model that discriminates between various cell types based on 10 EIS measurements is shown by the confusion matrices in FIGS. 23 and 24. These confusion matrices are tables which allow direct visualization of the result of the model applied to specific classes of samples. Each row of a matrix represents the instances in a predicted class while each column represents the instances in an actual class. The values of the diagonal indicate cases in which the model predicts the labeled class correctly. The values shown in the diagonal represent the probability with which the corresponding labeled class is correctly predicted. The off-diagonal values represent cases in which the model confuses a class for another, with the corresponding probability. The model was trained to discriminate between the following five classes: 1—Bovine Aortic Endothelial Cell (BAEC), 2—Bovine Aortic Smooth Muscle Cell (BAOSMC), 3—Platelets; 4—Empty; 5—Intermediate. FIG. 23 shows the results from the application of the training data to the trained model and FIG. 24 shows the results of the application of test data to the trained.

In some embodiments, the cell discrimination method 10 of FIG. 4 may be configured with particular frequencies with which to perform EIS measurements, rather than performing a continuous or pseudo-continuous measurement across a spectrum. The particular frequencies may be those that generate impedance values that, when analysed, provide for the clearest differentiation between different biological materials. In some embodiments, the clearest differentiation may be impedance spectra with little overlap between the spectra, while in other embodiments the clearest differentiation may be the least overlap or similarity in values or ranges of values that may be used to identify biological materials. For example, in some embodiments in which effective capacitance is determined and used to identify a biological material or otherwise determine one or more characteristics of a biological material, the clearest differentiation may be the least overlap or similarity in values or ranges of values for effective capacitance associated with different types of biological materials.

Figure 24A:
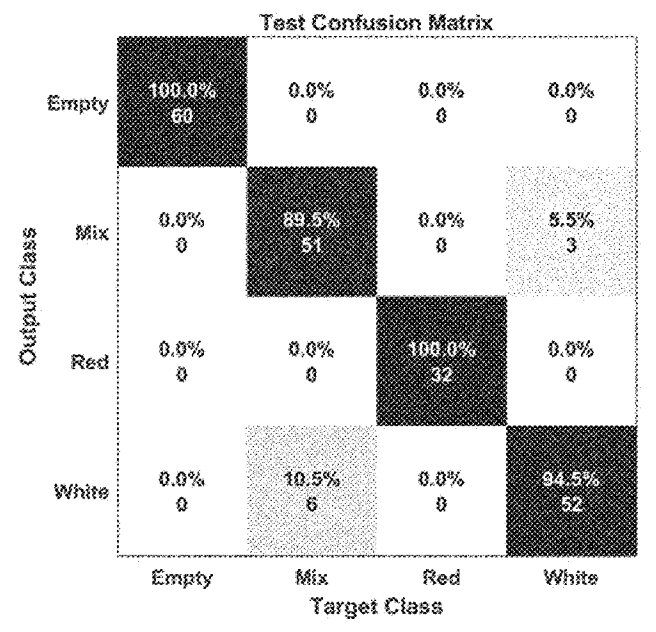
Figure 25B:
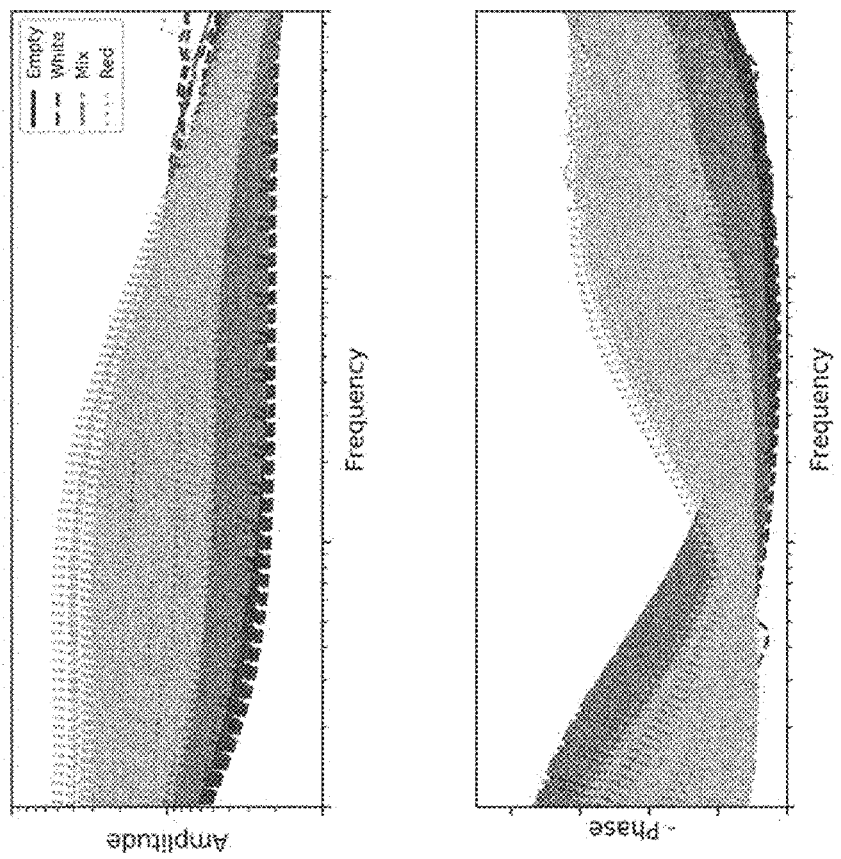

FIG. 24A illustrates another confusion matrix, where the true labels are shown as rows and the predicted labels as columns. In this case, four classes were considered: "empty", "mix", "red" and "white." Each class represents a different type of clot. For example, the class "red" represents a type of clot that is rich in red blood cells, the class "white" represents a type of clot that is rich in fibrins, the class "mix" represents a type of clot that is rich in fibrins as well as red blood cells, the class "empty" represents a case in which no clots are present. As shown in the matrix, which was generated based on 3000 EIS measurements, clots of the "red" class were predicted by the trained model with 100% probability, clots of the "white" class were predicted with 94.5% probability, etc. By contrast, clots labeled "white" were erroneously predicted as "mix" with 10.5% probability, clots labeled "mix" were erroneously predicted as "white" with 5.5% probability, etc. The EIS measurement data sets used for generating the matrix of FIG. 24A are shown in FIG. 25B. The top chart illustrates data points representing impedance amplitude vs. frequency for the different classes. The bottom chart illustrates data points representing impedance phase vs. frequency for the different classes.

While FIG. 22 was described in connection with approaches to training a model to determine characteristics of a biological structure based on input impedance measurements, and to determine frequencies/features as part of learning to determine the characteristics, it should be appreciated that embodiments are not limited to using the process of FIG. 22 to learn a relationship between impedance measurements and one or more characteristics of a biological structure. For example, as discussed further below in connection with FIG. 15C, in some embodiments a model may be trained to learn a relationship between impedance measurements for a biological structure and a treatment to recommend for the biological structure (e.g., treatments for lesions, where the biological structures are lesions). In some such embodiments, as discussed in connection with FIG. 15C, a system may use impedance measurements collected by a device as described herein to determine a treatment recommendation for a biological structure sensed by the device, without performing an intermediate step of identifying or characterizing the biological structure. In such embodiments, training a model to learn a relationship between impedance measurements and treatment recommendations may include identifying frequencies and/or features, as discussed in accordance with FIG. 22.

In addition, it should be appreciated that, as discussed elsewhere herein, such an embodiment that generates a treatment recommendation based on impedance measurements may generate a treatment recommendation that is a recommendation of a treatment option to use from among a set of treatment options (e.g., different tools to use), a recommendation of a manner in which to perform that treatment option (e.g., a manner in which to operate a tool, generated before and/or during execution of the treatment), or recommendation not to treat, among other types of recommendations.

Methods of Operating a Medical Device

Examples of medical devices, sensors, and manners of sensing tissues/materials of a lesion are described in detail above with respect to FIGS. 2-11. Described below in connection with FIGS. 12-16 are examples of techniques that may be implemented by such a medical device and/or that a medical device may be operated to perform.

Figure 12:
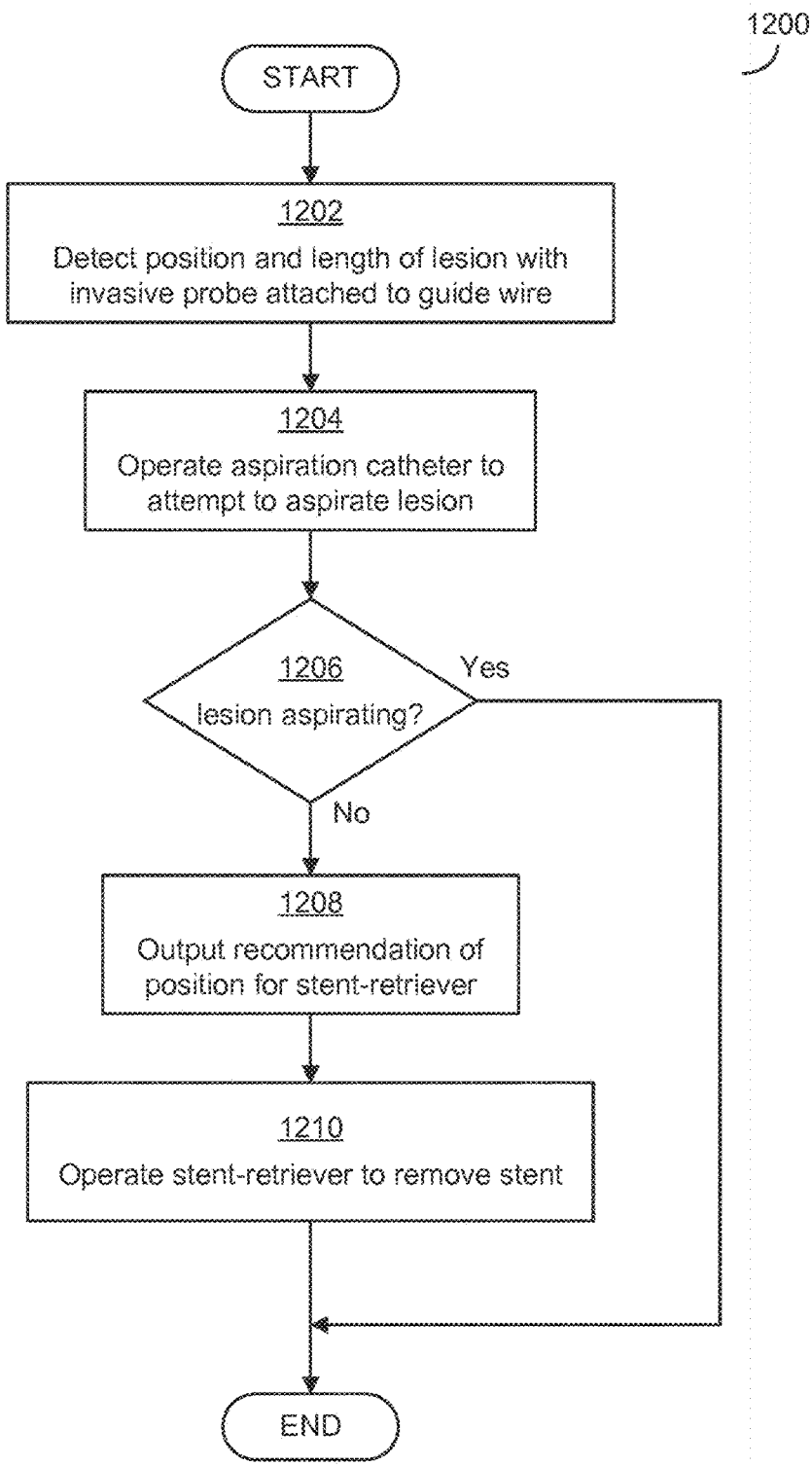
FIG. 12 is a flowchart of an illustrative method for operation of medical devices in accordance with some embodiments described herein to generate treatment recommendations.

FIG. 12 illustrates, for example, a process 1200 that may be performed by a medical device operating in accordance with some techniques described herein. The medical device of the example of FIG. 12 may be a medical device in which an invasive probe may include only a single sensor, which may include one or two electrodes. As should be appreciate from the foregoing discussion, a limited amount of information regarding a lesion may be determined from a single sensor, as compared to multiple sensors arrayed along an invasive probe (e.g., in the example of FIG. 3). In the example of FIG. 12, the sensor of the invasive probe may be disposed in treatment devices, such as in an aspiration catheter and in a stent-retriever, and/or in a guide wire that is inserted prior to insertion of the aspiration catheter or stent-retriever. The medical device may generate treatment recommendations based on characteristic(s) of the lesion determined using the sensor.

The process 1200 begins in block 1202, in which a sensor attached to a guide wire is operated to detect one or more characteristics of a lesion that is proximate to the sensor. Prior to the start of the process 1200, an invasive probe of the guidewire, of which the sensor is a part, may be inserted into vasculature of an animal and moved proximate to a predicted location of the lesion. The sensor then is operated to detect when the sensor contacts the lesion. Contact of the lesion may be determined by evaluating a change over time in a value output by the sensor. For example, the sensor may output one value when contacting blood, which may be the case when the sensor is disposed in a middle of a vessel at an area not blocked by the lesion. When the invasive probe is moved forward until contacting the lesion, a value output by the sensor may change once contact is made. In this manner, a location of the lesion may be determined using the single sensor. The sensor may additionally, in some cases, be operated to determine a length of the lesion, such as by continuing to advance the invasive probe until the sensor is no longer contacting the lesion and the output value returns to a value that was associated with contacting blood.

In the example of FIG. 12, using only a single sensor, the medical device may not be aware of a composition of a lesion and may not be able to make treatment recommendations regarding which treatment option may be best to treat a particular lesion. However, the medical device may be able to produce information regarding a progress or success of a treatment, which may be used to determine whether a selected treatment option is being performed successfully. Based on this information, the medical device may generate a treatment recommendation on whether to change a treatment being performed to another treatment.

In one treatment protocol that may be implemented in embodiments such as FIG. 12, an aspiration catheter may be used as a first option for treatment of a lesion. Accordingly, in block 1204, an aspiration catheter is inserted into vasculature until located proximate to the invasive probe of the guidewire and thus located proximate to the lesion. In some embodiments, a guidewire may not be inserted first, but rather the aspiration catheter may be inserted in block 1202 until positioned proximate to the lesion. In such a case, the sensor may be a component of the aspiration catheter. Embodiments are not limited in this respect.

In block 1204, following placement of the aspiration catheter proximate to the lesion, the aspiration catheter is operated to attempt to aspirate the lesion into the catheter. Following a time, the sensor of the guidewire and/or aspiration catheter may be operated to determine whether the aspiration catheter is having an effect on the lesion. Some lesions, such as hard lesions, may not be able to be aspirated using an aspiration catheter. For these lesions, other interventions (such as a stent-retriever) may be used. Accordingly, in block 1204, in addition to operating the aspiration catheter to attempt to aspirate, the sensor may be operated to determine whether a change has been seen in the lesion. This may be done, for example, by positioning the sensor within the lesion prior to a start of aspiration, such as at a portion of the lesion closest to the aspiration catheter, and determining after a time whether the value output by the sensor indicates that the sensor is no longer in contact with the lesion (and is rather, for example, in contact with blood).

If during (and potentially as a result of) operation of the aspiration catheter the sensor no longer contacts the lesion, a determination may be made in block 1206 that the lesion is aspirating. In this case, a treatment recommendation may be generated and output indicating that the aspiration catheter appears to be successfully treating the lesion and that continued operation of the aspiration catheter is recommended. In the example of FIG. 12, the process 1200 then ends. It should be appreciated, however, that in some embodiments successive determinations may be made over time for whether the aspiration catheter is continuing to successfully treat a lesion, such that a change may be recommended if appropriate or that a determination may be made of when a lesion has been fully aspirated.

If, however, the value output by the sensor is not changing during the aspiration and indicates that the aspiration is not having an effect on the lesion, a treatment recommendation may be generated and output that an aspiration catheter is no longer recommended and that instead, another treatment option is recommended. In the example of FIG. 12, a second option for treatment of a lesion may be a stent-retriever. Accordingly, in block 1208, a recommendation to use a stent-retriever may be output. In block 1210, the stent-retriever may be operated to treat the lesion by removing it with the stent-retriever. For example, the stent-retriever may be inserted until located proximate to the lesion. In some embodiments, as discussed above, the sensor with which a detection is made may be a component of a guide wire, separate from a treatment device. In such a case, the stent-retriever may be inserted along the guide wire (or inserted along a micro-catheter inserted along the guidewire, following removal of the guidewire), following removal of the aspiration catheter, until the stent-retriever is positioned proximate to the lesion. As another example, the sensor may be integrated with the stent-retriever and may detect when the stent-retriever is located proximate to the lesion. The medical device, through a value produced using the sensor, may generate a treatment recommendation regarding positioning of the stent-retriever for removal of the lesion. For example, the sensor may be used, as discussed above, to detect when an invasive probe has traversed a lesion and a distal end of the invasive probe is located on a far side of the lesion. It may be best to position a stent of a stent-retriever across a lesion, such that one end of the stent protrudes beyond the lesion, to aid in ensuring that a lesion is fully captured with a stent. Accordingly, by operating a sensor to detect a far side of a lesion, and recommending that a stent-retriever be inserted until the stent or sensor extends through the lesion, a treatment recommendation may be made regarding proper positioning of a stent.

Once the stent-retriever is operated to remove the lesion in block 1210, the process 1200 ends.

Figure 13:
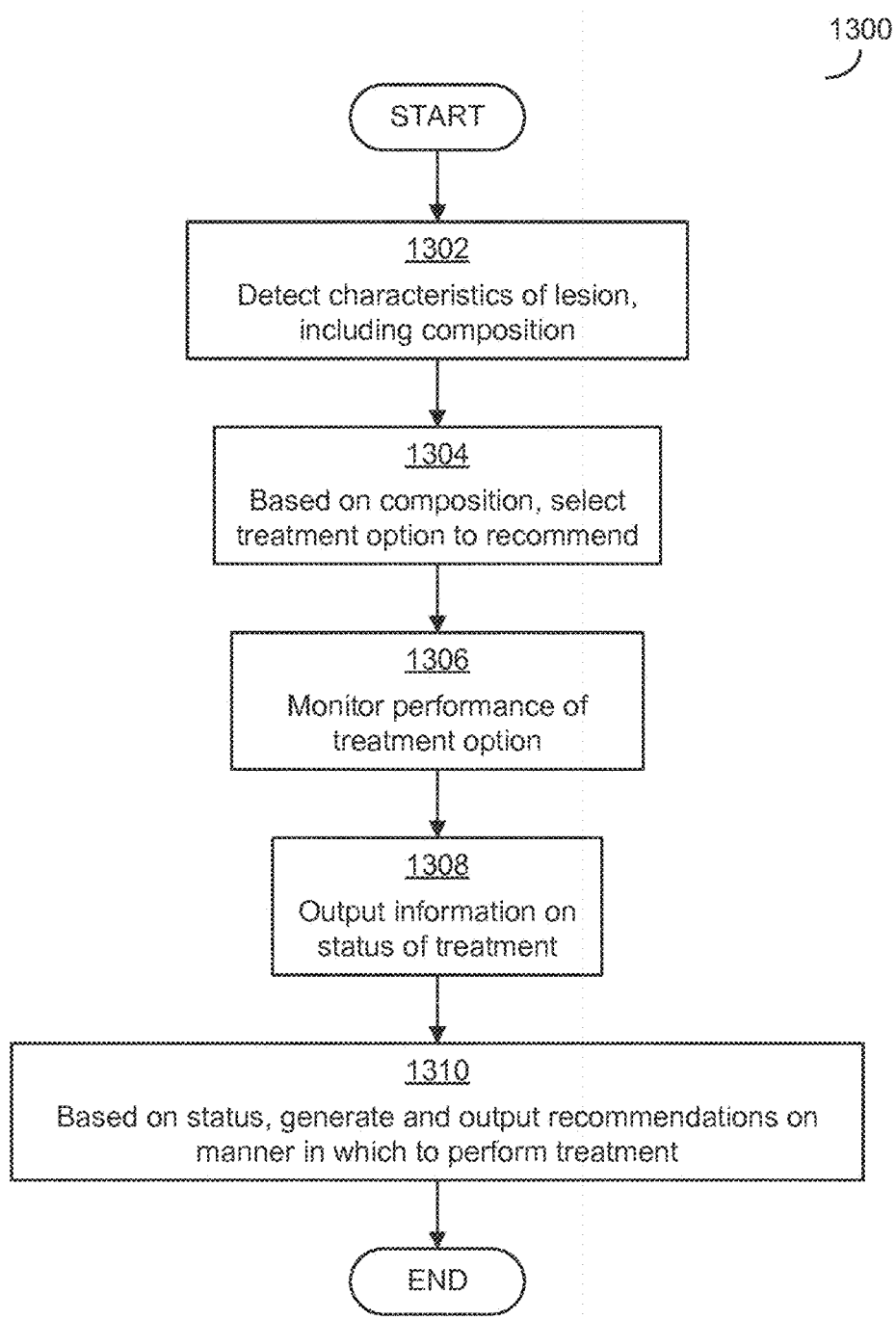
FIG. 13 is a flowchart of another illustrative method of some embodiments for operation of medical device in accordance with embodiments described herein to generate treatment recommendations based in part on a composition of a lesion.

FIG. 13 illustrates an example of a manner of operating a medical device to generate treatment recommendations for a lesion in accordance with another embodiment. In the embodiment of FIG. 13, an invasive probe may include multiple sensors arrayed along an exterior of a probe, such as in the example of FIG. 3 discussed above. As should be appreciated from the foregoing, with such an array of sensors, several different characteristics of a lesion may be determined, including composition of the lesion. The composition of the lesion may indicate different biological materials present in the lesion, such as different tissues or cells, or other biological materials such as plaque materials. In some such embodiments, for example, each sensor (e.g., the two electrodes of each sensor) may contact biological materials of the lesion, with some sensors contacting different biological materials of the lesion than do other sensors. Each sensor may then be operated, in accordance with techniques described herein, to determine an impedance spectrum of the biological material contacted by the sensor. This set of impedance spectra may then be used to determine a composition of the lesion, such as by identifying different biological materials present in the lesion. This composition information may be similar to the information that may be determined from performing a histology on the lesion. From the different impedance spectra for the lesion, and/or an identification of the different biological materials present in the lesion (e.g., the different tissues or plaque materials), characteristics of the lesion as a whole may be determined, such as by identifying (e.g., diagnosing) a type of the lesion.

For example, by performing an EIS process on the different biological materials of the lesion, it may be determined whether any of the following cells or tissues are present in the lesion: platelets, fibrins, thrombi, red blood cells, white blood cells, smooth muscle cells, elastic fibers, external elastic membrane, internal elastic member, loose connective tissues, endothelial cells, or any other tissue of a tunica intima, media or externa. In addition, by performing an EIS process on the lesion, the relative amount of each of the present cells or tissues may be determined. As a simple example, it may be determined that a lesion is composed by 50% red blood cells, 30% fibrin and 20% platelets. From this information, the lesion may be categorized as one particular type of lesion from a set of lesions, such as by diagnosing the lesion as being of one type of lesion rather than other types of lesions.

The process 1300 of FIG. 13 begins in block 1302, in which an invasive probe of a medical device is inserted into vasculature of an animal subject and operated to detect one of more characteristics of a lesion, including a composition of a lesion. Based on the characteristics, including the composition, the medical device may in block 1304 select a treatment option to recommend. The medical device may select the treatment option in any suitable manner, including according to a technique described below in connection with FIGS. 14-15B.

The treatment option that is selected may be selected based on a composition of the lesion. For example, if a composition of the lesion indicates that it is composed of smooth muscle tissue rather than a thrombus, the medical device may determine that implantation of a stent is a treatment that should be recommended. This may be because the lesion is not composed of cells/materials that may be extracted, but is instead a growth within the vessel. As another example, if the composition of the lesion indicates that it is a soft lesion, such as a soft lesion made of freshly-formed thrombus, the medical device may recommend an aspiration catheter. This may be because soft lesions are capable of being aspirated. As a further example, if the composition of the lesion indicates that it is a hard lesion, such as a hard blood clot, the medical device may recommend a stent-retriever, because it is unlikely that a hard lesion would be successfully aspirated.

Once a treatment is recommended in block 1304, the medical device may in block 1306 monitor performance of a treatment option that is selected. The medical device may monitor the treatment using one or more sensors, such as the one or more sensors with which the characteristics were determined in block 1302 or one or more sensors of a treatment device that is operated to perform the treatment. For example, in some embodiments, following the recommendation of block 1304, a clinician may insert another device into vasculature of the subject (e.g., an aspiration catheter, stent-retriever, etc., as appropriate) and the other device may include an invasive probe have an arrangement of sensors as described herein. In such an embodiment, the medical device may monitor the performance of the treatment using the sensors of the invasive probe of the other device.

The monitoring of the treatment in block 1306 may produce information regarding a status and/or progress of a treatment. For example, if the treatment is being performed with an aspiration catheter, the monitoring may produce information on an extent to which a lesion has been aspirated, and/or a remaining amount of the lesion to be aspirated. The progress may be monitored, for example, by the medical device periodically or occasionally inflating a structure (e.g., the stent-like mesh of FIG. 3) to contact a remaining portion of the lesion with sensors, to determine an extent of the lesion that remains. After the determination is made, the structure may be removed to continue aspiration of the lesion. If, on the other hand, the treatment is being performed with a stent-retriever, the monitoring may produce information on an extent to which a stent has coalesced with a lesion during inflation of the stent. For example, by monitoring sensors along an exterior of the stent (e.g., with an arrangement of sensors on a stent like the example of FIG. 3), a determination may be made of whether each portion of a stent corresponding to each sensor is fully expanded into a lesion. This determination may be made in any suitable manner, including by monitoring a change over time in values produced by each sensor and determining when a value for each sensor stops changing. When each sensor stops changing value, this may indicate that there has been no further change in an interaction between a lesion and a stent and, as such, the stent is fully expanded into the lesion and the lesion is coalesced around the stent.

Making such determinations may aid in performance of a treatment of a lesion. Accordingly, in block 1308, information on a status of a treatment is output by the medical device via a user interface, for presentation to a clinician. In addition, in block 1310, the medical device may generate one or more treatment recommendations on a manner in which to perform the treatment. For example, when the medical device determines that a lesion is fully coalesced with a stent during operation of a stent-retriever, as discussed above, the medical device may output a treatment recommendation that extraction of the stent begin.

Once the treatment is successfully performed, the process 1300 ends.

While an example of monitoring a treatment is given in the context of generating treatment recommendations, it should be appreciated that similar techniques may be used to raise error messages or other messages to a clinician regarding a status of a treatment. For example, if a sensor on a treatment device indicated presence of the lesion for a time, after which the sensor no longer detects the lesion, the medical device may determine that the treatment device is improperly positioned or that the lesion was lost. This may indicate either that the device needs to be repositioned or, potentially more problematically, that the lesion has become an embolism. A message to the clinician via the user interface may indicate such a potential problem.

Additionally, while the example of FIG. 13 described a manner of operating a medical device to provide treatment recommendations both relating to an initial selection of a treatment and related to a subsequent manner of performing that treatment, it should be appreciated from the foregoing that embodiments are not so limited. For example, in some embodiments, a medical device may include one or more sensors as described herein and may be operated to produce treatment recommendations on a manner of operation of that device, without generating an initial recommendation to use that device. For example, a stent-retriever or aspiration catheter, as discussed above, may include one or more sensors to generate data on a status or performance of a treatment and may produce treatment recommendations. As another example, a guidewire for treatment of a Chronic Total Occlusion (CTO) may generate information on a tissue/material contacted by a sensor and generate treatment recommendations. In a CTO procedure, the guidewire may be inserted through smooth muscle tissue or the plaque of a blood vessel when a solidified thrombus cannot be penetrated. Treatment recommendations may be made, based on sensed characteristics of tissue/material contacted by a sensor, of when a guidewire is positioned against the smooth muscle tissue and can be advanced and when the guidewire has been advanced through the endothelial tissue and is once again within the blood vessel, on a far side of the lesion. In addition, in some embodiments, one or more measurements may be taken of a thickness of smooth muscle tissue or other characteristics of the vessel wall that may be informative of a risk that the guidewire will puncture the tissue rather than navigate through the tissue. For example, if a measurement indicates a thinning of the smooth muscle tissue on one side of an invasive probe of the guidewire, this may indicate that the invasive probe is at risk of puncturing the vessel wall. A treatment recommendation may be made to proceed more slowly and/or to withdraw the guidewire, or another recommendation may be generated.

Figure 14:
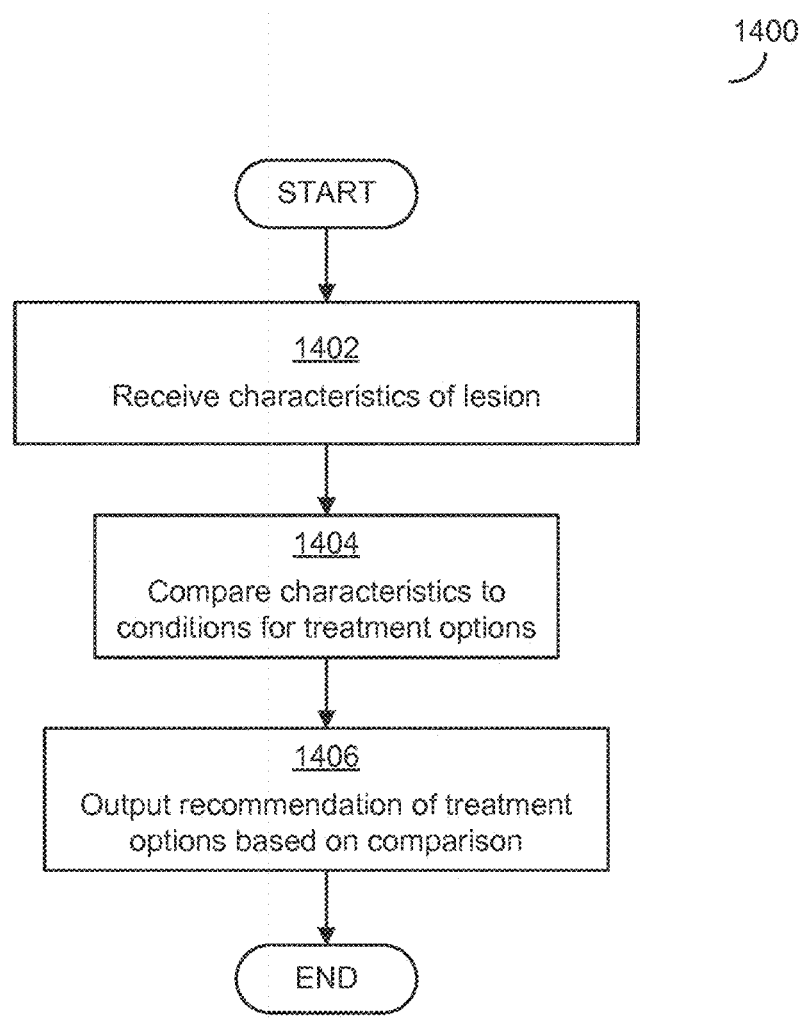
FIG. 14 is a flowchart of an illustrative manner of generating treatment recommendations using conditions, which may be implemented in some embodiments.

Those skilled in the art will appreciate from the discussion herein that there are a variety of ways in which a medical device may be configured to generate treatment recommendations based on characteristics of a lesion and/or a status of a treatment. FIGS. 14-15B illustrate one example of a technique that may be used for generating treatment recommendations.

FIG. 14 illustrates a process 1400 that may be implemented by a medical device in some embodiments for generating treatment recommendations.

The process 1400 begins in block 1402, in which the medical device receives one or more characteristics of a lesion. The medical device may receive the characteristic(s) from a component of the medical device, such as in a case that the characteristic(s) are determined using one or more sensors included in an invasive probe of the medical device and/or by another component (e.g., a lesion analysis facility) that generates characteristic(s) based on data produced by the sensors. The characteristic(s) may include a composition of the lesion, in some embodiments. The characteristic(s) may additionally or alternatively include a location of the lesion within the body, one or more dimensions of the lesion (e.g., a length, a thickness, etc.), a temperature of the lesion, or other information that may be determined based on the types of sensors described above.

In block 1404, the medical device compares the characteristic(s) received in block 1402 to one or more conditions for one or more treatment options. The medical device may be configured with information on multiple different available treatment options, each of which may be associated with one or more conditions that relate to one or more characteristics of lesions. For example, the medical device may be configured with one or more conditions for treatment of a lesion by implantation of a stent, one or more different conditions for use of an aspiration catheter, and one or more further different conditions for use of a stent-retriever. Examples of such conditions related to a composition of a lesion are described above in connection with FIG. 13.

The medical device may compare the characteristic(s) of the lesion to the conditions to determine which conditions are met. In some embodiments, the sets of conditions for treatment options may be mutually exclusive, such that a lesion may meet only one set of conditions and thus only one treatment option may be selected. In other embodiments, the set of conditions may not be mutually exclusive, and the medical device may determine which treatment option to recommend by identifying the one for which the most corresponding conditions are met or the one for which the corresponding conditions are met most closely (e.g., in the case that a condition is associated with a range of values, the condition for which a value most closely matches the range by, for example, falling in a middle of the range).

In block 1406, based on the comparison, the medical device may output a recommendation of a treatment option via a user interface of the medical device, and the process 1400 ends.

While the process 1400 is described in connection with generating an initial treatment recommendation for a treatment of a lesion based on characteristics of a lesion, those skilled in the art will understand how to extend the technique to generation of treatment recommendations during performance of a treatment, as described above in connection with block 1310. For example, in some embodiments, based on comparison of characteristics of a lesion (e.g., composition of the lesion) to one or more conditions for certain parameters of a treatment, such as a speed at which to extract a stent of a stent-retriever, the medical device may output recommendations on such parameters.

Those skilled in the art will appreciate that there are a number of ways in which to set the conditions for treatment options that may be used in connection with a process like process 1400 of FIG. 14. For example, values for characteristics of a lesion to use as conditions may be hard-coded into a medical device following at least some experimentation to determine a correspondence between the values, types of lesions, and successful treatment with various treatment options. The inventors have recognized and appreciated, however, the advantages of a system to learn such relationships and conditions based on characteristics of lesions and information on successful treatments of lesions, among other information. For example, a machine learning process, such as one that may include feature extraction and/or classification, may be implemented in some embodiments.

Figure 15A:
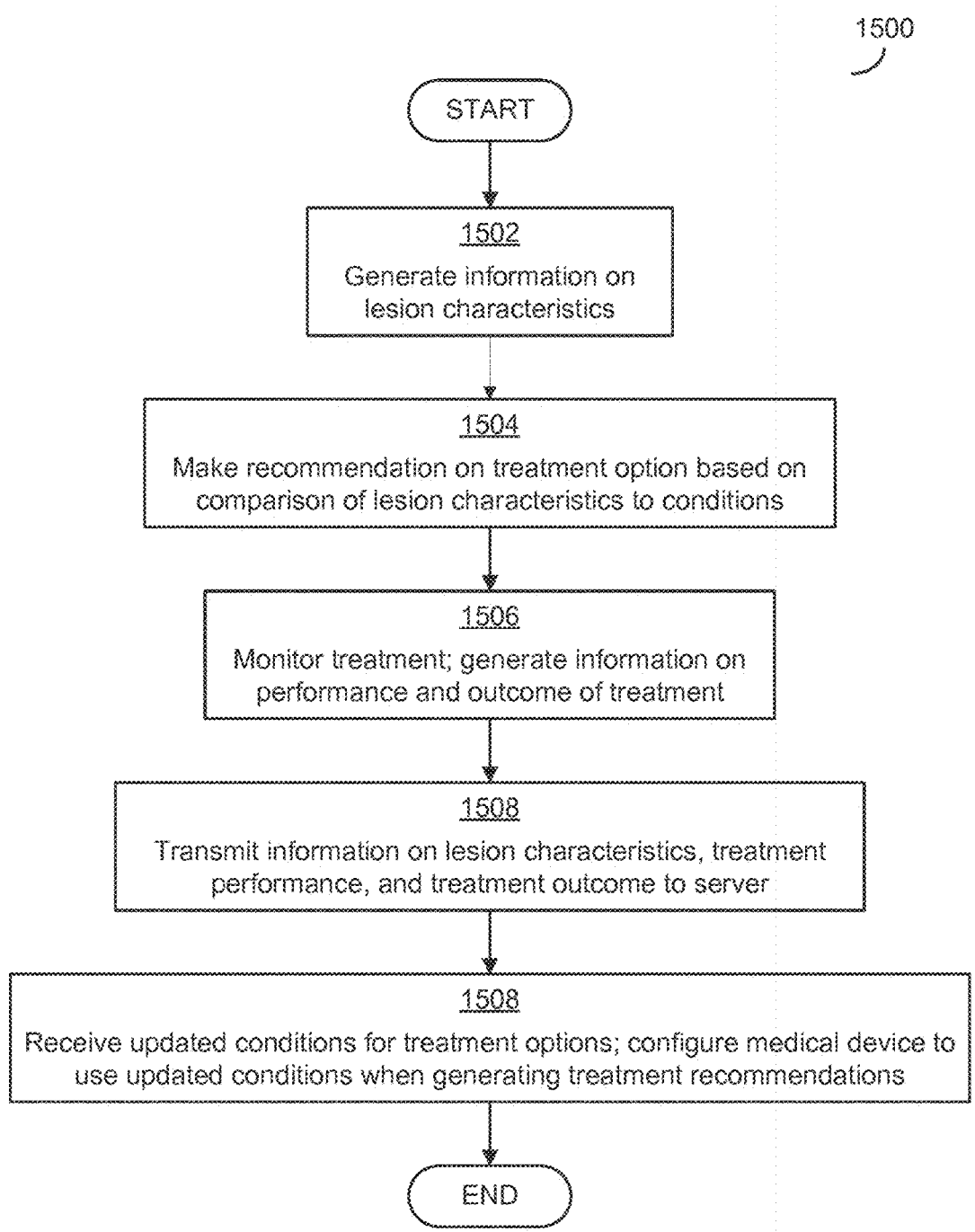
FIGS. 15A-15B are flowcharts of illustrative processes for operating a server to analyze reports on treatments to determine conditions with which to configure medical devices, which may be implemented in some embodiments.
Figure 15B:
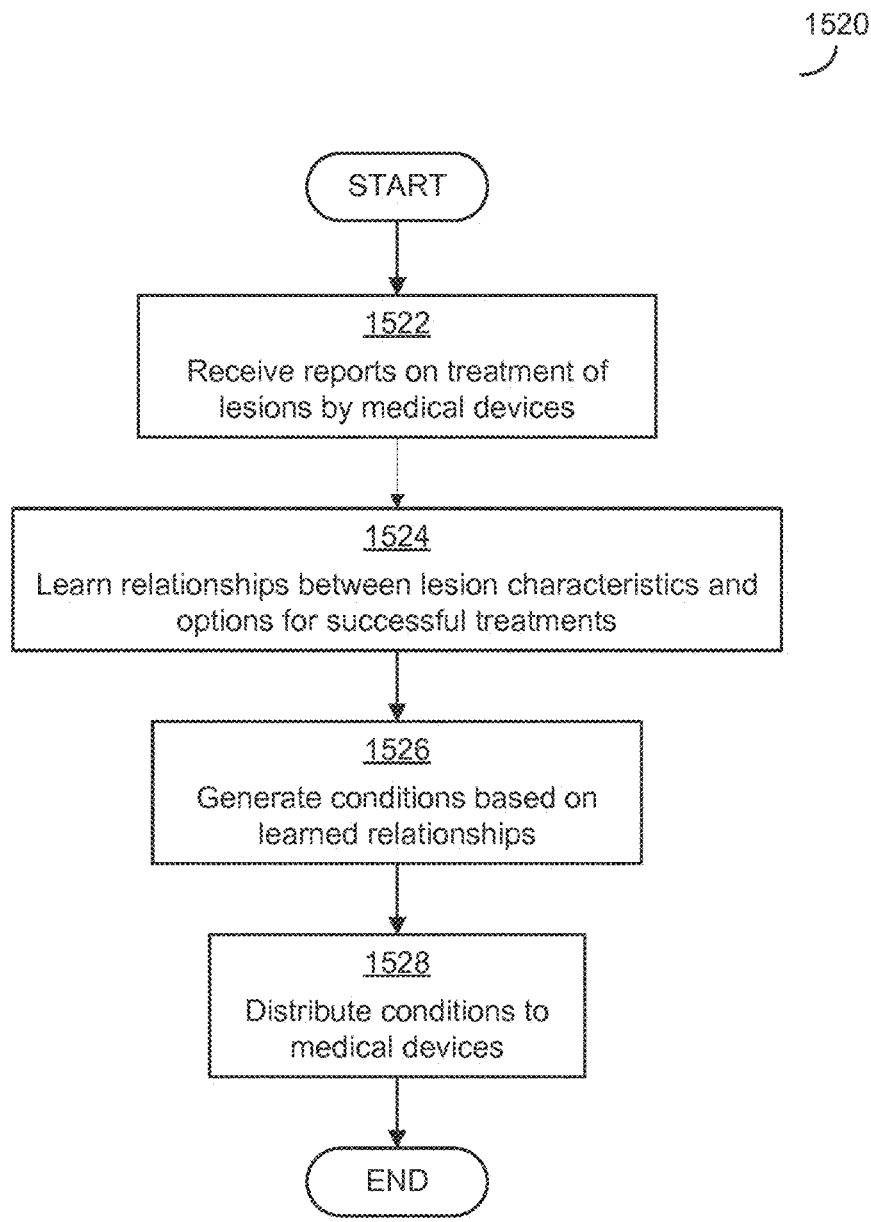

FIGS. 15A-15B illustrate an example of a machine learning process that may be performed in some embodiments. FIG. 15A illustrates a process that may be implemented by a medical device, whereas FIG. 15B illustrates a process that may be implemented by a computing device (e.g., a server) in communication with multiple different medical devices.

The process 1500 of FIG. 15A begins in block 1502, in which a medical device generates information on characteristics of a lesion. In blocks 1504 and 1506, the medical device may make recommendations on treatment options based on a comparison of lesion characteristics to conditions for treatment options as well as monitor a progress of a treatment and generate status information throughout the treatment. These operations of blocks 1502-1506 may be implemented similar to the manner described above in connection with FIGS. 13-14 and thus, for the sake of brevity, will not be described further. In addition, in block 1506, the medical device may generate information on an outcome of a treatment. The outcome of the treatment may indicate whether a lesion was successfully treated, whether the lesion was dislodged and released into the subject's body, whether multiple treatments were necessary, or other information indicating an outcome. The information indicating the outcome may be generated using sensors of the medical device, as should be appreciated from the foregoing. For example, using data generated by an accelerometer in a handle of the medical device, the medical device may determine whether it was operated multiple times to remove a lesion. As another example, as discussed above, if a sensor was detecting a lesion then stopped detecting the lesion, this may be an indication that the lesion has moved in the subject, including that the lesion was dislodged and became an embolism.

In block 1508, the information generated in blocks 1502-1506 is transmitted from the medical device, via one or more wired and/or wireless communication connections and/or networks, including the Internet, to a computing device. The computing device may be, in some embodiments, geographically remote from the medical device. In block 1508, following the transmission in block 1506, the medical device receives from the computing device (such as via the network(s) via which the information was transmitted in block 1508) one or more updated conditions for treatment options. The updated conditions may identify new values for evaluation of conditions with respect to characteristics of lesions. The medical device may configure itself to apply the one or more updated conditions for generation of treatment recommendations, such as through considering the one or more updated conditions in the context of a process like the one discussed above in connection with FIG. 14. Once the medical device is configured with the updated conditions, the process 1500 ends.

FIG. 15B illustrates a process that may be implemented by a computing device to perform a learning process on reports on treatments of lesions, to generate conditions for use in selecting treatment recommendations such as via a process like the one discussed above in connection with FIG. 14. Specifically, in the example of FIG. 15B, a computing device analyzes reports on treatments of lesions, in connection with information regarding characteristics those lesions, to identify relationships between successful (and/or unsuccessful) treatments and characteristics of lesions. Through identifying such relationships, conclusions may be drawn about which treatment options are best for particular types of lesions and, based on those conclusions, a treatment recommendation may be generated for treatment of a particular lesion based on characteristics of that lesion, as in the example of FIG. 14. Similarly, as discussed above, based on information regarding status or performance of a treatment, recommendations on a manner of performing a treatment (e.g., a time at or speed with which to extract a stent during a stent-retrieval) may be determined. While the example of FIG. 15B will be described in context of generating conditions for an initial selection of a treatment option to use for a lesion based on characteristics of a lesion, those skilled in the art will understand from the description below how to extend the technique for use with generating recommendations on a manner in which to perform a treatment.

The inventors have recognized and appreciated that the generation of such conditions and the identification of relationships between successful/unsuccessful treatments and characteristics of lesions may be advantageously determined using a machine learning process. Various machine learning algorithms are known in the art and may be adapted for use in this context. Some machine learning algorithms may operate based on feature extraction and classification techniques, in which groups (classifications) for units are identified and an analysis of properties of units is carried out to determine which properties, and/or values of those properties, most closely correspond to or predict correct membership in the groups. Based on these identified properties, subsequently-received unclassified units having such properties can be "classified" into one of the groups/classifications based on a comparison of the properties and/or values of the properties of the unclassified unit to the properties/values for each group. In some machine learning applications, the groups/classifications may be identified manually during a configuration of the machine learning process. In addition, or in others, the groups/classifications may be determined or adjusted over time by the machine learning process, such as through creation of new groups/classifications when the machine learning process perceives through its analysis that a new grouping may better characterize some units. A full discussion of machine learning is outside the scope of this document and not necessary for an understanding of techniques described herein. Those skilled in the art will understand how to implement a machine learning technique for use with information and goals described herein.

Here, groups may be defined as treatment options or treatment outcomes, and the example of FIG. 15B will be described in this context. In this case, the groups may be defined by characteristics of lesions and/or statuses of treatment. In this case, when characteristics of a lesion and/or of a status of treatment match characteristics for group, the corresponding treatment option may be selected for output. Additionally or alternatively, in some embodiments groups may be associated with different types of lesions (each type having one or more characteristics or ranges of characteristics different from the other types) and/or status of treatment, and these different groups may then be associated with particular treatment options or ways in which to operate a treatment device. In this latter case, when characteristics for a particular lesion or status of a treatment match a group, the corresponding treatment recommendation(s) for the group may be selected for output.

The process 1520 of FIG. 15B begins in block 1522, in which a learning facility executing on one or more computing devices receives, over time, multiple reports on treatment of lesions by medical devices. The medical devices may be medical devices operating in accordance with embodiments described above. The reports may include information on a lesion that was treated, such as one or more characteristics of the lesion. The report may also include information on a manner in which a lesion was treated, such as on one or more treatment devices that were operated to treat the lesion and the manner in which those lesions were treated. Information on an outcome of the treatment may also be included in a report, such as whether a treatment was successful, whether multiple treatments were necessary, whether a lesion was dislodged and became an embolism, or other outcomes.

The reports may contain information determined by one or more sensors of a medical device, including examples of sensors and types of information described above. As discussed above, various types of sensors may be included in embodiments, including one or more electrical, mechanical, optical, biological, or chemical sensors. Specific examples of such sensors include inductance sensors, capacitance sensors, impedance sensors, EIS sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors. It should be appreciated that various types of characteristics or other information may be generated from these sensors. Any of this information may be included in reports and used in the process 1520 for generating conditions associated with treatment recommendations. For example, as discussed above, an accelerometer disposed within a handle of a medical device may track movements of the medical device and be used to determine whether multiple treatments were performed to treat a clot. As another example, a force sensor may indicate a force with which a stent-retriever is extracted or a set of impedance sensors may determine, based on whether a detected impedance at one or more sensors of a stent of a stent-retriever varies over time during an extraction, whether a lesion is partially or fully separating from the stent during retrieval. Those skilled in the art will appreciate from the discussion above different types of data that may be generated by sensors of a medical device for inclusion in such reports.

Reports may also include information that may be entered by a clinician or retrieved from another system with which the medical device may interoperate. For example, the report may include information on a position of a lesion within anatomy of the subject, such as whether the lesion is in a cranial artery, femoral artery, pulmonary vein, common bile duct, or other duct. This information may be entered by the clinician via a user interface or, for example, retrieved from another system such as an angiogram device.

Optionally, the reports may include information about the patients, such as age, medical history and demographic.

The reports that are received in block 1522 may be received over time from a plurality of medical devices, which may be geographically distributed. By receiving these reports, and the contents of these reports, over time a set of conditions and treatment recommendation that define recommended or best practices may be generated.

Accordingly, in block 1524 the learning facility analyzes the information in the reports to identify relationships between lesion characteristics (and/or manners of operating treatment devices), options for treating lesions having those characteristics, and successful treatments. Based on this analysis, the learning facility may learn relationships between these pieces of information. Such relationships may indicate when certain treatment options are successful or not successful, or for which types of lesions different treatment options are successful or not successful. In at least some of the embodiments in which information about the patients are obtained, the learning facility may learn relationship between lesion characteristics, options for treating lesions having those characteristics, and successful treatments based on the patients' information. The model may be trained to learn which particular piece of information, among all the information obtained about patients, is likely to affect the probability of success of a treatment. For example, the trained model may identify that a particular treatment is likely to have different probabilities of success depending on the age of the patient, even if all the characteristics of the lesion are equal. As such, different treatment recommendations may be provided for two patients having identical lesions but different age. As another example, the trained model may learn that some treatments, when applied to subjects who have suffered a certain condition in the past, are less likely to succeed relative to subjects who have not suffered such a condition, even if the type of lesions are identical.

Based on this analysis in block 1524, the learning facility (through the feature extraction and classification processes of a machine learning process) may in block 1526 generate conditions for each of the treatment options. The conditions may be associated with characteristics of lesions, so as to indicate different characteristics or ranges of characteristics for lesions that may be successfully treated with each treatment option. For example, conditions may relate to a range of values for a visco-elastic property of a lesion, such that a visco-elasticity in one range may be associated with treatment using an aspiration catheter and visco-elasticity in another range may be associated with treatment using a stent-retriever. In this manner, when a lesion having a specific visco-elasticity is detected, a comparison to these conditions may be used (as in the process of FIG. 14) to determine which treatment option to recommend for that particular lesion.

In block 1528, once the conditions are generated in block 1526, the conditions may be distributed to medical devices such that the devices may be configured to use those conditions to generate treatment recommendations, as discussed above in connection with FIG. 15A. Once the conditions are distributed, the process 1520 ends.

While the process 1520 is discussed in FIG. 15B as a discrete process, it should be appreciated that in some embodiments the reception of reports and determination of conditions may be a process that is repeated over time, including continuously or at discrete intervals. Accordingly, in some embodiments the process 1520 may be performed multiple times or, following distribution of conditions in block 1528, the learning facility may return to block 1522 to receive additional reports and continue the learning process.

In some alternative embodiments, generation of treatment recommendations may be performed, using machine learning techniques, directly based on measurement data obtained from one or more sensors of the types described above. Being directly based on measurement data, the generation of treatment recommendation may be performed without having to first characterize or identify the lesion or the type of lesion. Compared to other approaches in which measurement data are used to identify the nature (such as the type or composition) of the lesion, and subsequently identify a suitable treatment recommendation, this approach makes it possible to skip an intermediate step of characterizing the lesion. This may reduce the time and/or computational resources needed to generate a treatment recommendation.

Figure 15C:
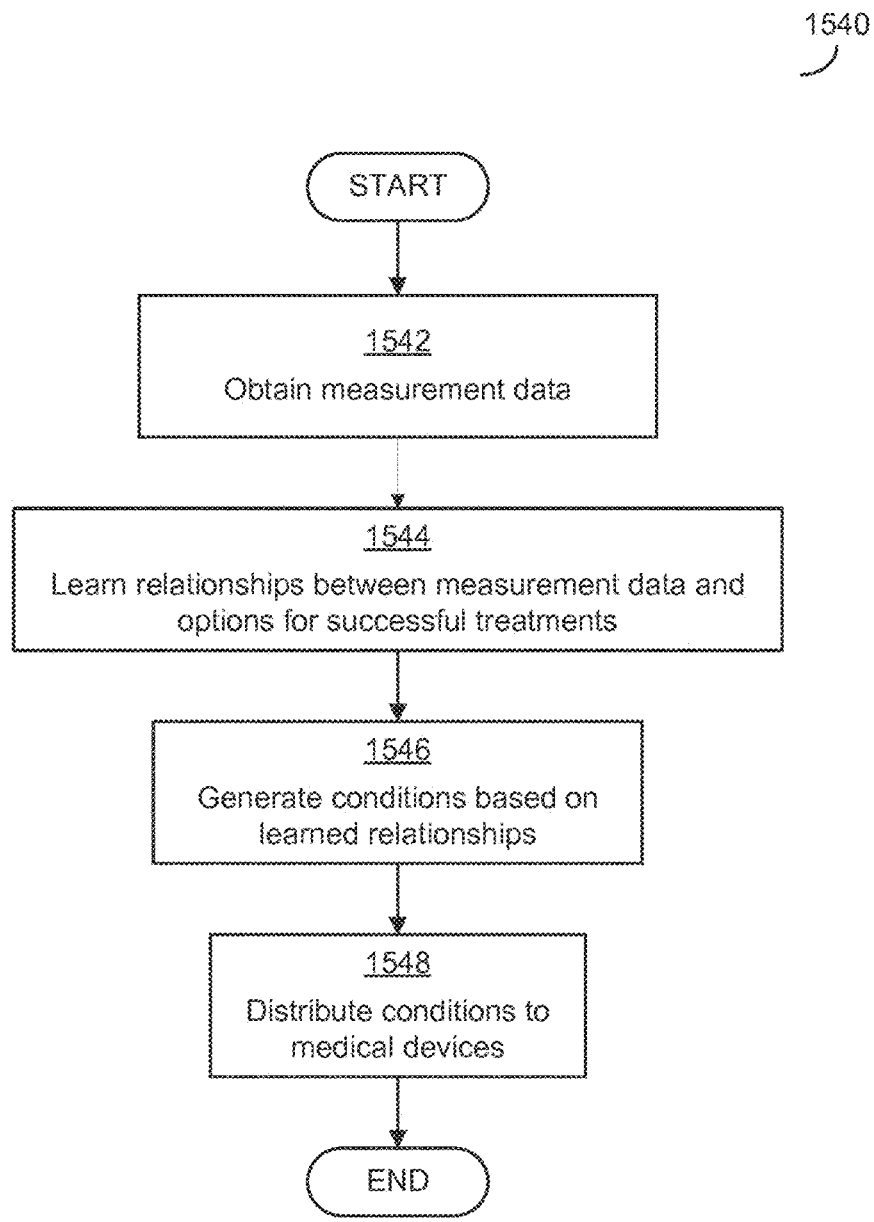
FIG. 15C is a flowchart of an illustrative process for operating a server to learn relationships between raw data and options for successful treatments, which may be implemented in some embodiments.

FIG. 15C illustrates a process that may be implemented by a computing device to perform a learning process on reports on treatments of lesions to generate conditions for use in selecting treatment recommendations. The conditions may relate to EIS measurements, and/or features determined from EIS measurements (e.g., features present in the measurements and/or derived features). The process of FIG. 15C may be used to train a model to identify one or more relationships between the EIS measurements or features and treatments for lesions to which the measurements/features relate. Training the model in this manner, with relationships(s) between measurements/features and treatments, may allow for generation of recommendations on a treatment for a lesion without needing to diagnose or identify the lesion.

The process 1540 of FIG. 15C begins in block 1542, in which a learning facility executing on one or more computing devices receives, over time, reports including measurement data obtained using the techniques described herein. Examples of measurement data include, but are not limited to, EIS measurements. Each set of data may include any suitable number of EIS samples, each of which may represent impedance information obtained at a specific frequency. As such, each set of measurements may be interpreted as the spectral response of a particular type of lesion. In certain cases, measurement data obtained via sensors other than impedance sensors may be used in process 1540. Examples of such sensors include inductance sensors, capacitance sensors, Electrical Impedance Tomography (EIT) sensors, pressure sensors, flow sensors, shear stress sensors, mechanical stress sensors, deformation sensors, temperature sensors, pH sensors, chemical composition sensors (e.g. $O_2$ ions, biomarkers, or other compositions), acceleration sensors, and motion sensors.

The measurements that are received in the report may include measurements taken when the sensor(s) initially contacted the lesion, or otherwise during a phase of a diagnosis or treatment when measurements are being collected for the lesion. Such measurements could be used, in accordance with techniques otherwise described herein, to identify or diagnose the lesion. The measurements may additionally or alternatively include measurements collected during a treatment, such as during an extraction of a lesion using a stent-retriever or during another procedure.

The report may also include information on a manner in which a lesion was treated, such as on one or more treatment devices that were operated to treat the lesion and the manner in which those lesions were treated. Information on an outcome of the treatment may also be included in a report, such as whether a treatment was successful, whether multiple treatments were necessary, whether a lesion was dislodged and became an embolism, or other outcomes.

The reports that are received in block 1542 may be received over time from a plurality of medical devices, which may be geographically distributed. By receiving these reports, and the contents of these reports, over time a set of conditions and treatment recommendation that define recommended or best practices may be generated.

Accordingly, in block 1544 the learning facility analyzes the information in the reports to identify relationships between measurement data, options for treating lesions exhibiting the characteristics represented in the measurement data, and successful treatments. Based on this analysis, the learning facility may learn relationships between these pieces of information. Such relationships may indicate when certain treatment options are successful or not successful, or for which types of lesions different treatment options are successful or not successful.

Based on this analysis in block 1544, the learning facility (through the feature extraction and classification processes of a machine learning process) may in block 1546 generate conditions for each of the treatment options. Blocks 1546 and 1548 may operate substantially in the same manner as blocks 1526 and 1528 of FIG. 15B.

It should be appreciated that, as discussed elsewhere herein, an embodiment that generates a treatment recommendation based on impedance measurements, in accordance with FIG. 15C, may generate a treatment recommendation that is a recommendation of a treatment option to use from among a set of treatment options (e.g., different tools to use), a recommendation of a manner in which to perform that treatment option (e.g., a manner in which to operate a tool, generated before and/or during execution of the treatment), or recommendation not to treat, among other types of recommendations.

Figure 16:
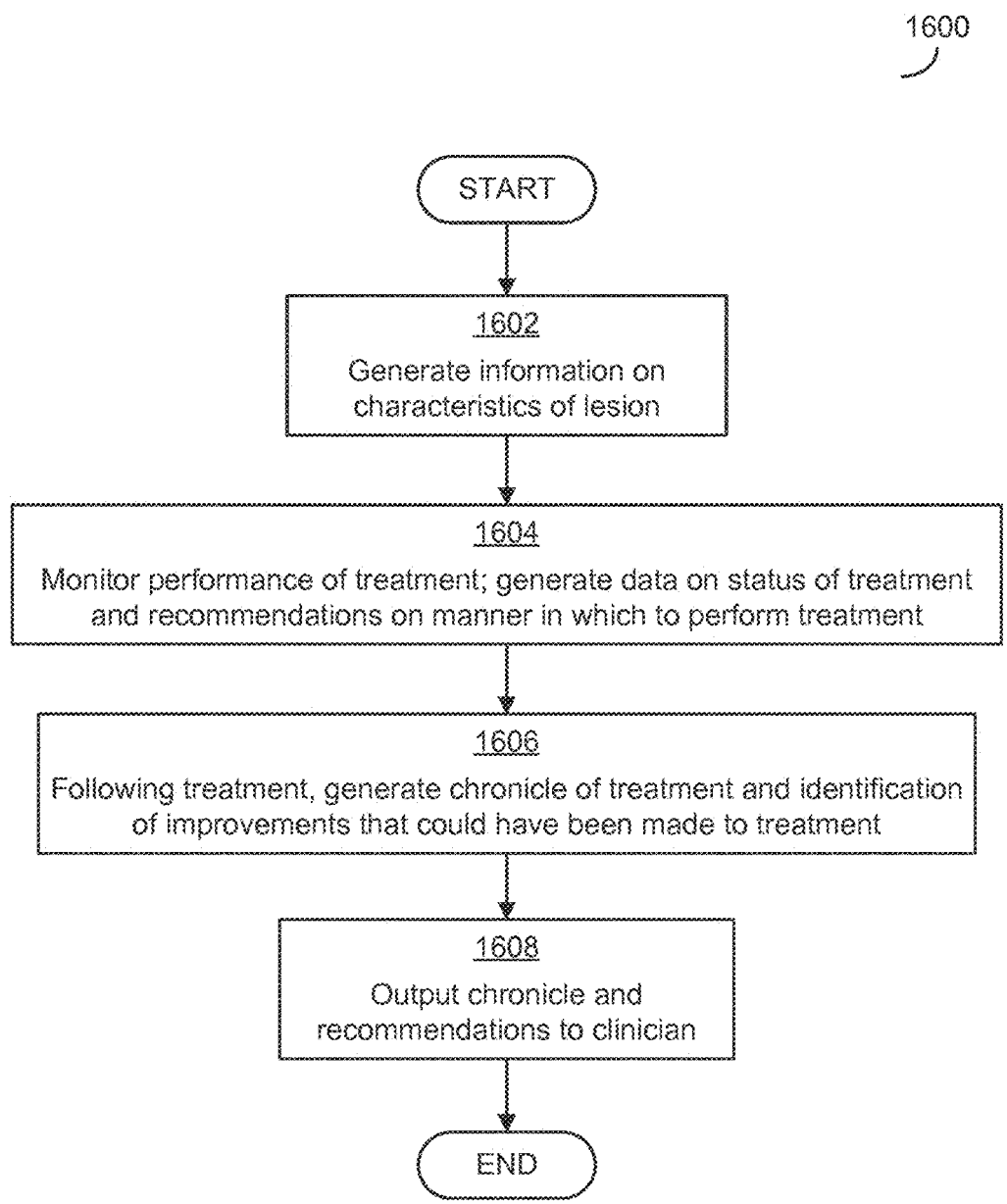
FIG. 16 is an example of a process that may be implemented in some embodiments for generating a chronicle of a treatment.

Examples are provided above of devices and processes for providing feedback to a clinician during a diagnosis and/or treatment of a lesion, including providing treatment recommendations during the diagnosis and/or treatment. In some embodiments, in addition to or as an alternative to providing such feedback during the diagnosis and/or treatment, a medical device may be configured to present information on a diagnosis and/or treatment to a clinician following the operation of the medical device in the diagnosis/treatment. FIG. 16 illustrates an example of such as process.

The process 1600 begins in block 1602, 1604, in which a medical device is operated to generate information on characteristics of a lesion and on performance of a treatment, and recommendations on a manner in which to perform the treatment. The operations of blocks 1602, 1604 may be similar to examples of generation of data discussed above.

In block 1606, following the treatment, the information generated in blocks 1602, 1604 is used by a chronicle generation facility to generate a chronicle of the treatment. The chronicle of the treatment may include information regarding how devices were operated over time, what characteristics of the lesion were detected, what recommendations were made by the medical device, and whether those recommendations were followed by the clinician. If an error was detected in the treatment, such as a loss of a part or entirety of a lesion that resulted in, for example, creation of an embolism or necessity of a subsequent treatment, the chronicle generation facility may analyze the error to determine a cause of the error. For example, if sensors detected at a time that a part of a lesion separated from a stent-retriever, and at an immediately-preceding time another sensor noted application of a sudden force to the stent-retriever, the chronicle generation facility may note this in the chronicle. If a force applied to a stent-retriever exceeded a maximum force recommendation from the medical device, or the medical device was operated in any other manner inconsistent with the treatment recommendation, this may be noted in the chronicle. When such information is included in the chronicle, recommendations may be made to the clinician on how to avoid the error in future procedures.

In addition, in some embodiments, the chronicle generation facility may include in the chronicle detailed information on a lesion and potential causes of the lesion, to aid a clinician in diagnosing the lesion. For example, while in some embodiments during a treatment a brief characterization of a lesion may be output (e.g., lesion is viscous), in a chronicle more detailed information on a composition may be output (e.g., lesion primarily composed of cholesterol). In addition, the chronicle generation facility may analyze the composition in context of a location of the lesion in the subject to determine whether the lesion was, for example, a result of an injury, a thrombus that developed at the site of the lesion, or an embolism that became stuck at the site of the lesion. For example, if the lesion is primarily composed of tissue like smooth muscle cell or atheroma, the lesion may have been a growth at the site following an injury. As another example, if the composition of the lesion indicated it formed in an area of the anatomy having a high shear stress, but the lesion is located at an area of the anatomy having a low shear stress, this may indicate the lesion was an embolism that became stuck at the site.

Once the chronicle has been generated in block 1606, the chronicle is output for presentation to a user (e.g., via a display, or stored to a memory or transmitted via a network), and the process 1600 ends.

The inventors have further appreciated that an accuracy of techniques described herein, such as an accuracy in diagnosis and/or a degree of confidence with which treatments are recommended for intervening on particular types of lesions, would be increased with greater certainty that the data used in training a model, and the data collected for a lesion and used in diagnosing the lesion or in determining a manner in which to treat a lesion, corresponds to the lesion and not to other tissues or biological structures.

The inventors have further recognized and appreciated that, in many cases, an insertable or implantable device may, during collection of measurements, be contacting more structures than just a lesion or other biological structure of interest. Instead, it may often be the case that a probe including one or more sensors may fully or partially contact other biological structures located adjacent to or proximate the biological structure of interest. For example, if an insertable device is navigated through an animal's vasculature until it is contacting a lesion of a blood vessel, and is then operated to collect measurements for that lesion, it is possible and perhaps likely that the sensors of the probe may be contacting a vessel wall in addition to contacting the lesion. As a specific example, rather than penetrating the lesion or otherwise only contacting the lesion, in some cases the insertable device may be located between the lesion and the vessel wall, such that some sensors are contacting the lesion and others are contacting the vessel wall.

In cases in which measurements are collected for one or more other biological structures, in addition to the biological structure of interest, such measurements may impact the accuracy of techniques described herein for identifying or characterizing a biological structure, or determining an appropriate treatment for the biological structure.

The inventors have therefore developed approaches for filtering EIS measurements collected according to the methods described herein, to remove measurements not associated with a lesion or other biological structure of interest. More particularly, the inventors have appreciated that filtering the collected data to remove, or least reduce the number of, measurements that are not associated with the lesions may significantly increase the model's ability to accurately characterize lesions and/or provide suitable recommendations for treating lesions. The filtered data (without or with reduced measurements corresponding to other structures) may also be used to train a model in any of the manners described above.

The inventors have additionally recognized and appreciated that there are a range of approaches to filtering of data to remove extraneous or outlier values, and have recognized and appreciated the advantages offered by a technique that leverages machine learning to perform the filtering. In such a machine learning process, a model may be trained with EIS measurements for a biological structure for which the model will "pass" measurements, as well as EIS measurements for one or more other biological structures that may be located in an area of an animal's body in which the biological structure of interest is located and for which the model will "filter" measurements. The one or more other biological structures may be identified based on expected or predicted anatomy of various animals' bodies in an area to be probed, such as an area in which a lesion is expected to be found or probed. For example, once an area of an animal's body is identified, and a biological structure that is to be measured and/or treated is identified, during a configuration phase one or more other biological structures that may be found in that area of the animal's body, and that may be adjacent to or proximate to the biological structure of interest, are identified. Measurements may then be collected for the biological structure of interest (e.g., a particular type of lesion, such as a range of lesions of the type with a range of characteristics/compositions) and/or for one or more other biological structures in vitro. A model may then be trained based on the measurements to distinguish, for that area of the animal's body, between the biological structure of interest and one or more other biological structures.

Figure 17A:
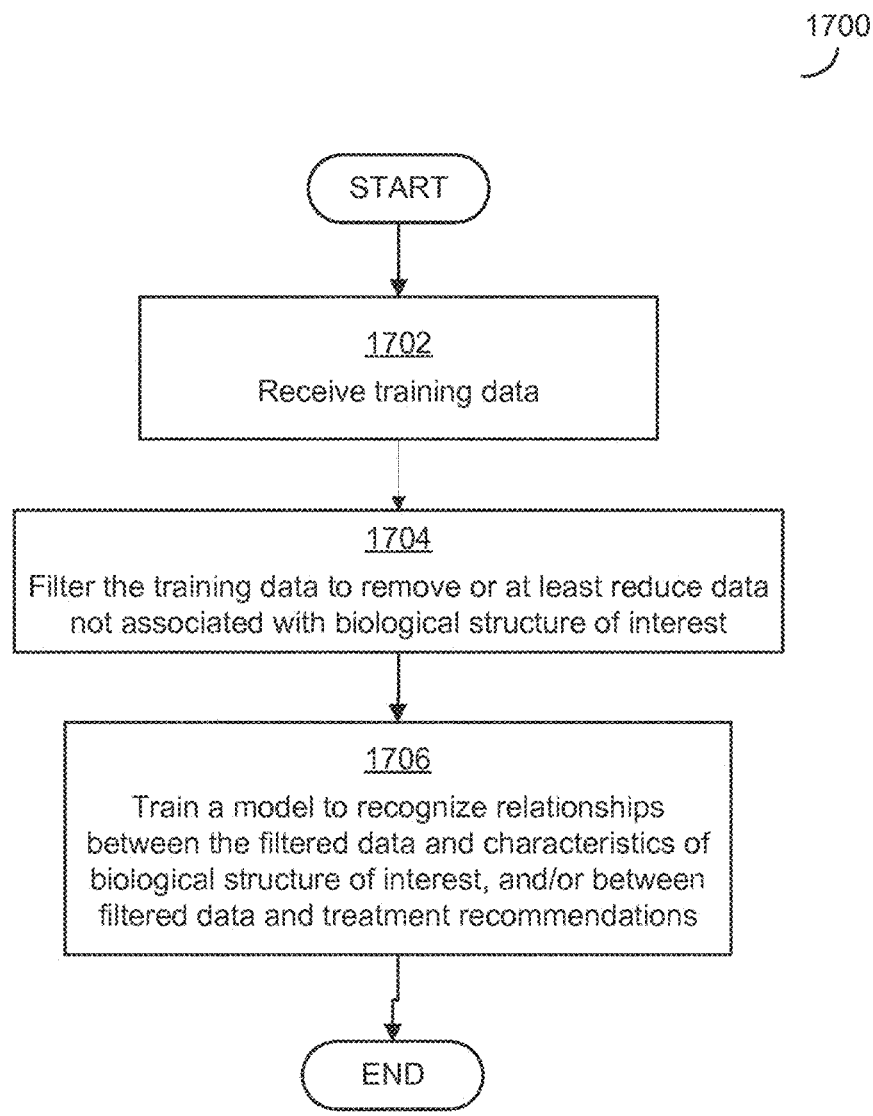
FIG. 17A is an example of a process that may be implemented in some embodiments for training a model to accurately characterize lesions and/or providing treatment recommendations.

FIG. 17A is a flowchart illustrating a process for training a model to characterize lesions and/or for providing treatment recommendations with an improved degree of confidence or accuracy, through filtering measurements that are for biological structures other than the lesion. Process 1700 begins at block 1702, in which training data are received. The training data may include measurements obtained by sampling biological materials using sensors of the types described above. The training data may be obtained using in vitro or in vivo techniques. The training data may include measurements associated with the lesions to be treated as well as measurements associated with other biological structures.

The identity of the structure to which the measurements correspond may also be input in the training, to aid the model in learning to distinguish between measurements that correspond to the biological structure of interest and other measurements.

The training of block 1702 may be carried out to train a model to distinguish between EIS measurements that are for a biological structure of interest (e.g., a particular type of lesion) and EIS measurements that are not for that biological structure. Such a model may therefore sort EIS measurements into one of two categories: "for" the biological structure of interest and "not for" the biological structure of interest. In other embodiments, rather than only training a model to distinguish between those two categories, a model may be trained with EIS measurements for each of multiple different biological structures and be trained to categorize input EIS measurements into one of those categories, to identify a biological structure to which each EIS measurement most likely corresponds.

The model may be trained in block 1702 to identify, for each particular EIS measurement, whether the EIS measurement corresponds to a biological structure of interest and/or a structure to which the EIS measurement corresponds. Accordingly, the model of block 1702 may not be trained to carry out an identification or filtering on a set of EIS measurements, but rather may process a set of EIS measurements to filter out individual EIS measurements within the set. Such a set of EIS measurements may include measurements from operation of an insertable or implantable device at a particular time, such as a collection of EIS measurements at a time at which multiple sensors of an implantable or insertable device are used. Distinguishing between measurements in this way may allow for distinguishing between EIS measurements collected, at a particular time or over a particular time interval, by a sensor in contact with a lesion or other biological structure of interest, and EIS measurements collected by another sensor of the device that is not contacting the lesion/structure but instead is contacting another biological structure.

Once a model is trained to carry out filtering in this manner, the filter may be used on training data as part of a process for training a model to identify and/or categorize a biological structure (e.g., lesion) based on EIS measurements. More particularly, at block 1704, training data is filtered to remove, or at least to reduce, the data that are not associated with a biological structure of interest, such as a particular type of lesion. At block 1708, the filtered training data may be used to train a model to recognize relationships between the filtered data and lesion characteristics (e.g., in accordance with embodiments described above in connection with FIGS. 15A-15B), or to directly recognize relationships between the filtered data and treatment recommendations (e.g., in accordance with some embodiments described above in connection with FIG. 15C). Block 1708 may be implemented using any of the processes described above.

It should be appreciated that in the embodiments in which the filter of block 1704 is trained to learn which data subsets correspond to lesions and which data do not, process 1700 may include a multi-step training model, the first training step being performed at block 1704, the second training step being performed at block 1706. In some embodiments, the filter of block 1704 and the model of block 1706 are trained concurrently, that is, as a single multi-variable problem and using the same data. In other embodiments, however, the filter of block 1704 and the model of block 1706 are trained using separate data and/or at different times.

In some embodiments, the training of FIG. 17A may be performed in accordance with techniques described above in connection with FIG. 22. As should be appreciated from the foregoing, the process of FIG. 22 includes an iterative approach to identifying frequencies at which to collect EIS measurements and features to extract from EIS measurements for use in training one or more models and/or analyzing data in connection with such a model to distinguish between tissues. In each iteration of the iterative approach, different frequencies and/or different features may be selected for use in training a model to determine whether a model trained with that input may satisfy one or more performance targets. In some embodiments, such an iterative process may also be used for training a filter model for filtering out EIS measurements that do not correspond to a biological structure of interest and for training a model to identify and/or characterize a biological structure of interest. In some such embodiments, EIS measurements may be collected in vitro and/or in vivo for a biological structure of interest (e.g., a particular type of lesion) and/or for other biological structures that may be found in an area of an animal's body adjacent to or proximate to the biological structure of interest. The EIS measurements may be for a wide range of frequencies. During training processes in accordance with FIGS. 22 and 17A, an iterative process is used in which during each iteration, a subset of frequencies are selected and EIS measurements for those frequencies are used in training the two models (a filter model and a model to identify/characterize a biological structure). Additionally or alternatively, as discussed in connection with FIG. 22, in each iteration a set of features may be selected, which may include features present in EIS measurements and/or features derived from EIS measurements. The iterative process may continue with selection, in each iteration, of frequencies and/or features and training based on the selected frequencies and/or features, until a process for identifying and/or characterizing a biological structure satisfies one or more performance targets. Such a performance target may be, as discussed in connection with FIG. 22, reaching or exceeding a desired accuracy in identifying or characterizing biological structures.

Following such a training, an insertable and/or implantable device may be configured to collect EIS measurements at the identified frequencies, and may be configured to apply the trained models to filter EIS measurements to remove measurements not corresponding to a biological structure of interest and to identify/characterize a biological structure using the filtered EIS measurements. As discussed above, those skilled in the art will appreciate that applying the trained model may include performing computations using weighting values or other values generated during the training. Accordingly, the insertable and/or implantable device may also be configured with the values determined in the training, such that the device may apply the trained model.

In some embodiments, different filters may be generated for different parts of an animal's body (e.g., a mammal's body, including a human or non-human body). For example, one filter may be generated to distinguish between heart's tissues (such as a coronary artery's wall) and a heart's lesion (such as a clot in the coronary artery), and a separate filter may be generated to distinguish between brain's tissues (such as an inner wall of a cerebral vein) and a lesion that may be found in the brain. Different models may also be trained for different biological structures of interest, such as different types of lesions. The different models may thus include a model that is trained for a particular biological structure of interest and for a particular area of an animal's body in which the biological structure of interest will be located and measured. The inventors have appreciated that having different filters for different parts of the body and/or for different biological structures of interest, rather than a single filter for the entire body may substantial limit the amount of data with which each filter is trained, thus reducing the computation involved in the learning process. Different models may also improve the accuracy of the filter. It should be noted, however, that not all embodiments need to utilize multiple filters for different parts of the body, as a single filter for a biological structure of interest may be used in some circumstances for multiple body parts or an entire body.

Figure 17B:
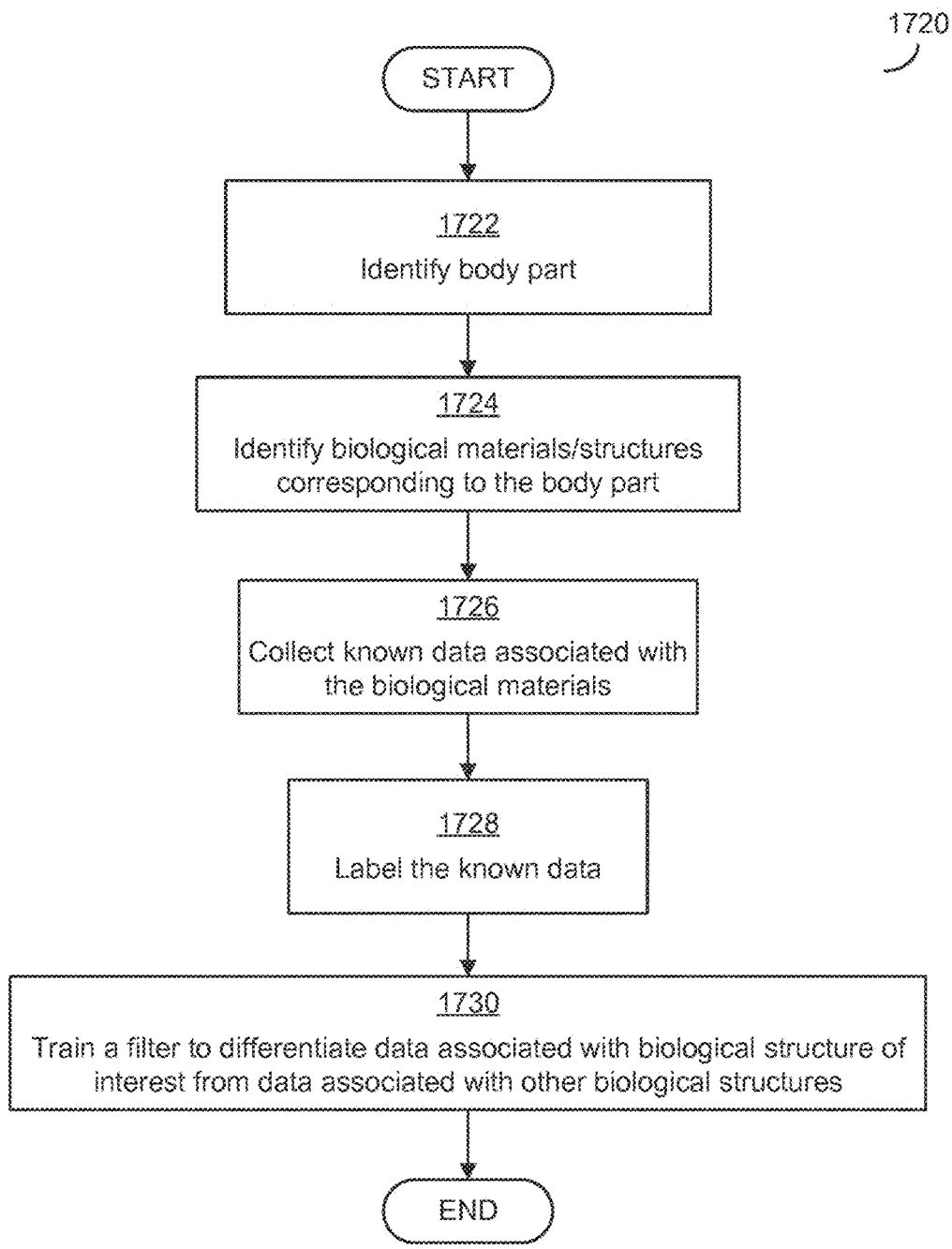
FIG. 17B is an example of a process that may be implemented in some embodiments for generating a filter using a machine learning model.

FIG. 17B illustrates a process that may be used for generating a filter for use in block 1704 of FIG. 17A. Process 1720 begins at block 1722, in which a body part is identified. Examples of body parts include, but are not limited to, a heart or a specific portion thereof, a brain or a specific portion thereof, a liver or a specific portion thereof, a kidney or a specific portion thereof, a limb's vein, etc. Once a body part has been identified, one or more biological materials (including tissues and/or lesions) of the body part may be identified at block 1724. For example, if the heart is identified at block 1722, specific tissues of the coronary artery (e.g., smooth muscle cells, elastic fibers, external elastic membrane, internal elastic member, loose connective tissues, and/or endothelial cells) and/or clots that may generally be found inside a coronary artery may be identified at block 1724.

At block 1726, data associated to the biological materials identified at block 1724 may be collected. The data may represent measurements obtaining by sampling the biological materials, which in some embodiments is performed using sensors mounted on invasive probes. In some embodiments, the data may include spectral measurements, such as collections of EIS samples obtained at different frequencies, associated to a particular biological material of the body part.

At block 1728, the collected data is labeled to refer to the specific tissue or lesion to which the data corresponds. For example, data corresponding to measurements obtained from the endothelial cells of a coronary artery may be labeled "coronary artery endothelial cells;" data corresponding to measurements obtained from the elastic fibers of a coronary artery may be labeled "coronary artery elastic fibers;" data corresponding to measurements obtained from a thrombus found in a coronary artery may be labeled "thrombus in coronary artery;" data corresponding to measurements obtained from a fibrin found in a coronary artery may be labeled "fibrin in coronary artery," etc.

At block 1730, a filter may be trained using the labeled data. Specifically, the filter may be trained to differentiate between data associated with lesions (e.g., thrombi, fibrins or other types of clots) and tissues (e.g., endothelial cells, elastic fibers, loose connective tissues, etc.).

While the techniques of FIGS. 17A-17B were described above as relating to filtering of measurements for other biological structures, it should be appreciated that the filtering techniques are not so limited. In other embodiments, the filtering techniques described in connection with FIGS. 17A-17B may be used to additionally or alternatively identify and filter out erroneous measurements. Erroneous measurements may result from any potential source of error, and may include EIS measurements with magnitude and/or phase values that are incorrect. Erroneous measurements may impact accuracy in the same or a similar manner as measurements corresponding to other biological structures. Accordingly, a training process may be carried out in which known erroneous measurements are input together with an indication that the measurements are erroneous, and along with measurements that are not erroneous, to train a model to distinguish between erroneous and non-erroneous measurements. The trained model (which may additionally be trained to distinguish between measurements for a biological structure of interest and measurements for other biological structures) may then be used by a device to filter measurements.

The inventors have appreciated that conventional techniques for identifying the location of an insertable device relative to a lesion in an animal's body are often unsatisfactory. One conventional technique for locating clots inside vasculature, for example, involves the use of x-ray images in connection with x-ray reflective probes. Specifically, when an invasive probe having a portion that is reflective to x-rays is inserted in a duct of an animal, the position of the probe can be monitored using x-ray imaging. Unfortunately, clots are typically not reflective to x-rays; therefore, the x-ray image provides no indication as to the location of the clot. As a result, the process of contacting the clot with the invasive probe with is often onerous, and it inevitably involves numerous attempts. This process may undesirably increase the duration of an operation, or even worse, may lead to damage to the duct's inner walls as the clinician repeatedly steers the probe in search of the clot.

The inventors have therefor recognized the advantages of a technique for determining whether a probe is in contact with a lesion. Accordingly, some embodiments are directed to techniques for identifying whether a biological structure being probed is a biological structure of interest like a lesion (e.g., a clot) or another biological structure like a tissue on which the lesion is formed (e.g., the inner wall of a duct). In some embodiments, machine learning techniques may be used to identify whether a biological structure is or is not a biological structure of interest. Accordingly, a model may be trained using known data identifying measurements associated with different biological structures. Once trained, the model may be able to differentiate between biological structures. In some embodiments, the process of FIG. 17B is used to train the model, though alternative processes are also possible.

Figure 17C:
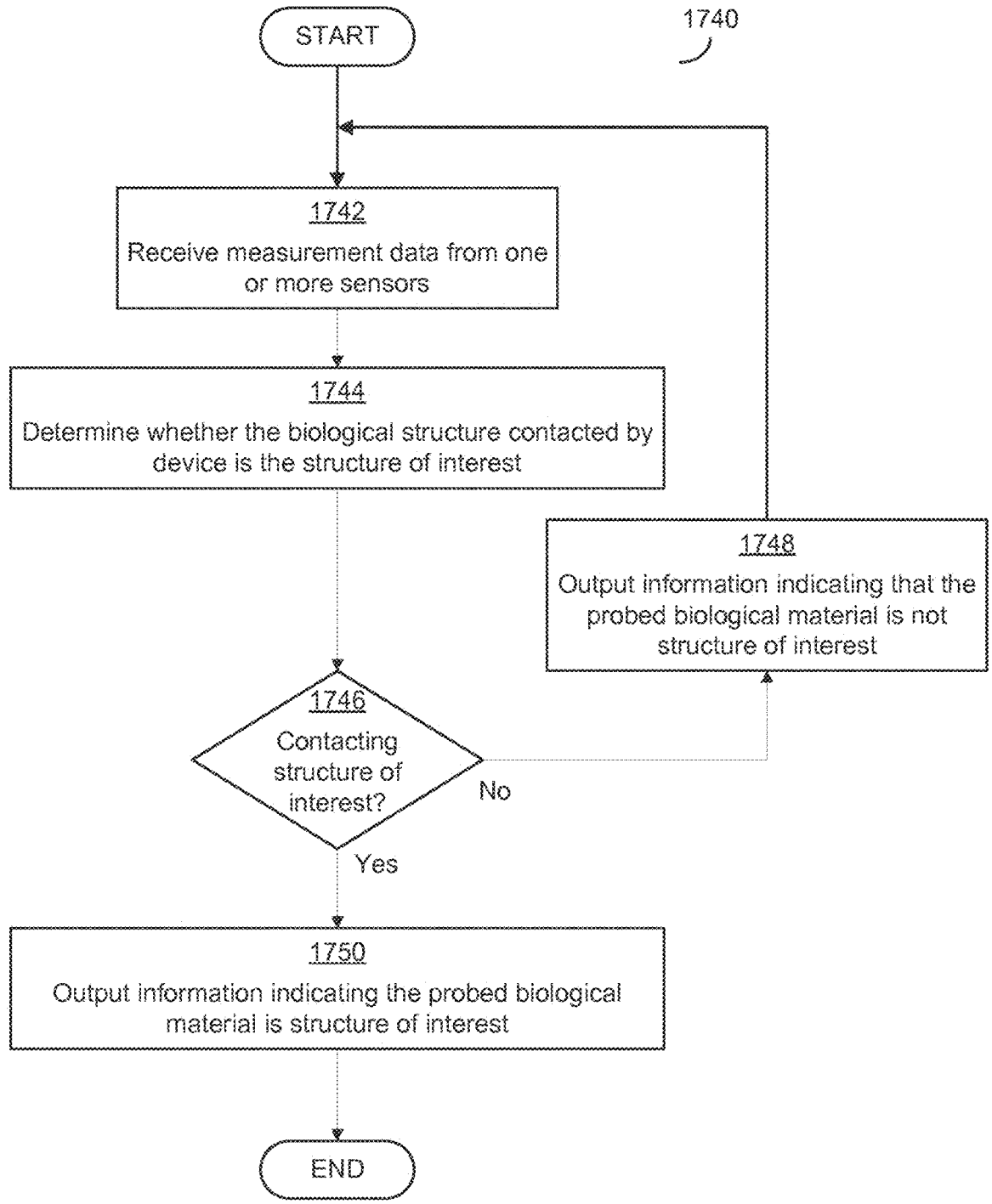
FIG. 17C is an example of a process that may be used in some embodiments to aid a clinician in guiding an invasive probe.

FIG. 17C illustrates a process that may be used to aid a clinician in guiding an invasive probe. Process 1740 begins at block 1742, in which data is received, for example at a processor of a medical device, from one or more sensors mounted on an invasive probe that is inserted into an animal (e.g., in the animal's vasculature). The received data may include, at least in some embodiments, measurements of impedance associated with one or more biological structures of the animal.

In some embodiments, the data received in block 1742 may be multiple sets of sensor readings, collected over an interval of time. During that interval of time, the insertable or implantable device may, in some cases, not be moved, such that all sensors of the device are contacting the same materials throughout those sets of measurements. The multiple measurements in such cases may assist in generating a high-confidence result in identifying or characterizing a biological structure contacted by the sensors of the device. In some embodiments, for example, a trained model for identifying or characterizing a biological structure may produce a value indicative of a confidence of the model that sensor readings correspond to a particular biological structure or particular characteristics (e.g., composition) of the biological structure. The model may accept additional data as input, which may adjust the confidence higher or lower. Collecting multiple data over an interval of time may therefore aid in producing a high-confidence result that a biological structure is or is not a biological structure of interest. In some such embodiments, for example, the biological structure(s) contacted by a device may be sampled such the at least three spectra are obtained in less than three seconds, at least five spectra are obtained in less than three seconds, or at least ten spectra are obtained in less than three seconds.

At block 1744, it may be determined whether the measurements correspond to a biological structure of interest, such as a particular type of lesion. In some embodiments, this determination may be performed in part using a machine learning filter trained according to process 1720 (FIG. 17B), which may be trained to distinguish between biological structures.

If it is determined that EIS measurements correspond to another biological structure that is not the structure of interest, then in block 1746 information may be output to a user, informing the user that the probe is not yet contacting the biological structure of interest. The information may be output in any suitable way, for example using a display or an acoustic device. Based on this information, the clinician may decide to continue to guide the invasive probe inside the animal, and process 1740 may repeat through blocks 1742, 1744 and 1746.

In some embodiments, the determination steps of blocks 1744 may relate to whether all EIS measurements collected by a device at a particular time or over a particular time interval correspond to a biological structure of interest. For example, the determination may be whether the device is fully contacting the structure of interest (e.g., lesion) or whether one or more of the sensors is contacting another biological material. If not all of the sensors are determined to be contacting the structure of interest, then in block 1746 information may be output indicating that the device is not fully contacting the biological structure of interest (e.g., the lesion). In other embodiments, the determination step of block 1744 may be performed to identify which (if any) sensors of the device are producing readings indicating that the sensors are contacting the biological structure of interest. Distinguishing between sensors in this manner may assist a clinician in guiding a device to properly and fully contact a biological structure of interest. For example, if sensors are arranged longitudinally along the length of an insertable device, then as the device approaches and then contacts a biological structure of interest, the sensors may over time produce values indicative of not contacting the desired structure, then the sensors at a distal end may produce values indicating that they are contacting the structure, then all sensors may produce values indicating that they are contacting the structure once the device is properly sited. If the clinician moves the device too far, the distal sensors may produce values indicating that they are not contacting the desired structure.

If it is determined that the probed biological material is a biological structure of interest, then in block 1750 information to that effect may be output. Subsequently, the clinician may perform any of the following steps: operate the invasive probe to determine one or more characteristics of the lesion (as described in connection with block 104 of FIG. 1); operate a medical device to generate and output treatment recommendation based on the lesion characteristics (as described in connection with block 106 of FIG. 1); select a treatment option based on the treatment recommendation (as described in connection with block 108 of FIG. 1); and/or treat the lesion using the selected treatment option (as described in connection with block 110 of FIG. 1).

EXAMPLES

Described below are various examples of scenarios in which medical devices and techniques may be used. It should be appreciated, however, that embodiments are not limited to operating in accordance with any one of these examples.

Example 1

One example of a way in which the techniques described herein may be used is with an invasive, smart guide wire. The invasive guide wire may be used in navigating the vascular system. Using sensors and analysis techniques described herein, the invasive guide wire may characterize tissue/materials with which it is in contact and communicate characteristics of this tissue/material to a clinician. The invasive guide wire may also help additional devices reach an intervention site within a patient.

In this example, the guide wire comprises a sensor (preferably an EIS sensor), an impedance spectrometer, and a handle. The guide wire may also include additional components that can be inserted along its length during use. The sensor may be used to sense and characterize properties of the tissue/material with which it is in contact. For example, the sensor may be used to determine tissue/material composition when used with the impedance spectrometer to perform high frequency impedance measurements. Both the sensor and the impedance spectrometer are preferentially located at an invasive tip of the guide wire so that tissue adjacent to the tip can be characterized without the need for long electric wires connecting sensor to the impedance spectrometer. This design may reduce electronic noise that may be otherwise inserted into electrical signals if the impedance spectrometer were located outside the subject.

The handle may contain additional components, such as those for communicating with the user, recording and transmitting data both during and after surgery, processing data, and powering the device. Examples of such components include a feedback unit such as a display or indicator light readable by a user, a unit for transmitting data either wirelessly or through a cable, a database, a processor, and a battery. The handle can be removable from the other device components; it can also be removably connected to circuitry on the guide wire itself.

Example 2

The guide wire described in Example 1 may be used by a clinician to determine an optimal treatment strategy for a patient experiencing a blocked artery. The clinician can use the guide wire to characterize the tissue/material that is blocking the artery and then choose between different possible treatments based on this information. In some embodiments, the guide wire may provide treatment recommendations to the clinician based upon one or more characterizations that it has performed and, optionally, based upon data from prior treatments performed with the aid of a guide wire.

In this example, the clinician can use the guide wire to assess and treat an arterial lesion. The clinician can begin by steering the guide wire to the site of the thrombus, optionally using the handle, and then penetrating the thrombus. Next, the clinician may use the guide wire to perform a measurement of the composition of the thrombus and/or of the tissue/material that is blocking the artery. The clinician can then determine an optimal treatment for the blocked artery based upon the results of this measurement. For example, the clinician may decide to use a stenting device if the blocking tissue is composed of cells from the arterial wall of the patient. If the blocking tissue is a thrombus, the clinician can instead decide to measure its viscoelastic properties and then determine whether to use an aspiration catheter or a stent to remove the clot on the basis of this information.

In some embodiments, the clinician may also receive a treatment recommendation from the guide wire. The treatment recommendation can be based upon the characterizations performed by the guide wire on the arterial lesion and/or based upon data collected during previous uses of a guide wire.

Upon conclusion of treatment, the clinician may remove the handle from the guide wire and insert the appropriate interventional device with the aid of the guide wire.

Example 3

An additional example of a device which may be used in accordance with the techniques described herein is a smart stent-retriever. The stent-retriever may be used to retrieve blood clots from a patient. Using sensors and analysis techniques described herein, the invasive stent-retriever may characterize a clot with which it is in contact and communicate characteristics of this tissue/material to a clinician.

In this example, the stent-retriever comprises at least one sensor (preferably at least one EIS sensor and/or EIT sensor), a measurement unit, and a handle. The stent-retriever may comprise multiple sensors at multiple strategic locations so that information regarding a blood clot with which it is in contact can be obtained from multiple locations within the clot. When a stent-retriever includes more than one sensor, the sensors may be able to sense different properties of the clot with which it is in contact. For example, the stent-retriever may comprise one or more sensors capable of sensing the integration of the clot with the stent-retriever, one or more sensors capable of sensing the position of the stent-retriever as a function of time, and/or one or more sensors capable of sensing the force applied to the clot. The integration of the stent-retriever with the clot may be determined by sensing the inductance and/or EIT signal of a stent as a function of time. Because the inductance and EIT values of the stent will vary with the expansion of the stent and the surrounding environment, constant values of these properties indicate that the stent has reached its maximal expansion and integration into the clot. A motion sensor may be used to sense the position of the stent-retriever as a function of time. This feature can enable the clinician to understand the movement of the stent-retriever within the patient and to determine the number of passes the stent-retriever has made during retrieval of a clot. Stress sensors may also be included to measure the force applied by the stent-retriever to a clot or tissue/material.

The measurement unit of the stent-retriever may be an impedance spectrometer and/or a tomography unit. This unit is preferentially located close to the tip of the stent-retriever so that a clot adjacent to the stent-retriever can be characterized without the need for long electric wires connecting sensor to the measurement unit. This design may reduce electronic noise that may be otherwise inserted into electrical signals if the impedance spectrometer were located outside the subject.

The handle may contain additional components as described in Example 1. It can also comprise a robotized pulling mechanism to allow accurate and automatized retrieval of the clot.

Example 4

The guide wire described in Example 1 and the stent-retriever described in Example 3 may be used together by a clinician to determine and execute an optimal treatment strategy for a patient experiencing a blocked artery. The clinician can use the guide wire to characterize the tissue/material that is blocking the artery and then use the stent-retriever to retrieve the clot and/or thrombus. Optionally, data can be collected during clot retrieval and uploaded to a database for later analysis.

In this example, a clinician can use a combination of smart devices to treat a patient experiencing a blocked artery. The clinician may begin by inserting the guide wire with a sheath and using the guide wire (with an invasive probe, as discussed above) to assess the lesion as described in Example 2. If the clinician decides to next use a stent-retriever based upon information and/or a recommendation provided by the guide wire, the clinician will remove the guide wire, leaving the sheath in place, and insert the stent-retriever along the sheath and steer it into the clot and/or thrombus. Once the stent penetrates the clot and/or thrombus, the sensors incorporated into the stent-retriever can sense aspects of the clot and/or thrombus and provide this information to the clinician as a function of time (e.g., on an external display). For example, the EIS and/or EIT sensors can characterize the integration of the stent with the clot and/or thrombus and the shape and composition of the clot and/or thrombus. The stent-retriever may also use data from prior clot and/or thrombus retrievals to provide treatment recommendations to the clinician. Treatment recommendations can include, for example, signals that integration of the stent-retriever with the clot and/or thrombus is optimal and/or recommendations regarding the appropriate speed and force with which to pull the clot and/or thrombus.

At this point, the clinician may act upon the information and/or recommendations provided by the stent-retrieve to retrieve the clot and/or thrombus. The clinician may decide to use an automatic pulling mechanism incorporated in the stent-retriever to retrieve the clot. The automatic pulling mechanism may then pull the clot and/or thrombus at a speed and using a force determined by the stent-retriever based upon data received from a database of prior clot and/or thrombus retrievals. If the clot and/or thrombus detaches form the stent retriever, the stent-retriever will signal the clinician using an alarm. The clinician may then penetrate the clot and/or thrombus once again and restart the retrieval process.

At the conclusion of the clot and/or thrombus retrieval, all the data collected during the intervention can be transferred to a database for later analysis.

Example 5

Another example of a device which may be used in accordance with the techniques described herein is a smart aspiration-catheter. The aspiration-catheter may be used to retrieve blood clots from a patient. Using sensors and analysis techniques described herein, the invasive aspiration-catheter may characterize a clot with which it is in contact and communicate characteristics of this tissue/material to a clinician.

In this example, the aspiration-catheter comprises at least one sensor (preferably at least one EIS sensor and/or EIT sensor), a measurement unit, and a handle. As in Example 3, the aspiration-catheter may comprise multiple sensors at multiple strategic locations so that information regarding a blood clot with which it is in contact can be obtained from multiple locations within the clot. When an aspiration-catheter includes more than one sensor, the sensors may be able to sense different properties of the clot with which it is in contact. For example, the aspiration-catheter may comprise one or more of the sensors described in Example 3 (i.e. one or more sensors capable of sensing the integration of the clot with the aspiration-catheter, one or more sensors capable of sensing the position of the aspiration-catheter as a function of time, and/or one or more sensors capable of sensing the force applied to the clot). The aspiration-catheter may also comprise an additional sensor capable of monitoring blood flow within the aspiration-catheter.

The measurement and the handle unit of the aspiration-catheter are identical to the measurement unit and handle of the stent-retriever described in Example 3.

Example 6

The guide wire described in Example 1 and the aspiration-catheter described in Example 5 may be used together by a clinician to determine and execute an optimal treatment strategy for a patient experiencing a blocked artery. The clinician can use the guide wire to characterize the tissue/material that is blocking the artery and then use the aspiration-catheter to retrieve the clot and/or thrombus. Optionally, data can be collected during clot retrieval and uploaded to a database for later analysis.

In this example, a clinician can use a combination of smart devices to treat a patient experiencing a blocked artery. The clinician may begin by inserting the guide wire and using it to assess the lesion as described in Example 2. If the clinician decides to next use an aspiration-catheter based upon information and/or a recommendation provided by the guide wire, the clinician will then insert the aspiration-catheter along the guide wire, steer it into the clot and/or thrombus, and begin the aspiration process. During aspiration of the clot and/or thrombus, an external display will provide information to the clinician regarding removal progress, the shape and composition of the clot and/or thrombus as sensed by the EIS and/or EIT sensors, and the passage of the clot and/or thrombus through the aspiration-catheter. The smart aspiration-catheter may determine also determine the optimal time to begin removal of the clot and/or thrombus based upon integration of the aspiration-catheter with the clot and signal this condition to the clinician. The clinician may then begin to remove the clot and/or thrombus. If the clot and/or thrombus detaches from the aspiration-catheter, the aspiration-catheter may signal the clinician using an alarm. The clinician may then penetrate the clot and/or thrombus once again and restart the retrieval process. When the sensors detect that the thrombus has been fully aspirated and passed along the tube of the aspirator, another message indicating successful removal may be generated and output.

At the conclusion of the clot and/or thrombus retrieval, all the data collected during the intervention can be transferred to a database for later analysis.

Example 7

The guide wire described in Example 1 may be used to treat a patient experiencing Chronic Total Occlusion (CTO). In this case, the patient's artery is blocked by an old and rigid thrombus that may be difficult for the clinician to penetrate in order to reestablish blood flow. The clinician may use the smart-guide wire to sense the position of the lesion and pass through the lesion. During operation, the guide wire can provide information to the clinician regarding when penetration of the lesion is initiated and when passage through the lesion to the lumen of the artery occurs. If the thrombus is too rigid to penetrate, the clinician can instead pass the guide wire through the arterial wall adjacent to the lesion. In this case, the guide wire can provide continuous information to the clinician regarding its position within the atheroma/plaque. This may help the clinician to avoid puncturing the vessel.

Example 8

The guide wire described in Example 1 may be used by a clinician in diagnosis and/or treatment of peripheral pathologies. Examples of peripheral pathologies include thrombi formed in deep veins or arteries, or thrombi formed in artificial veins or arteries. The guide wire may be used to determine an optimal treatment strategy for a patient experiencing a peripheral pathologies. The clinician can use the guide wire to characterize the tissue/material that is blocking the duct and then choose between different possible treatments based on this information. In some embodiments, the guide wire may provide treatment recommendations to the clinician based upon one or more characterizations that it has performed and, optionally, based upon data from prior treatments performed with the aid of a guide wire.

Example 9

As an additional example, any one of the foregoing invasive probes may be used to estimate the age of a clot (e.g., a thrombus). The age of the clot (i.e., the life of the clot since its formation) may be determined on the basis of one or more characteristics of the clot, such as the composition of the clot. Different treatments or combination of treatments may be provided based on the age of the clot, as determined from these characteristics. For example, one treatment may be recommended if the clot is less than fourteen days and a different treatment may be recommended if the clot is more than fourteen days.

Additionally, or alternatively, at least some of the devices and techniques described herein may be used to identify whether a biological structure is a healthy tissue. For example, the devices/techniques may be used to determine whether a wall of a vessel is healthy or whether an atheromatous plaque or a calcification has formed on the vessel wall. In such a case, a biological structure that is contacted by one of the devices described herein may be a vessel wall or an atheromatous plaque (or other lesion), and the techniques described herein may be used to determine whether it is one of those biological structures. Based on the identification, different treatment recommendations may be provided.

Methods of Operating a Medical Device for use in Oncology

The inventors have recognized and appreciated that conventional techniques for examination of potentially cancerous cells are often unsatisfactory. For example, one conventional technique for examining potentially cancerous cells uses a needle to remove a tissue sample. To aid a clinician in guiding the insertion of the needle, conventional imaging systems such as x-ray, ultrasound, or magnetic resonant imaging (MRI) are used. However, images generated using these techniques are often inaccurate or blurred, thus making it difficult for the clinician to determine whether the needle is in contact with the cell or tissue being targeted. As a result, diagnosis and/or treatment of cancerous cells using such techniques is often inaccurate. As a result, when trying to determine whether a particular lesion is cancerous, a significant risk is that a needle intended to examine the potentially-cancerous lesion does not actually contact the lesion but instead contacts nearby healthy tissue, leading to an incorrect sample and incorrect medical conclusion. Similarly, when attempting to remove cancerous cells, two undesirable situations may arise: healthy tissues may be removed together with the cancerous cells, or some cancerous cells may be left unremoved.

Accordingly, in accordance with some embodiments described herein, a medical device may be used to determine the presence of a cancerous cell/tissue, the characteristics of a cancerous cell/tissue, and/or or the type of cancerous cell/tissue (e.g., carcinomas, lymphomas, myelomas, neoplasms, melanomas, metastases or sarcomas). For example, the machine learning techniques described above may be used to differentiate between cancerous cell/tissues and non-cancerous biological materials and/or to characterize cancerous cell/tissues. Furthermore, techniques of the type described herein (including machine learning techniques) may provide recommendations on how to treat a cancerous cell/tissue based, at least in part, on the characteristics of the cancerous cell/tissue. For example, ablation or removal of a cancerous cell/tissue may be recommended in some circumstances, as well as a manner in which to ablate or remove.

Figure 32:
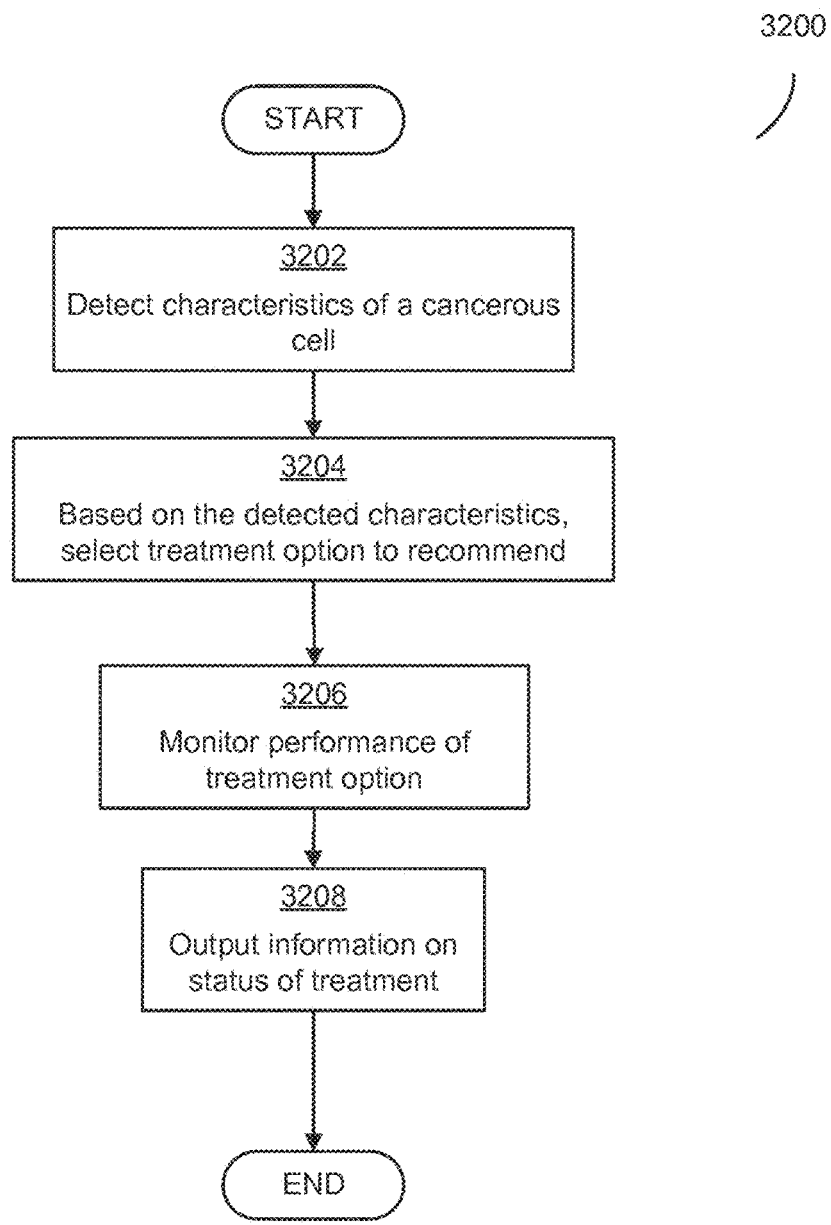
Figure 33:
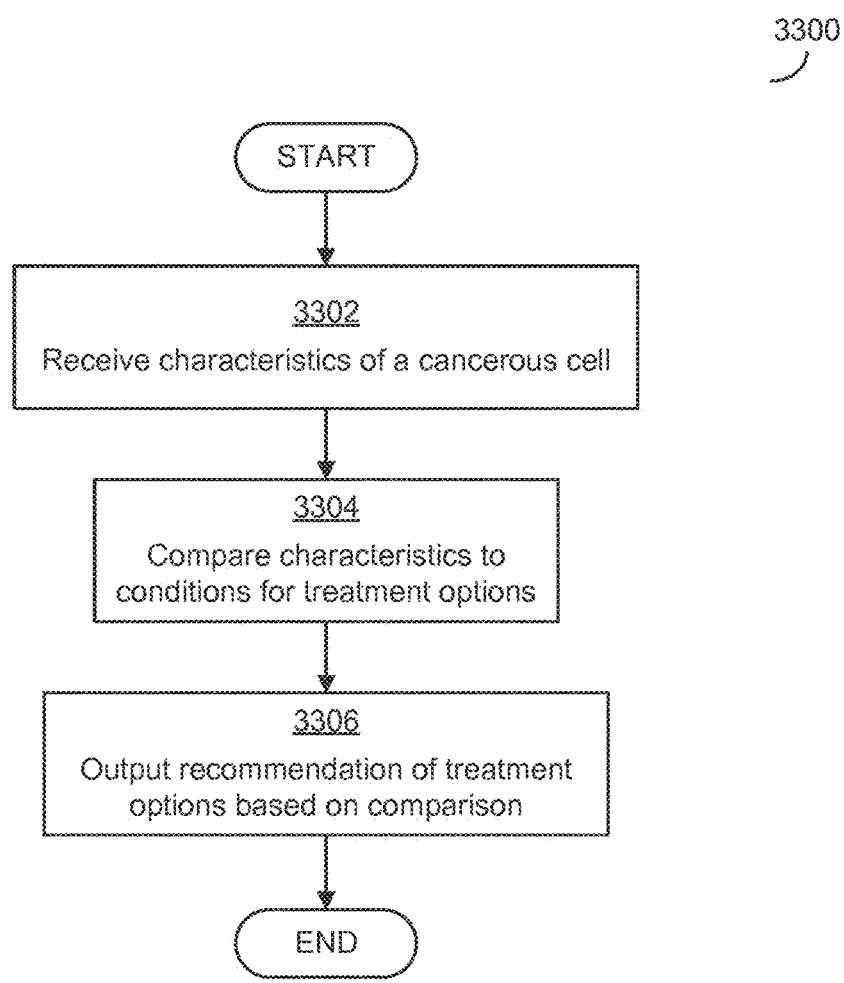

Examples of medical devices, sensors, and manners of sensing tissues/materials of a cancerous cell are described in detail above with respect to FIGS. 2-11. Described below in connection with FIGS. 31-33 are examples of techniques that may be implemented by such a medical device and/or that a medical device may be operated to perform.

Figure 31:
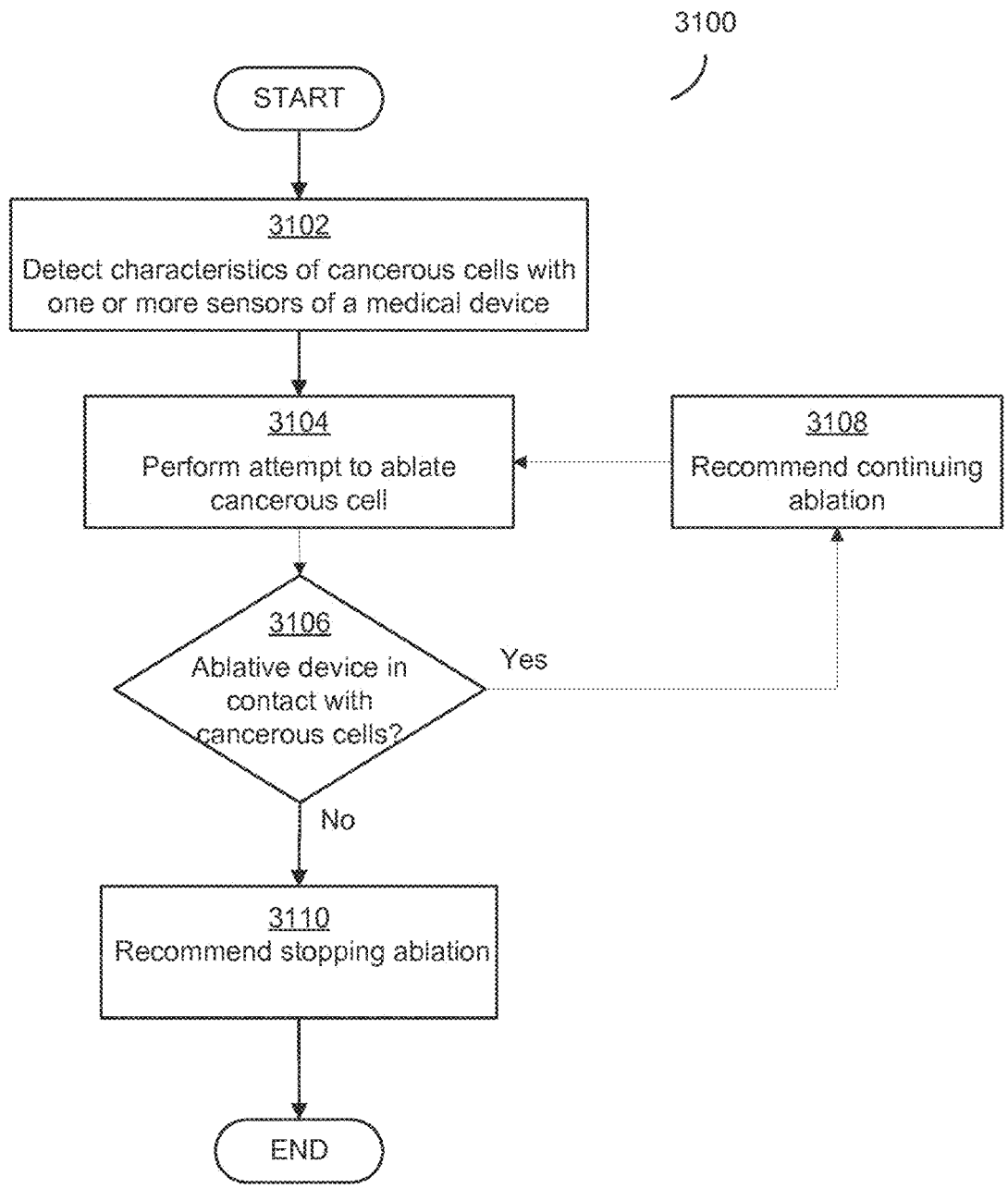
FIG. 31-33 are flowcharts of illustrative methods of some embodiments for operation of medical devices in accordance with embodiments described herein to generate treatment recommendations based in part on the characteristics of cancerous and/or noncancerous tissue.

FIG. 31 illustrates, an exemplary process 3100 that may be performed by a medical device operating in accordance with some techniques described herein. In the example of FIG. 31, the sensor may be disposed in diagnosis and/or treatment devices, such as in needles, ablation catheters, radiofrequency probes, robotic probes, laparoscopes, or cutting devices. In some embodiments, the sensor is disposed near the distal end of the medical device. The medical device may generate treatment recommendations based on characteristic(s) of the cancerous cell determined using the sensor. It should be appreciated that the processes described herein are not limited to use with invasive probes. In some embodiments, techniques described herein may be used with systems and devices that include non-invasive probes that may not be designed for use or solely for use within a body of an animal but may be additionally or alternatively designed for use on biological structures, including tissues, on an exterior of an animal's body. For example, in some embodiments, devices, systems, and techniques described herein may be used for diagnosis and/or treatment of superficial lesions, such as skin cancer or other skin conditions.

The process 3100 begins in block 3102, in which an invasive probe of a medical device is operated to detect one or more characteristics (e.g., size and/or composition) of a lesion that is proximate to the sensor, which may be a cancerous tissue or cell. Prior to the start of the process 3100, the invasive probe may be inserted into the body of an animal and moved proximate to a predicted location of the lesion. The medical device then is operated to detect when the sensor contacts the lesion. Contact of the lesion, or of the tissue that is known to be or is potentially cancerous, may be determined by evaluating a change over time in a value output by the sensor (e.g., a change in impedance), or using machine learning techniques as described in connection with FIG. 17C. For example, the medical device may output (e.g., to a user, via a user interface) one result when the sensors of the invasive probe are not contacting a cancerous tissue/cell, or is not contacting the type of tissue of which the lesion is known to be a part.

For example, when the lesion to be investigated, as the invasive probe is moved through the animal toward the lesion, the medical device may output a value that is indicative of a tissue that it is contacting. The value may in some embodiments be a qualitative value, including a binary value such as a yes/no or true/false value to indicative whether the invasive probe is contacting the lesion.

The medical device may determine whether the invasive probe is contacting the lesion by analyzing the biological material(s) contacted by the invasive probe, including the tissues contacted by the invasive probe, to determine whether the invasive probe is contacting any biological materials that are "abnormal" and thus may be a part of a lesion. The medical device may, in some embodiments, determine whether a biological material contacted by the probe is "abnormal" by evaluating a location of the invasive probe within the animal, which may indicate biological materials that the invasive probe may be expected to contact.

The medical device may additionally or alternatively determine whether the invasive probe is contacting the lesion based on predictions about the lesion, which may be input by a clinician as a result of a preliminary diagnosis. For example, the clinician may input information preliminarily characterizing a lesion, such as whether the lesion is in vasculature or is a lesion of an organ, or in the case of a lesion of an organ what the organ is, a prediction of a composition of the lesion, or a prediction of a state of tissues or cells of the lesion (e.g., unhealthy, inflamed, cancerous, diseased, etc.). In embodiments in which such information is input, the clinician may input the information preliminarily characterizing the lesion individually, or may make a selection of a preliminary diagnosis of the lesion that may be associated with such information preliminarily characterizing the lesion (e.g., by selecting a particular category of atheroma, other information such as an expected composition of the atheroma and that it is located in vasculature may also be selected). As the invasive probe moves through the animal, the medical device may compare biological materials contacted by the invasive probe to the preliminary characterization of the lesion to determine whether the invasive probe is contacting the lesion. For example, if the lesion has been preliminarily diagnosed as a brain lesion that may be a brain tumor, the medical device may determine whether the invasive probe has contacted abnormal brain tissue and/or whether the invasive probe has contacted cancerous brain tissue, and output this result.

In other embodiments, rather than merely providing a binary value indicating whether the invasive probe is contacting the lesion, the medical device may output a value indicative of, for example, an identity, quantity and/or relative abundance of a biological material or biological materials being contacted by sensors of the invasive probe, which may vary as the probe moves through the body. The value indicative of the material(s) may be an identification of the materials, such as a list of materials identified from impedance spectra, as determined using techniques described herein (including the machine learning techniques described above). The values may, in other embodiments, be numeric values, such as values detected by sensors (e.g., an impedance value, or impedance spectrum) or other values.

The probe and its sensor may be moved until contacting a lesion, at which point a result output by the medical device may change once contact is made. In this manner, a location of a lesion may be determined using the invasive probe, and a determination may be made that the invasive probe is contacting the lesion.

The invasive probe may additionally, in some cases, be operated to determine the geometry of a lesion. For example, the geometry of a lesion potentially including cancerous tissue (e.g., a tumor) may be determined in some embodiments by moving the invasive probe in the proximity of the lesion and identifying when sensors of the invasive probe are or are not contacting the lesion. For example, if an analysis of values output by the invasive probe determines that the lesion includes cancerous tissue, the invasive probe may be moved and a determination made, over time, and for different sensors, of whether individual sensors are contacting cancerous tissue. The amount of movement of the invasive probe (e.g., measured using an accelerometer, as discussed above) and position of the sensors on the invasive probe may then be analyzed by the medical device to determine a geometry of the cancerous tissue within the animal, including one or more dimensions of the cancerous tissue.

In some such embodiments, the medical device may determine one or more treatment recommendations for a lesion based on the geometry of the lesion.

In one treatment protocol that may be implemented in embodiments such as the one illustrated in FIG. 31, ablation may be used as a first option for treatment of a cancerous tissue. Accordingly, in block 3104, an ablative device such as a needle or a radiofrequency probe is inserted into the animal. In some embodiments, the ablative device may include an invasive probe including sensors of the type described herein. The ablative device may be moved until the ablative device determines that contact with a cancerous cell or tissue has been formed. (Though, it should be appreciated that embodiments are not limited to operating with an ablative device that includes an invasive probe. In other embodiments, the invasive probe is part of a separate medical device, and after positioning of the invasive probe the ablative device is moved until located proximate to the invasive probe and thus located proximate to the cancerous cell/tissue.)

In block 3104, following placement of the ablative device proximate to the cancerous cell/tissues, the ablative device is operated to ablate the cancerous cell/tissue. Following a treatment time interval, the ablative device may be operated to determine whether the ablative device is having an effect on the cancerous cell/tissue. For example, in some embodiments, a treatment recommendation may be generated that guides a clinician in performing the ablation, including whether the ablation is effective and whether to continue with the ablation. Accordingly, in block 3106, the sensor may provide information indicating whether the ablative device is still in contact with cancerous cells or cancerous tissue. This determination may be made using techniques described herein (including the machine learning techniques described above). The information may be processed and may be used to provide a treatment recommendation, such as whether to stop the ablation or continue the ablation, or to check the positioning of the invasive probe before determining whether to stop ablating.

In some embodiments, the ablative device may include multiple different electrodes with which to ablate, such as different electrodes positioned at different locations, and the different electrodes may be individually operable, such that some may be operated to ablate at a time that others are not being operated to ablate. In some embodiments, each ablation electrode may be disposed near sensing electrodes, with the sensing electrodes being operated in accordance with techniques described herein to determine a biological material contacted by the sensing electrode. The ablative device may determine, using the sensing electrodes, whether a particular part of the ablative device is contacting cancerous tissue/cell or noncancerous tissue/cell. In some such embodiments, in response to determining that a part of the ablative device is contacting noncancerous tissue, the ablative device may cease or prevent operation of the ablative electrodes of that part of the ablative device, to limit ablation to only the cancerous tissues and minimize damage that may be done to noncancerous tissues.

In this way, the clinician may stop ablating if this treatment is ineffective, and the clinician may only continue ablating while the ablative device is in contact with the cancerous cell/tissue and thereby only ablate cancerous tissues. The clinician may thus be more confident at the end of the treatment of whether the treatment was successful and, if it was successful, that all of the cancerous cell/tissue has been ablated. In this way, the risk of ablating healthy tissues, and/or the risk of leaving cancerous cells un-ablated, is mitigated.

Accordingly, as illustrated in FIG. 31, if it is determined that the ablative device is still in contact with the cancerous cell/tissue, process 3100 proceeds to block 3108, in which a recommendation to continue to ablate is provided, and iterates to block 3104. Otherwise, if it is determined that the ablative probe is no longer in contact with the cancerous cell/tissue, a recommendation to stop the ablation is provided in block 3110. The process may be repeated by repositioning the ablative device. If contact can no longer be formed with a lesion even after several attempts to reposition the ablative device, process 3100 ends.

FIG. 32 illustrates an example of a manner of operating a medical device to generate treatment recommendations for a cancerous cell/tissue in accordance with another embodiment. In the embodiment of FIG. 32, a medical device may include multiple sensors arrayed along an exterior of a probe, such as in the example of FIG. 3 discussed above. As should be appreciated from the foregoing, with such an array of sensors, several different characteristics of a cancerous lesion may be determined, including composition of the cancerous lesion. For example, by performing an EIS process on the cancerous lesion, a composition of the cancerous lesion may be determined, as discussed above. In some embodiments, trained machine learning models as described above may be used to determine the composition or other characteristics of the cancerous lesion.

The process 3200 of FIG. 32 begins in block 3202, in which a medical device is inserted into the body of an animal subject and operated to detect one of more characteristics of a cancerous lesion, for example a composition of a cancerous lesion. Based on the characteristics, including the composition, the medical device may in block 3204 select a treatment option to recommend. Based on the composition, process 3200 may determine the type of cancerous lesion being probed, and an appropriate treatment recommendation may be provided. The medical device may be configured, such as in other embodiments described above, with information on impedance spectra and other electrical characteristics (e.g., effective capacitance) for different biological materials and on compositions of different lesions, such that biological materials may be identified using impedance spectra and lesions may be identified based on biological materials. The medical device may be further configured with different treatment recommendations for different types of lesions, such as different types of cancerous lesions. In one example, if it is determined using impedance spectra for different biological materials of the lesion that the cancerous lesion is or is a part of a carcinoma, a recommendation to remove the cancerous lesion may be provided. In another example, if is it determined that the cancerous lesion is part of a melanoma, radiofrequency ablation may be recommended. The medical device may select the treatment option in any suitable manner.

Once a treatment is recommended in block 3204, the medical device may in block 3206 monitor performance of the selected treatment option. The medical device may monitor the treatment using one or more sensors, such as the one or more sensors with which the characteristics were determined in block 3202 or one or more sensors of a treatment device that is operated to perform the treatment. For example, if ablation is recommended in block 3204, a clinician may insert an ablative device. The ablative device may have a sensor, such as a temperature sensor, for sensing the state of the cancerous lesion as ablation is being performed. The sensor may detect whether the ablation was successful by determining whether the cancerous lesion is burned or frozen.

In block 3208, information on a status of a treatment is output by the medical device via a user interface, for presentation to a clinician. Then, the process 3200 ends.

While an example of monitoring a treatment is given in the context of generating treatment recommendations, it should be appreciated that similar techniques may be used to raise error messages or other messages to a clinician regarding a status of a treatment. For example, if a sensor on a treatment device indicated presence of the cancerous lesion for a time, after which the sensor no longer detects the cancerous lesion, the medical device may determine that the treatment device is improperly positioned or that the cancerous lesion was lost. This may indicate either that the device needs to be repositioned or that the cancerous lesion has moved. A message to the clinician via the user interface may indicate such a potential problem.

Additionally, while the example of FIG. 32 described a manner of operating a medical device to provide treatment recommendations both relating to an initial selection of a treatment and related to a subsequent manner of performing that treatment, it should be appreciated from the foregoing that embodiments are not so limited. For example, in some embodiments, a medical device may include one or more sensors as described herein and may be operated to produce treatment recommendations on a manner of operation of that device, without generating an initial recommendation to use that device. For example, a needle or a radiofrequency probe, as discussed above, may include one or more sensors to generate data on a status or performance of a treatment and may produce treatment recommendations.

FIG. 33 illustrates a process 3300 that may be implemented by a medical device in some embodiments for generating treatment recommendations.

The process 3300 begins in block 3302, in which the medical device is operated to determine one or more characteristics (e.g., size and/or composition) of a cancerous lesion, using techniques described herein. The medical device may receive the characteristic(s) from a component of the medical device. For example, one or more sensors included in the medical device and/or another component that generates characteristic(s) based on data produced by the sensors. The characteristic(s) may include a composition of the cancerous lesion, in some embodiments. The characteristic(s) may additionally or alternatively include a location of the cancerous lesion within the body, one or more dimensions of an aggregate of cancerous lesion (e.g., a length, a thickness, etc.), a temperature of the cancerous lesion, or other information that may be determined based on the types of sensors described above.

In block 3304, the medical device compares the characteristic(s) received in block 3302 to one or more conditions for one or more treatment options. The medical device may be configured with information on multiple different available treatment options, each of which may be associated with one or more conditions that relate to one or more characteristics of a cancerous lesion. The treatment options may include ablation, removal and biopsy. Examples of such conditions related to a composition of a cancerous lesion are described above in connection with FIG. 32. Trained machine learning models, for example as described in connection with FIG. 15B, may be used to determine relationships between cancerous lesion characteristics and options for successful treatments.

The medical device may compare the characteristic(s) of the cancerous lesion to the conditions for one or more treatment options to determine which conditions are met. In some embodiments, the sets of conditions for treatment options may be mutually exclusive, such that a cancerous lesion may meet only one set of conditions and thus only one treatment option may be selected. In other embodiments, the set of conditions may not be mutually exclusive, and the medical device may determine which treatment option to recommend by identifying the one for which the most corresponding conditions are met or the one for which the corresponding conditions are met most closely. For example, in the case that different conditions are associated with different ranges of values, such as ranges of impedance spectra, a condition may be determined by identifying a range for which a value for a lesion most closely matches. The closest match may be the range, for example, that the lesion's impedance spectrum or other value falls within or is the farthest from a boundary value for the range, or has the most overlap with the range.

In block 3306, based on the comparison, the medical device may output a recommendation of a treatment option via a user interface of the medical device, and the process 3300 ends.

Those skilled in the art will appreciate that there are a number of ways in which to set the conditions for treatment options that may be used in connection with a process like process 3300 of FIG. 33. For example, values for characteristics of a cancerous lesion to use as conditions for selection of treatment options may be hard-coded into a medical device following at least some experimentation to determine a correspondence between the values, types of cancerous cells/tissues, and successful treatment with various treatment options. The inventors have recognized and appreciated, however, the advantages of a system to learn such relationships and conditions based on characteristics of cancerous cells/tissues and information on successful treatments of cancerous cells/tissues, among other information. For example, a machine learning process, such as one that may include feature extraction and/or classification, may be implemented in some embodiments.

Computer Implementation

Techniques operating according to the principles described herein may be implemented in any suitable manner. Included in the discussion above are a series of flow charts showing the steps and acts of various processes that characterize a lesion of a duct and/or generate one or more treatment recommendations for treatment of the lesion. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), Blu-Ray disk, a persistent or non-persistent solid-state memory (e.g., Flash memory, Magnetic RAM, etc.), or any other suitable storage media.

Such a computer-readable medium may be implemented in any suitable manner, including as computer-readable storage media 3406 of FIG. 34 described below (i.e., as a portion of a computing device 3400) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 34:
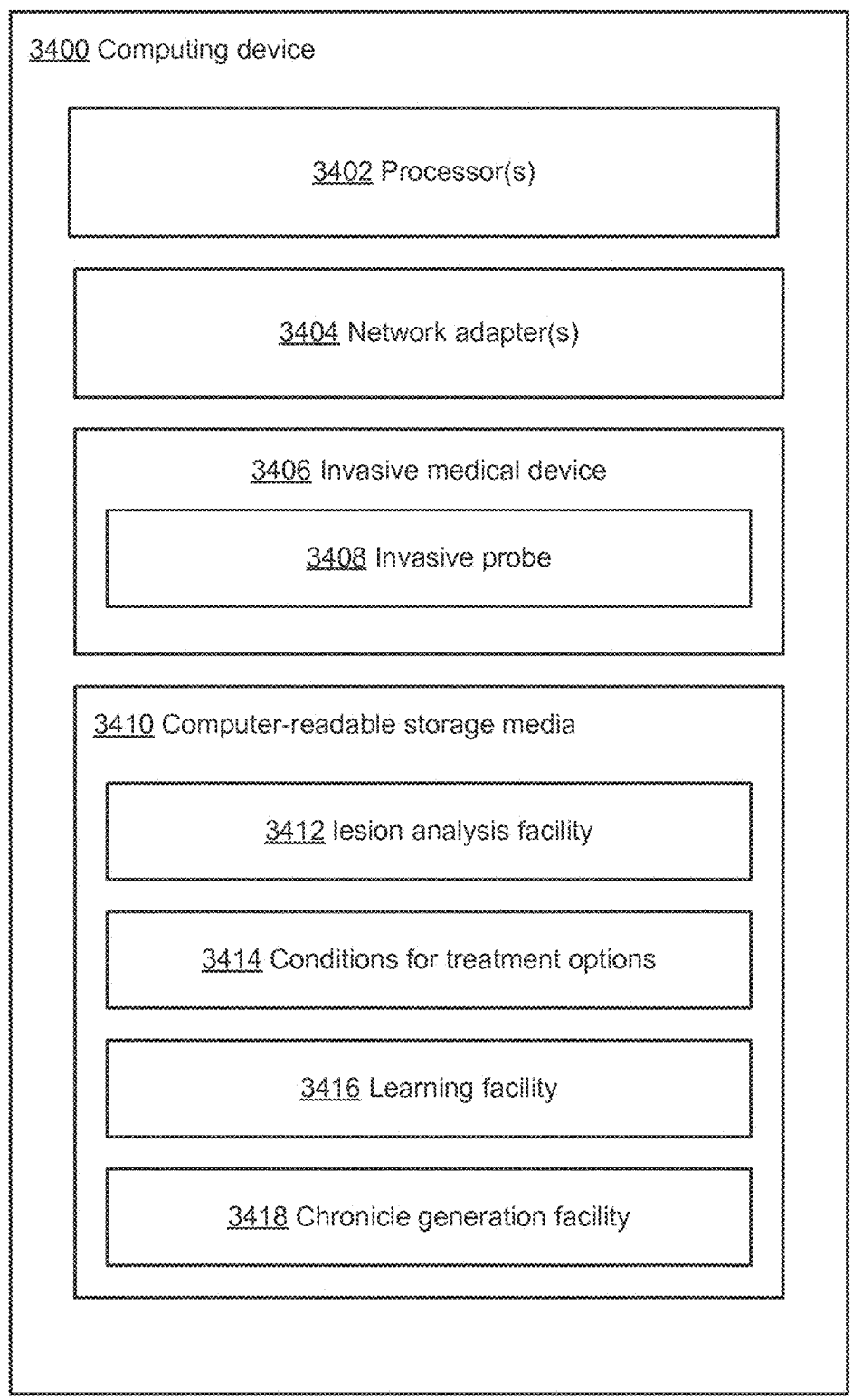
FIG. 34 is a block diagram of a computing device with which some embodiments may operate.

FIG. 34 illustrates one exemplary implementation of a computing device in the form of a computing device 3400 that may be used in a system implementing techniques described herein, although others are possible. It should be appreciated that FIG. 34 is intended neither to be a depiction of necessary components for a computing device to operate in accordance with the principles described herein, nor a comprehensive depiction.

Computing device 3400 may comprise at least one processor 3402, a network adapter 3404, and computer-readable storage media 3410. Computing device 3400 may be, for example, a medical device as described above, a desktop or laptop personal computer, a personal digital assistant (PDA), a smart mobile phone, a server, or any other suitable computing device. Network adapter 3404 may be any suitable hardware and/or software to enable the computing device 3400 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 3410 may be adapted to store data to be processed and/or instructions to be executed by processor 3402. Processor 3402 enables processing of data and execution of instructions. The data and instructions may be stored on the computer-readable storage media 3410.

In embodiments in which the device 3400 is a medical device as described herein, the device 3400 may include an invasive medical device 3406 that is to be inserted into anatomy of a subject to diagnose and/or treat the subject. The device 3406 includes an invasive probe 3408, as discussed above.

The data and instructions stored on computer-readable storage media 3410 may comprise computer-executable instructions implementing techniques which operate according to the principles described herein. In the example of FIG. 34, computer-readable storage media 3410 stores computer-executable instructions implementing various facilities and storing various information as described above. Computer-readable storage media 3410 may store a lesion analysis facility 3412 to analyze one or more characteristics of a lesion, including a composition of a lesion, and/or to determine a treatment recommendation based on the analysis. The computer-readable storage media 3410 may additionally store conditions 3414 for treatment options that may be used by the facility 3412. The computer-readable storage media 3410 may also store a learning facility 3416 and a chronicle generation facility 3418.

While not illustrated in FIG. 34, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets.

As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

The invention claimed is:

1. A method of training a system, the method comprising:
receiving training data including a plurality of sets of impedance measurements at least for a type of biological structure, each set of the plurality including impedance measurements for multiple different frequencies;
selecting, via a series of iterations and based at least in part on the plurality of sets of impedance measurements, a set of frequencies with which to configure a medical device for in vivo measurement of biological structures of the type, the set of frequencies including a fewer number of frequencies than all of the multiple different frequencies for which impedance measurements are included in the plurality of sets of impedance measurements, wherein the selecting comprises:
identifying for an iteration a first plurality of subsets of the training data including a first subset of impedance measurements from each set of the plurality of sets of impedance measurements, each first subset of the first plurality of subsets including impedance measurements for a first subset of frequencies for the iteration, the first subset of frequencies including the fewer number of frequencies than all of the multiple different frequencies for which impedance measurements are included in the plurality of sets of impedance measurements;
identifying for the iteration a first plurality of features from each first subset of the first plurality of subsets of the training data, the first plurality of features including for each first subset at least one derived feature that is not present in the first subset of impedance measurements and is derived from the first subset of the training data;
training a model using at least one machine learning technique with the first plurality of identified features to create a first trained model;
determining whether the first trained model for the iteration satisfies at least one performance criterion;
in response to determining that the at least one performance criterion is not satisfied by the first trained model for the iteration, continuing with the selecting in another iteration of the series of iterations; and
in response to determining that the at least one performance criterion is satisfied by the first trained model for the iteration, outputting the subset of frequencies for the iteration as the set of frequencies recommended to be used with the medical device for in vivo measurement.

2. The method of claim 1, wherein training the model comprises training the model to identify at least one characteristic of a biological structure, the at least one characteristic of the biological structure includes a composition of the biological structure.

3. The method of claim 1, further comprising:
configuring the medical device to obtain in vivo measurements of impedance of biological structures at frequencies of the set of frequencies output from the selecting; and
using the first trained model or another model trained based at least in part on the set of frequencies to identify at least one characteristic of a biological structure.

4. The method of claim 3, wherein using the first trained model or the another model to identify the at least one characteristic of the biological structure includes:
identifying that least one characteristic of the biological structure based on at least one acquired impedance measurement of the biological structure, for the set of frequencies output from the selecting and acquired using the medical device, using at least one machine learning parameter associated with the trained model or the another model.

5. The method of claim 1, further comprising:
in response to determining whether the first trained model meets the at least one performance criterion, configuring the medical device to obtain in vivo measurements of impedance of biological structures of the type at frequencies of the set of frequencies output from the selecting.

6. The method of claim 1, wherein:
the selecting via the series of iterations comprises, in a second iteration following a first iteration of the series of iterations, the first iteration being an iteration in which the first trained model of the first iteration was determined not to satisfy the at least one performance criterion:
identifying for the second iteration a second plurality of subsets of the training data including a second subset of impedance measurements from each set of the plurality of sets of impedance measurements, each second subset of the second plurality of subsets including impedance measurements for a second subset of frequencies, the second subset of frequencies including the fewer number of frequencies than all of the multiple different frequencies for which impedance measurements are included in the plurality of sets of impedance measurements and being a different set of frequencies than the first subset of the first iteration;
identifying a second plurality of features from each second subset of the second plurality of subsets of the training data, the second plurality of features including at least one derived feature that is not present in the second subset of impedance measurements and is derived from the identified second subset of the training data;
training using the at least one machine learning technique with the second plurality of identified features to create a second trained model; and
determining whether the second trained model of the second iteration meets the at least one performance criterion; and
using the second trained model to identify the at least one characteristic of the biological structure responsive to the second trained model of the second iteration meeting the at least one performance criterion, wherein using the second trained model comprises configuring the medical device to obtain in vivo measurements of impedance of biological structures of the type at frequencies of the second subset of frequencies.

7. The method of claim 6, wherein identifying the second subset comprises selecting the second subset of frequencies based at least in part on a genetic algorithm that receives as input the first subset of frequencies of the first iteration and a performance metric for the first trained model of the first iteration.

8. The method of claim 1, wherein:
the first plurality of features includes at least one feature present in each first subset of the first plurality of subsets of training data and the at least one derived feature for each first subset;
the at least one feature present in the subset comprises a value of an impedance measurement at a given frequency; and
the at least one derived feature for each first subset comprises a value determined from performing at least one computation on one or more impedance values of the first subset.

9. The method of claim 8, wherein performing the at least one computation comprises performing one or more statistical analyses on the one or more impedance values of the first subset.

10. The method of claim 8, wherein performing the at least one computation comprises determining a value indicative of a change between impedance measurements of the first subset.

11. The method of claim 1, wherein:
training the model comprises training at least one model to identify at least one characteristic of biological structures of the type;
the plurality of sets of impedance measurements include impedance measurements for a plurality of types of biological structures and each set of the plurality of sets indicates a type of biological structure to which the impedance measurements relate;
the training the at least one model comprises training a first model using the first plurality of identified features and, for each first subset of the plurality of subsets from which the first plurality of identified features were identified, an indication of a biological structure to which the first subset of impedance measurements relate;
the training comprises training the first model, based at least in part on the impedance measurements, to differentiate impedance measurements for the type of biological structure from impedance measurements for one or more other types of biological structures; and
the training the at least one model further comprises training a second model, at least in part by applying the at least one machine learning technique to impedance measurements for the first type of biological structure, to identify the at least one characteristic of the type of biological structure.

12. The method of claim 11, further comprising operating at least one processor to carry out acts of:
filtering an input set of impedance measurements of the plurality of sets using the first model to yield a filtered input set of impedance measurements relating to a first biological structure of the type; and determining the at least one characteristic for the first biological structure using the second model.

13. An apparatus comprising:
at least one medical device for obtaining in vivo impedance measurements of a biological structure, the at least one medical device comprising at least one impedance sensor to obtain impedance measurements of the biological structure in vivo using the at least one impedance sensor at a fixed set of frequencies, the fixed set of frequencies comprising a first frequency and a second frequency and the impedance measurements comprising a first impedance measurement at the first frequency and a second impedance measurement at the second frequency; and
at least one control circuit configured to:
derive at least one derived feature from the impedance measurements at the fixed set of frequencies, wherein the at least one control circuit is configured to derive the at least one derived feature at least in part by performing at least one computation on one or more of the impedance measurements at the fixed set of frequencies, the at least one derived feature comprising a first derived feature and the at least one control circuit is configured to derive the first derived feature at least in part by determining a value indicative of a change between the first impedance measurement at the first frequency and the second impedance measurement at the second frequency, and
process at least some of the impedance measurements and the at least one derived feature at least in part by evaluating the at least some of the impedance measurements and the at least one derived feature using at least one trained model that is trained to distinguish between biological structures having different characteristics.

14. The apparatus of claim 13, wherein:
the at least one trained model is at least one first trained model;
the at least one control circuit is further configured to filter one or more sets of impedance measurements, using at least one second trained model, to produce filtered impedance measurements, the received impedance measurements including at least some impedance measurements corresponding to the biological structure, the at least one second trained model trained to distinguish impedance measurements corresponding to the biological structure from impedance measurements not corresponding to the biological structure; and
the at least one control circuit is configured to evaluate the impedance measurements using the at least one first trained model at least in part by evaluating the filtered impedance measurements using the at least one first trained model.

15. The apparatus of claim 14, wherein:
the at least one second trained model is further configured to distinguish between erroneous and non-erroneous impedance measurements; and
filtering the one or more sets of impedance measurements comprises, using the at least one second trained model, detecting and removing any erroneous measurements.

16. The apparatus of claim 13, wherein the at least one circuit is configured to evaluate the impedance measurements using the at least one trained model at least in part by evaluating the impedance measurements using the at least one trained model to determine a manner in which to treat the lesion.

17. The apparatus of claim 16, wherein the at least one circuit is configured to evaluate the impedance measurements using the at least one trained model at least in part by performing one or more computations on the impedance measurements and on coefficients of the at least one trained model, wherein a result of the one or more computations indicates a manner in which the lesion is to be treated.

18. The method of claim 1, further comprising:
configuring the medical device to obtain in vivo measurements of impedance of biological structures of the type at frequencies of the first subset of frequencies; and
using the first trained model to identify a manner in which to treat a biological structure of the type.

19. At least one non-transitory computer-readable storage medium having encoded thereon executable instructions that, when executed by at least one processor, cause the at least one processor to carry out a method comprising:
receiving training data including a plurality of sets of impedance measurements at least for a type of biological structure, each set of the plurality including impedance measurements for multiple different frequencies;
selecting, via a series of iterations, a set of frequencies to be used with an invasive probe for in vivo measurement of biological structures of the type, the set of frequencies including a fewer number of frequencies than all of the multiple different frequencies for which impedance measurements are included in the plurality of sets of impedance measurements, wherein the selecting comprises in each iteration of the series of iterations:
identifying for the iteration a plurality of subsets of the training data including a first subset of impedance measurements from each set of the plurality of sets of impedance measurements, each subset of the plurality of subsets including impedance measurements for a subset of frequencies for the iteration, the subset of frequencies including the fewer number of frequencies than all of the multiple different frequencies for which impedance measurements are included in the plurality of sets of impedance measurements;
identifying for the iteration a plurality of features from each subset of the plurality of subsets of the training data, the plurality of features including for each subset at least one derived feature that is not present in the subset of impedance measurements and is derived from the subset of the training data;
training a model using at least one machine learning technique with the plurality of identified features to create a trained model;
determining whether the trained model satisfies at least one performance criterion;
in response to determining that the at least one performance criterion is not satisfied, continuing with the selecting in another iteration of the series of iterations; and
in response to determining that the at least one performance criterion is satisfied, selecting the subset of frequencies for the iteration as the set of frequencies to be used with the invasive probe for in vivo measurement.

20. The method of claim 18, wherein using the first trained model to identify a manner in which to treat the biological structure comprises identifying the manner in which to treat without identifying or characterizing the biological structure.

21. The apparatus of claim 17, wherein the at least one control circuit is a component of the at least one medical device.

22. The apparatus of claim 13, wherein the at least one control circuit is at least one processor.

23. The apparatus of claim 13, wherein the at least one control circuit is configured to perform the at least one computation to determine one or more other derived features of the at least one derived feature at least in part by performing one or more statistical analyses on the one or more of the impedance measurements.

* * * * *